US007264730B2

(12) United States Patent
Connell et al.

(10) Patent No.: US 7,264,730 B2
(45) Date of Patent: *Sep. 4, 2007

(54) METHODS FOR KIDNEY DIALYSIS

(75) Inventors: Mark E. Connell, Sandy, OR (US);
Robert A. Bedient, Portland, OR (US);
Raymond Elsen, Antwerp (BE);
Michael E. Hogard, Oregon City, OR (US); Harley D. Johnson, Portland, OR (US); Thomas D. Kelly, Portland, OR (US); Jean McEvoy Long, Portland, OR (US); Bruce A. Peterson, Milwaukie, OR (US); William G. Preston, Jr., Portland, OR (US); Dalibor J. Smejtek, Beaverton, OR (US)

(73) Assignee: Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/461,237

(22) Filed: Jun. 13, 2003

(65) Prior Publication Data

US 2003/0222022 A1 Dec. 4, 2003

Related U.S. Application Data

(60) Continuation of application No. 09/711,240, filed on Nov. 13, 2000, now abandoned, which is a continuation of application No. 09/067,922, filed on Apr. 28, 1998, now abandoned, which is a continuation of application No. 08/479,688, filed on Jun. 7, 1995, now Pat. No. 5,744,027, which is a division of application No. 08/122,047, filed on Sep. 14, 1993, now Pat. No. 5,486,286, which is a division of application No. 07/688,174, filed on Apr. 19, 1991, now Pat. No. 5,247,434.

(51) Int. Cl.
*B01D 61/32* (2006.01)
(52) U.S. Cl. .............. 210/646; 210/138; 210/143; 210/321.65; 210/929; 345/156; 345/173; 345/530; 604/6.09; 700/273
(58) Field of Classification Search ............ 210/85, 210/87, 90, 96.2, 321.65, 321.69, 321.72, 210/636, 646, 647, 739, 745, 929, 138, 143; 604/4.01, 5.01, 6.01, 6.09; 345/173, 156, 345/530; 700/273; 705/2, 3
See application file for complete search history.

(56) References Cited

U.S. PATENT DOCUMENTS 3,515,275 A 6/1970 Bowman (Continued)

FOREIGN PATENT DOCUMENTS

DE 3428828 2/1986

(Continued)

OTHER PUBLICATIONS

Reply Memorandum In Support of Baxter's Rule 50(b) Renewed Motion For Judgment As A Matter of Law dated Aug. 23, 2006.

(Continued)

*Primary Examiner*—Joseph Drodge
(74) *Attorney, Agent, or Firm*—Joseph P. Reagan; Bell, Boyd & Lloyd LLC

(57) ABSTRACT

A number of improvements relating to methods and apparatuses for kidney dialysis are disclosed. These include methods such as supplying a dialysis machine including a touch screen interface to a machine user and supplying to the machine user accessory devices to be used with the dialysis machine in operation.

15 Claims, 11 Drawing Sheets

U.S. PATENT DOCUMENTS

| | | |
|---|---|---|
| 3,563,381 A | 2/1971 | Edelson et al. |
| 3,662,105 A | 5/1972 | Hurst et al. |
| 3,754,649 A | 8/1973 | Palubniak et al. |
| 3,774,762 A * | 11/1973 | Lichtenstein ............... 210/94 |
| 3,798,370 A | 3/1974 | Hurst |
| 3,946,731 A | 3/1976 | Lichtenstein |
| 3,992,301 A | 11/1976 | Shippey et al. |
| 3,996,027 A | 12/1976 | Schnell et al. |
| 4,079,007 A * | 3/1978 | Hutchisson ............... 210/85 |
| 4,096,059 A | 6/1978 | Pinkerton |
| 4,098,274 A | 7/1978 | Ebling et al. |
| 4,138,460 A | 2/1979 | Tigner |
| 4,152,554 A | 5/1979 | von der Heide et al. |
| 4,153,554 A | 5/1979 | von der Heide et al. |
| 4,202,760 A | 5/1980 | Storey et al. |
| 4,209,391 A | 6/1980 | Lipps et al. |
| 4,211,597 A | 7/1980 | Lipps et al. |
| 4,217,642 A | 8/1980 | Dam et al. |
| 4,226,124 A | 10/1980 | Kersten |
| 4,231,871 A | 11/1980 | Lipps et al. |
| 4,267,040 A | 5/1981 | Schäl |
| 4,299,705 A | 11/1981 | Russell |
| 4,314,480 A | 2/1982 | Becker |
| 4,332,464 A | 6/1982 | Bartulis et al. |
| 4,334,988 A | 6/1982 | Milligan |
| 4,366,061 A | 12/1982 | Papanek et al. |
| 4,370,983 A | 2/1983 | Lichtenstein |
| 4,396,977 A | 8/1983 | Slater et al. |
| 4,411,603 A | 10/1983 | Kell |
| 4,412,916 A | 11/1983 | Kell |
| D271,801 S | 12/1983 | Preussner |
| 4,444,596 A * | 4/1984 | Gortz et al. ............... 134/18 |
| 4,477,342 A | 10/1984 | Allan et al. |
| 4,508,622 A | 4/1985 | Polaschegg et al. |
| 4,509,526 A | 4/1985 | Barnes et al. |
| 4,517,081 A | 5/1985 | Amiot et al. |
| 4,548,082 A | 10/1985 | Engebretson et al. |
| 4,555,699 A | 11/1985 | Citron et al. |
| 4,570,217 A | 2/1986 | Allen et al. |
| 4,577,639 A | 3/1986 | Simon et al. |
| 4,582,598 A | 4/1986 | Bilstad et al. |
| 4,601,830 A | 7/1986 | Chen |
| 4,614,590 A | 9/1986 | Rath et al. |
| 4,618,343 A | 10/1986 | Polaschegg |
| 4,629,015 A | 12/1986 | Fried et al. |
| 4,649,499 A | 3/1987 | Sutton et al. |
| 4,696,671 A | 9/1987 | Epstein et al. |
| 4,715,959 A | 12/1987 | Allan et al. |
| 4,718,022 A | 1/1988 | Cochran |
| 4,725,694 A * | 2/1988 | Auer et al. ............... 345/173 |
| 4,725,706 A | 2/1988 | Inoue |
| 4,731,731 A | 3/1988 | Cochran |
| 4,739,492 A | 4/1988 | Cochran |
| 4,742,831 A | 5/1988 | Silvian |
| 4,747,950 A | 5/1988 | Guinn |
| 4,756,706 A | 7/1988 | Kerns et al. |
| 4,766,425 A | 8/1988 | Tallman et al. |
| 4,769,134 A | 9/1988 | Allan et al. |
| 4,770,769 A | 9/1988 | Schael |
| 4,790,937 A | 12/1988 | Eilers |
| 4,796,634 A | 1/1989 | Huntsman et al. |
| 4,804,950 A | 2/1989 | Moon et al. |
| 4,809,697 A | 3/1989 | Causey, III et al. |
| 4,809,937 A | 3/1989 | Emory, Jr. |
| 4,812,239 A | 3/1989 | Mills et al. |
| 4,822,456 A | 4/1989 | Bryan |
| 4,827,430 A | 5/1989 | Aid et al. |
| 4,828,543 A | 5/1989 | Weiss et al. |
| 4,828,693 A | 5/1989 | Lindsay et al. |
| 4,834,888 A | 5/1989 | Polaschegg |
| 4,838,887 A | 6/1989 | Idriss |
| 4,839,806 A | 6/1989 | Goldfischer et al. |
| 4,839,822 A | 6/1989 | Dormond et al. |
| 4,847,785 A | 7/1989 | Stephens |
| 4,853,521 A | 8/1989 | Claeys et al. |
| 4,867,685 A | 9/1989 | Brush et al. |
| 4,873,623 A | 10/1989 | Lane et al. |
| 4,895,657 A | 1/1990 | Polaschegg |
| 4,898,578 A | 2/1990 | Rubalcaba, Jr. |
| 4,898,822 A | 2/1990 | Asada et al. |
| 4,907,973 A | 3/1990 | Hon |
| 4,914,624 A | 4/1990 | Dunthorn |
| 4,916,441 A | 4/1990 | Gombrich |
| 4,933,873 A | 6/1990 | Kaufman et al. |
| 4,935,125 A | 6/1990 | Era et al. |
| 4,942,514 A | 7/1990 | Miyagaki et al. |
| 4,945,476 A | 7/1990 | Bodick et al. |
| 4,966,691 A | 10/1990 | Brous |
| 4,971,700 A | 11/1990 | Tsuji et al. |
| 4,974,599 A | 12/1990 | Suzuki |
| 4,979,506 A | 12/1990 | Silvian |
| 4,979,949 A | 12/1990 | Matsen, III et al. |
| 4,984,575 A | 1/1991 | Uchiyama et al. |
| 4,990,258 A | 2/1991 | Bjare et al. |
| 4,991,193 A | 2/1991 | Cecil et al. |
| 4,997,570 A | 3/1991 | Polaschegg |
| 5,024,756 A | 6/1991 | Sternby |
| 5,049,141 A | 9/1991 | Olive |
| 5,054,774 A | 10/1991 | Belsito |
| 5,056,059 A | 10/1991 | Tivig et al. |
| 5,059,167 A | 10/1991 | Lundquist et al. |
| 5,069,668 A | 12/1991 | Boydman |
| 5,077,769 A | 12/1991 | Franciose |
| 5,088,045 A | 2/1992 | Shimanaka et al. |
| 5,098,426 A * | 3/1992 | Sklar et al. ............... 606/5 |
| 5,100,554 A | 3/1992 | Polaschegg |
| 5,104,374 A | 4/1992 | Bishko et al. |
| 5,111,683 A | 5/1992 | Fond |
| 5,119,295 A | 6/1992 | Kapur |
| 5,189,609 A | 2/1993 | Tivig et al. |
| 5,190,185 A | 3/1993 | Blechl |
| 5,247,434 A | 9/1993 | Peterson et al. |
| 5,252,213 A | 10/1993 | Ahmad et al. |
| 5,274,028 A | 12/1993 | Bertrand et al. |
| 5,276,611 A | 1/1994 | Ghiraldi |
| 5,319,363 A | 6/1994 | Welch et al. |
| 5,326,476 A | 7/1994 | Grogan et al. |
| 5,330,481 A | 7/1994 | Hood et al. |
| 5,344,392 A | 9/1994 | Senninger |
| 5,417,969 A | 5/1995 | Hsu et al. |
| 5,486,286 A | 1/1996 | Peterson et al. |
| 5,541,167 A | 7/1996 | Hsu et al. |
| 5,744,027 A | 4/1998 | Connell et al. |
| 6,284,131 B1 | 9/2001 | Hogard et al. |

FOREIGN PATENT DOCUMENTS

| | | |
|---|---|---|
| DE | 3442744 A1 | 6/1986 |
| EP | 0 089 003 A2 | 3/1983 |
| EP | 0 089 003 | 9/1983 |
| EP | 0 089 003 A2 | 9/1983 |
| EP | 0 186 973 | 7/1986 |
| EP | 0 214 803 A2 | 3/1987 |
| EP | 0 298 587 | 5/1987 |
| EP | 0 240 101 | 10/1987 |
| EP | 0 251 520 A2 | 1/1988 |
| EP | 0 267 664 | 5/1988 |
| EP | 0 311 709 | 4/1989 |
| FR | 2 390 173 | 12/1978 |
| FR | 2 513 884 | 10/1982 |
| GB | 2 093 800 A | 9/1982 |
| GB | 2 110 564 A | 6/1983 |
| GB | 2 205 669 | 12/1988 |
| JP | 54-153781 | 6/1978 |

| | | |
|---|---|---|
| JP | S64-80370 | 5/1988 |
| JP | 1-162747 | 6/1989 |
| WO | WO 86/01115 | 2/1986 |
| WO | WO 88/05691 | 8/1988 |
| WO | WO90/14850 | 12/1990 |

OTHER PUBLICATIONS

Order from the District Court for the Northern District of California granting Baxter's Motion for Judgment as a Matter of Law dated Feb. 12, 2007 (20 pages).
Operator's Manual for SPS 550. Published by Baxter Healthcare Corp., 1987.
Operator's Instructions for A2008 Hemodialysis System. Published by Fresenius, pp. 1-116, undated.
HD-secura Dialysis Unit Operating Manual. Published by B. Braun Melsundsen AG, Jan. 1991, pp. 1-157.
Lamberti et al, "A Digital Computer Model for Optimal Programming of Hemodialytic Treatment," The International Journal of Artificial Organs, vol. 11, No. 4, 1988, pp. 235-242.
Nephrology Dialysis Transplantation, vol. 2, No. 2, 1987.
Monitral-S Dialysis System Brochure, Jan. 1988, vol. 1, No. 1.
Nephrology Dialysis Transplantation, vol. 3, No. 4, 1988.
Zucchelli, et al., Treatment and Monitoring of Renal Patients, Nephrology Dialysis Transplantation, Symposium 27-29, Apr. 1989 at Bologna, Italy.
Nephrology Dialysis Transplantation, vol. 4, No. 12, 1989.
COBE Laboratories Centrysystem 3 Dialysis Management System Brochure, 1989.
Gambro AB, More Care in Renal Care, AK 100 Brochure, undated.
Gambro AB, AK 100 Ultra One Step Above Brochure, undated.
Gambro AB, Haemodialysis Equipment Brochure, Dec. 1990, Evaluation No. 47.
Fresenius, The A 2008 D Dialysis System Brochure, undated.
Fresenius, A 2008 D Dialysis System Brochure, undated.
Baxter Healthcare Corporation, The Baxter 1550 Hemodialysis Machine Brochure, 1991.
Hospal Integra, The Hospal Vision of the Future in Dialysis Monitoring Brochure, undated.
Hanna, Annetta, 1991 Annual Design Review, Introduction.
Althin CD Medical, Inc.; reprint of: Winning Design for Althin's System 1000; Jun. 12 issue of Clinica, undated.
International Design Prize of the State of Baden-Wurttemberg brochure; 1993.
Fresenius, 4008 Profile Display, Na/UF Graphics Brochure, undated.
Fresenius, 4008 E Dialysis System Brochure, undated.
Fresenius, 2008 H Dialysis System Brochure, undated.
Fresenius, The Highest Standards in Hemodialysis Brochure, undated.
Communication of a Notice of Opposition from the European Patent Office dated Jan. 5, 2001.
Objection on behalf of B. Braun Melsungen AB to Patent 0 668 793 B1 by von Kresler et al. Patent Attorneys dated Jan. 2, 2001 (with translation).
CMS 08 Handbook dated Aug. 4, 1988, published by Fresenius AG (with translation).
Communication of a Notice of Opposition from the European Patent Office dated Jan. 16, 2001.
Objection to European Patent EP—0 668 793 B1 by Luderschmidt et al. Patent Attorneys on behalf of Fresenius Medical Care dated Jan. 4, 2001 (with translation).
Einspruch gegen ein europlisches Patent (6 pages), undated.
CMS 08 Handbook dated Aug. 4, 1988, published by Fresenius AG.
Computer Modelling System 08, CMS 08 document, published by Fresenius AG, undated.
Dialysis System A2008 C document published by Fresenius AG.
Erben, J. et al., "Computer-Supported Risk Analysis of Haemodialysis Patients in Combination with Possible Therapies by the CMS 08," Improvements in Dialysis Therapy, 1989, vol. 74, p. 165, undated.
Stefoni, S. et al., "The CMS 08 Modulated Dialysis," Improvements in Dialysis Therapy, 1989, vol. 74, p. 221.
Deuber, H.J. et al., "Clinical Application of the Sodium Modelling Computation with CMS 08," Improvements in Dialysis Therapy, 1989, vol. 74, p. 159.
Eidesstattliche Versicherung (Solemn Declaration) for Raimond Walter dated Jan. 2, 2001 (with translation), undated.
Photograph labeled Anlage 8, undated.
Programme for European Renal Association XXIXth Congress, 5 pages, undated.
Photograph labeled Anlage 10, undated.
Photograph labeled Anlage 11, undated.
Eidesstattliche Versicherung (Solemn Declaration) for Reiner Spickermann dated Dec. 27, 2000 (with translation).
Beaumont, J. G., et al., "A clinical field study of eight automated psychometric procedures: the Leicester/DHSS project," International Journal of Man-Machine Studies, vol. 26, No. 2, Jan. 1987, (pp. 661-682).
Dr. Richard A. Bolt, Spatial Data Management, MIT, 1979, pp. 2-29.
Benel, R., et al., "Human-Computer Interaction-Interact '87," Proceedings of the Second IFIP Conference on Human-Computer Interaction held at the University of Stuttgart, Federal Republic of Germany, Sep. 1-4, 1987, (pp. 581-585).
Daugirdas, J., et al., "A Double-Blind Evaluation of Sodium Gradient Hemodialysis," American Journal of Nephrology, vol. 5, (pp. 163-168), undated.
Ebel, H., et al., "Influence of Computer-Modulated Profile Haemodialysis on Cardiac Arrhythmias," Nephrological Dialysis and Transplant, Supplement 1, 1990, (1 pg.).
Erben, J., et al. "Computer-Supported Risk Analysis of Haemodialysis Patients in Combination with Possible Therapies by the CMS 08," Improvement in Dialysis Terapy, Contrib Nephrology, vol. 74, 1989, (pp. 165-169).
Gentles, W., et al., "Programmable machine for dialyser reuse," Medical and Biological Engineering and Computing, vol. 18, Nov. 1980, (pp. 765-771).
Goureau, Y., et al., "Evaluation of Plasma Sodium Concentration During Hemodialysis by Computerization of Dialysate Conductivity," ASAIO Transactions, vol. 36, No. 3, ISSN 0889-7190, Jul.-Sep. 1990, (pp. M444-M447).
Gungl, K., et al., "Computer Interface and Touch Sensitive Screens," Proceedings VLSI and Computer Peripherals, VLSI and Microelectronic Applications in Intelligent Peripherals and their Interconnection Networks, Hamburg, May 8-12, 1989, (pp. 2-98-2-100).
Keuchel, M., et al., Fluid-shift during computer-modulated profile hemodialysis (CMP-HD), The International Journal of Artificial Organs, vol. 14, No. 10, 1991, (pp. 631-633).
Klocke, H., et al., "An Anesthesia Information System For Monitoring And Record Keeping During Surgical Anesthesia," Journal of Clinical Monitoring, vol. 2, No. 4, Jan.-Oct. 1986, (pp. 246-261).
Morrison, S., et al., "The touch screen system in the pigeon laboratory: An initial evaluation of its utility," Behavior Research Methods, Instruments, & Computers, A Journal of The Psychonomic Society, Inc., vol. 22, No. 2, Apr. 1990, (pp. 123-126).
Perrone, B., et al., "Evidence of Fluid Shifts during Dialysis Sessions with Sodium and Ultrafiltration Profiles," Improvements in Dialysis Therapy, Contrib Nephrology, vol. 74, 1989, (pp. 191-199).
Brian Petheram, "Enabling stroke victims to interact with a microcomputer—a comparison of input devices," international Disability Studies, vol. 10, No. 2, 1988, (pp. 73-80).
Pye, S.D., PhD, et al., "The use of an infrared touch-screen to control the sensitivity of ultrasound scanners in clinical practice," The British Journal of Radiology, vol. 62, No. 743, 1989, (pp. 1014-1016).
Rau, G., et al., "Ergonomic Design Aspects In Interaction Between Man and Technical Systems in Medicine," Medical Progress through Technology, vol. 9, 1982, (pp. 153-159).
Gunter Rau, "Ergonomie and Anwendungsaspekte in der Medizin," Richard Wolf GmbH, 1989 (pp. 7-63); English translation: Ergonomics and Aspects of Application in Medicine (pp. 2-55).
Stefoni, S., et al., "Modulated Dialysis: A New Strategy for the treatment of Intradialytic Intolerance," Nephrological Dialysis Transplant, Supplement 1, European Dialysis and Transplant Association-European Renal Association, 1990, (pp. 154-157).

Sturniolo, A., et al., "Computerised Monitoring of Sodium and Fluid During Haemodialysis," Nephrological Dialysis and Transplant, Supplement 1, European Dialysis and Transplant Association-European Renal Association, 1990, (pp. 162-164).

Pierre Susung, Dialogue home/machine: du bouton-poussoir au terminal industriel—Man-machine dialogue: from the pushbutton to the industrial terminal, Journal de L'Equipment Electrique et Electronique, No. 604, Nov. 1990, (pp. 37-38, 41-42, 48-49, 51).

Interactive Pharmacy Kiosks: "User-Friendly PIC Dispenses Drug Information," Chain Store Age Executive, vol. 66, No. 6, Jun. 1990, (pp. 9, 49, 52).

The Basis of the Dialysis System A 2008 C, Fresenius AG, 1988, (pp. 2-19).

Gebrauchsanweisung Hamodialysegerat A 2008 C, Fresenius AG, 1989, 1991, (47 pgs.).

Operating Instructions, Haemodialysis machine A 2008 D, Fresenius AG, 1989, (92 pgs.).

Operating Instructions A 2008 C Haemodialysis Unit, Fresenius AGm 1991, (65 pgs.).

A2008D Operator's Manual, Fresenius USA, P/N 500130 Rev. G., 1989-1996, (195 pgs.).

A1008D, Part 1: Operating Instructions 2$^{nd}$ Edition, Fresenius, Nov. 1984, (88 pgs.).

A1008D, Part 2: Technical Description, 1$^{st}$ Edition, Fresenius AG, Nov. 1984 (88 pgs.).

General Description—A 2008 D, Fresenius AG, 1989, (4 pgs.).

Technician's Manual, A2008 Hemodialysis System, Fresenius USA, Inc., P/N 450033 Rev. 1, 1988, (539 pgs.).

Fresenius Hemodialysis Machine, A2008E Technicians Manual, P/N 450058 Rev. 1, 1998 and 1996, (558 pgs.).

Operator Instructions, Fresinius Hemodialysis Machine 2008BSS, Manual 460001 Rev: B, 1990 and 1993, (56 pgs.).

Fresenius USA, A2008 BSS Technical Manual Part #450126 Rev. B.. 1989 and 1991. (167 pgs.).

COBE, Centry 2, Centry 2Rx Dialysis Control Units and Centry Ultrafiltration Control Module Operator's Manual, Aug. 1990, (261 pgs.).

COBE, Centurysystem2, Ultrafiltration Control Module (UFCM) Service Manual, Aug. 1990, (321 pgs.).

COBE Centrysystem 3, Dialysis Control Unit, Maintenance and Troubleshooting Service Manual, 1990, (421 pgs.).

CMS 08—Handbook, 1998 and the English translation, (117 pgs.), undated.

Seratron Dialysis Control System, Technician's Manual, Catalog No. 271-301, Cordis Dow Corp., (269 pgs.), undated.

Specification, Seratron PRSM System Level I, (35 pgs.), undated.

Cordis Dow Seratron Operations Manual, 1979 and 1980, (125 pgs.).

Maintenance Manual, 7300 Single Patient Delivery System, Drake Willock, 1984, (236 pgs.).

Old-Computers.com: The Museum, HP-150 touch screen computer, sold or offered for sale by Hewlett Packard. See http://www.old-computers.com/museum/computer.asp?st=1&c=139, as of Nov. 19, 2003, (3 pgs.), undated.

HP-150 Touchscreen Personal Computer with HP 9121 Dual Drives, Hewlett Packard website; 1983, (5 pgs.).

Memo to Ben Lipps from Wayne Merryman regarding FDS 08 Development dated Dec. 5, 1986, (2 pgs.).

Operator's Manual, Drake Willock 480 Ultrafiltration Control, Single Patent Delivery System, CD Medical, Inc., 1988, (96 pgs.).

Letter to Mr. J. James Li from Scott Walker, Vice President, R&D Equipment dated Jul. 2, 2003 enclosing the revision of history of the 2008E Operator's Manual, (117 pgs.).

Operator Instructions, Fresenius Hemodialysis Machine A2008E, Manual 450056 Rev. A, 1989, (107 pgs.).

Seratron Dialysis Control System, Cordis Dow Corp., 1979, (16 pgs.).

Seratron Dialysis Control System, Cordis Dow Corp., 1980, (123 pgs.).

Seratron™ Dialysis Control System, Cordis Dow Corp., UF Rate Accuracy Intradialytic Measurements Actual vs. Display ml/hr, (20 pgs.), undated.

*Fresenius Medical Care Holdings, Inc.'s and Fresenius USA, Inc.'s Final Invalidity Contentions Pursuant to Patent L.R. 3-6*, litigation document, produced by Fresenius Medical Care Holdings, Inc., and Fresenius USA, Inc. (Jan. 2005). (123 pages).

*750 RO Unit Drake Willock System 1000 Delivery System*, published by Althin Medical, Inc., (apparently undated). (2 pages).

*The A2008D Dialysis System* (redacted), published by Fresenius AG, (apparently undated). (4 pages).

*AK 10 System*, Gambro, (apparently undated). (1 page).

*AK-10 System Ultrafiltration Monitor*, Gambro, (1983). (3 pages).

*Behavior & Information Technology*, published in Taylor & Francis LTD, London, (Jul.-Sep. 1982). (21 pages).

*Bicarbonate Proportioning Unit Specifications*, Drake Willock, (apparently undated). (1 page).

*Bicarbonate Proportioning Unit Specifications, 7702A* Drake Willock, (1984). (1 page).

*BVS*, written by Gambro, (apparently undated). (6 pages).

*Centrysystem 3—The System For Dynamic Dialysis*, published in Contemporary Dialysis & Nephrology Magazine, (Nov. 1986). (4 pages).

*CRRT, The Acute Renal Therapy Solution*, published by Fresenius Medical Care, (apparently undated). (6 pages).

*Computer-Aided Nuclear Medicine Patient Scheduling and Reporting System* (abstract in English), published by Proc AIIE Annu Conf. Conv. 26th, 1975, for Meet, Washington, DC, (1975). (1 page).

*Computer Aids to Clinical Decisions*, (vol. I), published by CRC Press, Inc. (1982). (4 pages).

*Computer Applications to Private Office Practice*, published by Springer-Verlag (1984). (4 pages).

*Computer Dialysis System, Inc.*, (apparently unauthored), (apparently undated). (14 pages).

*Computer-Modulated Profile Hemodialysis Versus Standard BiCardonate Hemodialysis*, Keuchel et al., (apparently undated). (2 pages).

*Computers and Data Processing*, published by Academic Press, Inc. (1984). (8 pages).

*Computers in Critical Care and Pulmonary Medicine, Towards a Coherent Structure of the Anesthetist, Computer Interface* (redacted), published by Springer-Verlag, (1985), pp. 29-37. (11 pages).

*Computers in Medicine*, published by Computer Science Press (1987). (5 pages).

*A Conceptual Approach for an Advanced Controller for Hemodialysis and Hemofiltration*, published by the U.S. Department of Commerce National Technical Information Service (Mar. 27, 1981). (77 pages).

*The Crashcart Companion: Microprocessor Assisted Code Management and Training Article*, published by BioSoft Medical, Inc. (1989). (2 pages).

*CRRT: The Acture Renal Therpay Solution*, Fresenius Medical Care, (apparently undated). (6 pages).

*Current Perspectives in Health Computing*, published by Cambridge University Press, (apparently undated). (5 pages).

*DBB-05*, written by Nikkiso, (apparently undated). (4 pages).

*Decision of Jan. 29 2003, Case No. T 0838/02—3.3.7, Apparatus for Kidney Dialysis*, Althin Medical, Inc. (2003). (7 pages).

*Decision Models and the Design of Knowledge Based Systems*, published by Springer-Verlag Berlin Heidelberg, (1985). (13 pages).

*Designing the User Interface: Strategies for Effective Human-Computer Interaction*, published by Addison-Wesley Publishing Company (1987). (6 pages).

*Designing and Using Human, Computer Interfaces and Knowledge Based Systems*, (apparently unauthored), (Sep. 18-22, 1989). (9 pages).

*A Development Environment for the Design of Multimodal, Colourgraphic Human-Computer Interfaces* (redacted), published by Elsevier Science Publishers B.V. (North-Holland) (1990), pp. 1021-1024. (4 pages).

*Dialog*, written by B. Braun Melsungen AG, (apparently undated). (12 pages).

*Dialysis, Gently*, published by Business Week (Jun. 17, 1991). (1 page).
*Dialysis Data Terminal Specification*, (apparently unauthored), (Aug. 21, 1990). (2 pages).
*The Eighth Annual Symposium on Computer Applications in Medical Care Proceedings*, published by The Institute of Electrical and Electronics Engineers Inc. (Nov. 1984). (9 pages).
*Ergonomics in Medicine*, published by Helmholtz Institut, (1989/1990). (29 pages).
*Ergonomie in der Intensivmedizin*, von W. Friesdorf, (1990). (5 pages).
*Evaluation Report: Dialysis and Ancillary Equipment*, (apparently unauthored), (apparently undated). (7 pages).
*Exploring the Home-Based Use of Microcomputers in Aphasia Therapy*, published in Aphasiology, vol. 10, No. 3, 267-282 (apparently undated). (16 pages).
*FDS-08, CMS-08 and CMS-308*, published by Fresenius USA, (apparently undated). (2 pages).
*FDS-08 Fresenius Documentation System*, published by Fresenius Medical Care (apparently undated). (5 pages).
*First-Class Heamodialysis Comfort*, B. Braun Melsungen AG/W, Germany, (apparently undated). (3 pages).
*Formaldehyde Kinetics In Reused Dialyszers*, F.A. Gotch, et al., (vol. XXIX Trans Am Soc Artif Intern Organs), (1983). (6 pages).
*Forschungsbericht Research Report 1985/86, Ergonomie in Der Medizin* (redacted), published by Helmholtz-Institut für Biomedizinesche Technik, (apparently undated). (26 pages).
*Forschungsbericht Research Report 1989/90, Ergonomie in Der Medizin* (redacted), published by Helmholtz-Institut für Biomedizinesche Technik, (apparently undated). (29 pages).
*The Fourth Annual Symposium on Computer Applications in Medical Care Proceedings*, (vol. 3 of 3), published by The Institute of Electrical and Electronics Engineers Inc. (Nov. 1980). (7 pages).
*Fresenius USA 2008H Featuring On-Line Data Management*, written by Fresenius USA (1999). (6 pages).
*The Fresenius 2008K Machine*, written by Fresenius Medical Care (2000). (4 pages).
*Future Trends in Biocompatibility Aspects of Hemodialysis and Related therapies*, Clinical Nephrology, (vol. 26, Suppl. No. 1), S. Shaldon, (1986). (4 pages).
*Gambro Hemofiltration System 10, GHS-10*, copyright by Gambro AB, (1986). (3 pages).
*The Guardian Brain Activity Monitor*, published in The Journal of The American Society of Anesthesiologists, Inc. (vol. 70, No. 3), (Mar. 1939). (2 pages).
*The Hewlett Packard Component Monitoring System*, published in European Heart Journal (vol. 10), (Dec. 1989). (4 pages).
*HD—Secura Dialysis System*, Organon Teknika, N.V., (apparently undated). (2 pages).
*Hydrogen Ion Balance in Dialysis Therapy*, International Society for Artificial Organs, Frank A. Gotch et al., (apparently undated). (8 pages).
*Impact of Sodium and Ultrafiltration Profiling on Hemodialysis-Related Symptoms*, published by the Journal of the American Society of Nephrology (2001). (6 pages).
*Innova: The Standard In Dialysis Quality Control*, Hospal, (apparently undated). (11 pages).
*Intelligent Decision Support in Process Environments*, Spanger-Verlag, (published in cooperation with NATO Scientific Affairs Division), (apparently undated). (23 pages plus 13 pages).
*An Interactive Computer Simulator of the Circulation for Knowledge Acquisition in Cardio-Anesthesia* (redacted), published by the International Journal of Clinical Monitoring and Computing (1991). (8 pages).
*International Federation for Medical and Biological Engineering Proceedings North Sea Conference on Biomedical Engineering 1990, An Interactive Real-Time Computer Simulator of the Cardio-Vascular System Supporting Knowledge Acquisition in Cardio-Anesthesia* (redacted), published by Helmholz-Institute for Biomedical Engineering, Aachen, Germany and Clinic of Anesthesiology, Aachen University of Technology, Germany (1990). (5 pages).

*An Introduction to Computer Applications in Medicine*, published by Edward Arnold (Publishers) Ltd. (1982). (5 pages).
*Introduction to Computers and Information Systems*, published by Macmillan Publishing Company (1986). (3 pages).
*Knowledge Programming in Loops; Report on an Experimental Course*, Time Magazine, Mark Stefik et al., (Fall 1983). (11 pages).
*Lecture Notes in Medical Informatics, Databases for Health Care*, published by Springer-Verlag (1981). (3 pages).
*Lecture Notes in Medical Informatics, Expert Systems and Decision Support in Medicine* (redacted), published by Springer-Verlag, (apparently undated). (9 pages).
*A Low-Cost Computer-Assisted Teaching Package for Kidney Dialysis: A Preliminary Report*, published in the Journal of Medical Engineering & Technology, (vol. 14, No. 4) (Jul./Aug. 1990). (4 pages).
*Man-Machine Dialogue: From the Pushbutton to the Industrial Terminal* (abstract in English), published by Journal de L-equipment Electrique et Electronique (No. 604), (Nov. 12, 1990), pp. 37-38, 41-42, 44-45, 48-49, 51. (1 page).
*Mathematic Modeling of Dialysis Therapy*, published in Kidney International (Olv. 18, Suppl. 10), John A. Sargent et al., (1980). (9 pages).
*Medical Computing and Applications*, published by Halstead Press (1987). (7 pages).
*Microcomputer-Based Anaesthetic Record System*, published in The Macmillan Press Ltd, J.W. Prentice et al. (1984). (5 pages).
*Monitrals*, Hospal, (apparently undated). (3 pages).
*New Therapeutic Strategies in Nephrology*, Victorio E. Andraucci, M.D., (May 27-30, 1990). (10 pages).
*Nikkiso DBB-03*, written by Nikkiso Co., Ltd. and Nikkiso Medical GmbH, (apparently undated). (6 pages).
*On-Line Clearance*, published by Fresenius Medical Care, (apparently undated). (2 pages).
*Panel Conference, Acetate Versus BiCarbonate in Dialysis* (vol. XXVII), Trans Am Soc Artif Intern Organs, (1981). (3 pages).
*Panel Conference, Clearance and Ultrafiltration of Reused Dialyzers*, (apparently unauthored), (apparently undated). (2 pages).
*Patent—Computer Modulated Profile Hemodialysis (CMP-HD) and Vasoactive Hormores*, Lange, et al. (Centre Internal Medicine, Dept's of Nephrology, Endocrinology and Institute or Biomed, Statistics, Philipps-University of Marburg, F.R.G.) (apparently undated). (3 pages).
*Physician-Generated Clinical Records Using a Menu-Driven, Touch-Panel Microcomputer*, published by Medical Information Systems (1980). (7 pages).
*Picture Clears for Industrial Touch Screens*, published by Machine Design (Nov. 24, 1988). (4 pages).
*Proceedings Clinical Dialysis and Transplant Forum*, (vol. 10), (apparently unauthored) (1980). (7 pages).
*The O-Cath R/M Recording and Monitoring System*, published by the Journal of the American College of Cardiology, (vol. 13, No. 7), (Jun. 1989). (2 pages).
*Seratronics, Inc. DRS 4 D/ND Dialyzer Reprocessing System Operators Manual*, published by Seratronics, Inc., (apparently undated). (94 pages).
*Seratronics, Inc. DRS 4 D/ND Dialyzer Reprocessing System Technical Manual*, published by Seratronics, Inc., (apparently undated). (456 pages).
*Serum Sodium Concentration and Body Fluid Distribution During Interdialysis: Importance of Sodium to Fluid Intake Ratio in Hemodialysis Patient*, The International Journal of Artificial Organs (vol. 7 No. 6), G. Kimura et al., (1984). (6 pages).
*Telecontrol of Domestic Dialysis: Programmes and Prospects* (abstract in English), published by CSELT Rapporti Tecnici (vol. 8, No. 4), (Dec. 1980). pp. 187-194. (1 page).
*The Thirteenth Annual Symposium on Computer Applications in Medical Care*, published by The Institute of Electrical and Electronics Engineers Inc. (Nov. 1989). (6 pages).
*Touch Panels Point the Way to Natural Data Entry*, published by Electronic Design (May 28, 1987). (6 pages).
*Tried & True Bicardonate*, Drake Willock, (1978). (1 page).
*User Guidance Strategies for the Visual Interface with Virtual Control Elements* (redacted), 1982 International Zurich Seminar on Digital Communications Proceedings, published by Helmholtz-Institut für Biomedizinische Technik, (apparently undated). (6 pages).
Veolar Intensive Care Ventilation, published in Respiratory Care, (vol. 34, No. 6), (Jun. 1989). (2 pages).
What Matters in Hemodialysis Equipment, Therapy Assessment, Identify Impediments to Effective Clearance, published by Fresenius Medical Care (2000). (2 pages).
What Matters in Hemodialysis Equipment, Therapy Assessment, Thermal Hypotension Management, Access Recirculation, published by Fresenius Medical Care (2000). (2 pages).
Picture of 2550 machine, Baxter, (apparently undated). (1 page).
Proceedings from opposition to European Patent EP 0 597 817 B1. (296 pages), undated.
Proceedings from opposition to European Patent EP 0 688 793. (169 pages), undated.
Documents from the prosecution file for Canadian Patent Application No. 2,349,809. (30 pages), undated.
English translation of abstract for JP Patent No. 54-153781 entitled "Blood Dialyser for Artificial Kidney -Allowing Automatic Sterilisation and Cleaning After Completion and Before Start of Dialysis.", undated.
G. Rau: Man-Machine Communication for Monitoring, Recording and Decision Support in an Anesthesia Information System (AIS) Hemholtz-Institute for Biomedical Engineering Aachen, FRG p. (apparently undated).
Trispel (Rau): Towards a Coherent Structure of the Anesthetist computer interface, 1985.
J.W. Austin, et al.: The Heart-Lung Machine & Related Technologies of Open Heart Surgery (1990).
S. Sherr: Input Devices (1988).
J.S. Gravenstein, et al.: The Automated Anesthesia Record and Alarm Systems (1987) Record and Alarm Systems (1987).
Althin CD Medical, Inc., reporting of: Applications: Dialysis Machine Sep./Oct. 1991, Plastic Design, Forum, p. 72, 4008 Profile Display.
H. Popp, et al.: An Interactive, Computer-Based Obv Simulator of the Cardio- Vascular System as a Tool for [all], Knowledge Acquisition in Cardio Anesthesia, Helmholtz-Institut Aachem Research Report p. 153-159 (1989/90).
J.C. Van Stone, et al.: The Effect of Dialysate Sodium Concentration on Body Fluid Distribution during [all] Hemodialysis, Trans American Society on Artificial Intern. Organs (1980).
G.E. Fleig: Optimizing Dialysis Using Sodium-Volume Obv Modeling, Cordis Dow Research, Concord, CA (1982).
T. Roy, et al.: Volumetrically Controlled Ultrafiltration. Current experiences and future trends, International Journal of Artificial Organs, vol. 6, No. 3, pp. 131-135 (1982) (UF Profiling).
R. Raja, et al.: Sequential changes in Dialysate Sodium (DN0) During Hemodialysis, Trans American Society on Artificial Intern. Organs (1983).
J Kline, Figure 2: Treatment Results with High and Low Sodium (Qellhorst, 1980 EDTA) Biological Foundations of Biomedical Engineering, pp. 409-410 (1978 ed.).
King, et al.: Computer Optimization of Hemodialysis, vol. XIV Trans. Amer. Soc. Artif. Int. Organs, pp. 389-393 (1968).
King, et al.: An IBM AT based monitoring system with touchscreen input, Intl Journal of Clinical Monitoring and Computing 7: 107-111 (1990).
King, et al.: Computerized Monitoring at Vanderbilt University Status and Future Directions, Intl Journal of Clinical Monitoring and Computing 8: 117-120 (1991).
King, et al.: Automated Record-Keeping Systems Used in Anesthesia, vol. X, No. 3 Hospimedica, pp. 34-39 (Apr. 1992).
King, et al.: A Functioning Semi Automated Monitoring and Record Keeping System, Vanderbilt University. (apparently undated).
King, et al.: A Semi Automated Operating Room Monitoring System Using an IBM PC/XT, Dept. of Anesthesiology, Vanderbilt University. (apparently undated).
P. King: A Study of Engineering Optimization of hemodialysis, Dissertation (1968).

G. Salvendy ed.: Handbook of Human Factors: Human Factors Aspects of Manual Computer Input Devices, Wiley-Interscience Pub., Ch. 11.4. (1987).
J. Logan: Touch Screens Diversify, Electronic Products (Nov. 1985).
M. Valk: An Experiment to Study Touchscreen "Button" Design, Proc. of the Human Factors Society 29th Annual Meeting vol. 1 (1985).
"A Menu-driven, Touch Panel Microcomputer for Clinical Recordkeeping," William J. Schenker, M.D., Medical Instrumentation, vol. 14, No. 6, Nov.-Dec. 1980.
Karat, et al.: A Comparison of Selection Techniques: Touch Panel, Mouse and Keyboard, Human-Computer Interaction—Interact (1984).
Weiss, et al.: Information System Designed with Users and Operating Rooms in Mind, Medical Device & Diagnostic Industry, pp. 68; 70-71 (1989).
Impuls Sistema de Dialisis. (apparently undated).
Dialyse-System DS 701. (apparently undated).
Dialsegerat mp 100 . . . Therapieformen. (apparently undated).
Silvern: Ventilator Risk Management, 1989.
Sep. 3, 1986 Document entitled "2008 Terminal Meeting with Dr. Gold."
Aug. 31, 1986 Document entitled "2008 Add on Computer Proposal."
Dec. 21, 1989 Peterson to Lipps, et al., Memo re: FDS-08.
May 15, 1991 Peterson to Lipps, et al., Memo re: Product Definition for Bedside Screen (DITS).
Pacesetter Manual APS II, undated.
3M Sarns Perfusion System 9000, undated.
3M Sarns Perfusion System 9000 Operators Manual (1987).
3M Sarns Perfusion System 9000 Operators Manual Subsequent Edition, undated.
Trispel et al., User Guidance in Interactive Systems—the Role of Graphical Features, undated.
Middo et al., Touch Panels Point The Way To Natural Data Entry, undated.
Photo of Pacesetter Analyzer Programmer System, undated.
Photo of Pacesetter Analyzer Programmer System machine model 283 (1997) with screen AFP indicated.
Photo of Pacesetter Analyzer Programmer System machine model 283 (1997) with screen Surface ECG indicated.
Website: www.system-medical.de/produkte/sax.htm, undated.
Knowledge-Based Decision Support in Anesthesia: A Case Study © 1988 IEEE, Th. Shecke et al.
A Technological Assessment of the Current and Future Status of Hemodialysis, Prakash R. Keshaviah, PhD., Medical Instrumentation, vol. 20, No. 2, Mar.-Apr. 1986.
Interactive Hemodialysis Control System for Improved Cardiovascular Stability, Elias Klein, PhD, and Ronald L. Wathen, MD, PhD., Medical Instrumentation, vol. 20, No. 2, Mar.-Apr. 1986.
Intraoperative hemodialysis during cardiopulmonary bypass in chronic renal failure, O. Soffer et al., Journal of Thoracic and Cardiovascular Surgery, vol. 77, No. 5, May 1979.
Computer Control of Anesthesia Delivery, Dwayne R. Westenskow, PhD., William S. Jordan, M.D., John K. Hayes, M.S., Thomas D. East, PhD., Computing in Anesthesia and Intensive Care, pp. 270-278. (apparently undated).
An Expert Alarm System, Ch. 19 of Automated Anesthesia Record and Alarm, Yasuhiro Fukui. (apparently undated).
The Acute Dialysis Quality Initiative (ADQI), Dialysis Times, p. 7. (apparently undated).
AK 200 S, AK 200 Ultra S Dialysis Machines Brochure. Published by Gambro. (apparently undated).
Clearance and Ultrafiltration of Reused Dialyzers, F.A. Gotch, Panel Conference—Dialyzer Reuse, pp. 717-718. (apparently undated).
Dialog® Operating Instructions, © B. Braun Medical Inc., B. Braun Renal Therapies Division, Bethlehem, PA.
J3E—Dialogue Homme-Machine, Dialysis Times Nov. 12, 1990.
BTM Control, Dialysis Times, Renal Research Institute, LLC, p. 3 (apparently undated).

What's New? Job Opportunities, Dialysis Times, p. 8 (apparently undated).

A New Generation with New Standards for Safety Performance (redacted), Dylade Series, The Dylade Company Limited, Runcorn, Cheshire, England WA7 1PQ (apparently undated).

Fight evil hypotensive episodes and undetected edemas with Hemavision™, ANNA Journal, vol. 25, No. 5, Oct. 1998.

High clearance continuous renal replacement therapy with a modified dialysis machine, Kidney International, vol. 56, Suppl. 72 (1999), pp. S-20-S-23, © 1999 by the International Society of Nephrology.

MD2 & MD3: Floppy Disk Micro Decision, brochure, Morrow, San Leandro, CA 94577. (apparently undated).

Measurement of Blood Access Flow Rate During Hemodialysis from Conductivity Dialysance, © Gotch, et al., American Society for Artificial Internal Organs, Inc., ASAIO Journal, May-Jun. 1999, vol. 45, No. 3.

The Morrow Network brochure, San Leandro, CA 94577. (apparently undated).

The MorrowWriter brochure, published by Morrow, San Leandro, CA 94577. (apparently undated).

CRRT with the 2008H, Procedures to establish a Continuous Renal Replacement Therapy (CRRT) program in an Intensive Care Unit (ICU) © Fresenius USA. (apparently undated).

Seratron Dialysis Control System, Modeling Programer Manual, Cordis Dow Corp.™ Trademark of Cordis Dow Corp., Concord, CA. (apparently undated).

Seratronics DPS 4™ Dialyzer Preparation System brochure, Seratronics, Inc., Concord, CA 94520, undated.

Easy to use, cost effective equipment for dialyzer reprocessing based on proven reuse techniques that provide a safe environment for staff and improved patient care, brochure, Seratronics, Concord CA 94520. (apparently undated).

Seratronics DRS-4™ brochure. (apparently undated).

Seratronics DRS-4™ Dialyzer Reprocessing System brochure. (apparently undated).

Simply Touch the Screen for Automatic Treatment Control, The Drake Willock System 1000 brochure. (apparently undated).

TransTerm 7, Battery Powered, Portable Data Collection Terminal brochure, Computerwise®, Inc. (apparently undated).

TransTerm 7B User's Manual, Computerwise®, Inc. (apparently undated).

TransTerm 7B User's Manual, Copyright 1988 (All Rights Reserved), Computerwise®, Inc.

Renal-Stat User Manual, Armament Systems, Inc., Anaheim, CA 92801. (apparently undated).

Ultrafiltration Control Manul, Cordis Dow Corp., Miami, FL. (apparently undated).

Ultrafiltration Monitor UFM 10-2 Service manual. (apparently undated).

The (Wind) Chill Factor Controlled, Editorial © 2002 by the National Kidney Foundation, Inc., American Journal of Kidney Diseases, vol. 40, No. 2 (Aug. 2002); pp. 426-428.

*Fresenius Medical Care Holdings, Inc.* v. *Baxter International Inc. and Baxter Healthcare Corporation*, Fresenius' Initial Disclosures, undated.

*Fresenius Medical Care Holdings, Inc.* v. *Baxter International Inc. and Baxter Healthcare Corporation*, Fresenius Medical Care Holdings, Inc.'s and Fresenius USA, Inc.'s Preliminary Invalidity Contentions Pursuant to Patent L.R. 3-3, undated.

*Fresenius Medical Care Holdings, Inc.* v. *Baxter International Inc. and Baxter Healthcare Corporation*, Fresenius' Objections and Responses to Baxter's First Set of Interrogatories (Nos. 1-13).

*Fresenius Medical Care Holdings, Inc.* v. *Baxter International Inc. and Baxter Healthcare Corporation*, Fresenius' Supplemental Responses to Baxter's First Set of Interrogatories (Nos. 5, 6, 9, and 13).

*Fresenius Medical Care Holdings, Inc.* v. *Baxter International Inc. and Baxter Healthcare Corporation*, Order Regarding Supplemental Claim Construction Entered by Judge Armstrong.

*Fresenius Medical Care Holdings, Inc.* v. *Baxter International Inc. and Baxter Healthcare Corporation*, Fresenius' Opposition to Baxter's Motion for Partial Summary Judgment of Literal Infringement; Cross-Motion for Summary Judgment of Non-Infringement.

*Fresenius Medical Care Holdings, Inc.* v. *Baxter International Inc. and Baxter Healthcare Corporation*, Declaration of Richard A. Ward, Ph.D.

*Fresenius Medical Care Holdings, Inc.* v. *Baxter International Inc. and Baxter Healthcare Corporation*, Exhibit A to Declaration of Richard A. Ward, Ph.D.—Copy of Paper that Emerged from Collaboration with National Institutes of Health.

*Fresenius Medical Care Holdings, Inc.* v. *Baxter International Inc. and Baxter Healthcare Corporation*, Exhibit B to Declaration of Richard A. Ward, Ph.D.—*Curriculum Vitae* Of Richard A. Ward, Ph.D.

*Fresenius Medical Care Holdings, Inc.* v. *Baxter International Inc. and Baxter Healthcare Corporation*, Declaration of Martin Crnkovich.

*Fresenius Medical Care Holdings, Inc.* v. *Baxter International Inc. and Baxter Healthcare Corporation*, Exhibit A to Declaration of Martin Crnkovich—Excerpts from the Seratron Modeling Programmer Operator's Manual.

*Fresenius Medical Care Holdings, Inc.* v. *Baxter International Inc. and Baxter Healthcare Corporation*, Exhibit B to Declaration of Martin Crnkovich—Excerpts from the English Translation of the 1988 CMS-08 Operator's Manual.

*Fresenius Medical Care Holdings, Inc.* v. *Baxter International Inc. and Baxter Healthcare Corporation*, Exhibit C to Declaration of Martin Crnkovich—"Screen Shot" of a UF Profiling Screen on the Accused Fresenius 2008K Hemodialysis System.

*Fresenius Medical Care Holdings, Inc.* v. *Baxter International Inc. and Baxter Healthcare Corporation*, Exhibit D to Declaration of Martin Crnkovich—Excerpts from the Braun HD-Secura Manual.

*Fresenius Medical Care Holdings, Inc.* v. *Baxter International Inc. and Baxter Healthcare Corporation*, Exhibit E to Declaration of Martin Crnkovich—Enlarged Shot of"Dialysis Paused" Screen Shot.

*Fresenius Medical Care Holdings, Inc.* v. *Baxter International Inc. and Baxter Healthcare Corporation*, Exhibit F to Declaration of Martin Crnkovich—Enlarged Copies of Two UF Programs (Nos. 5 and 6) Screen Shots.

*Fresenius Medical Care Holdings, Inc.* v. *Baxter International Inc. and Baxter Healthcare Corporation*, Exhibit G to Declaration of Martin Crnkovich—Enlarged Copies of Photographs of 2008D Front Panel and 2008E Front Panel.

*Fresenius Medical Care Holdings, Inc.* v. *Baxter International Inc. and Baxter Healthcare Corporation*, Exhibit H to Declaration of Martin Crnkovich—Copy of Excerpts from the Cobe Century 3 Operator's Manual.

*Fresenius Medical Care Holdings, Inc.* v. *Baxter International Inc. and Baxter Healthcare Corporation*, Exhibit I to Declaration of Martin Crnkovich—Enlarged Copies of SVS Programming Screen Shots.

*Fresenius Medical Care Holdings, Inc.* v. *Baxter International Inc. and Baxter Healthcare Corporation*, Exhibit J to Declaration of Martin Crnkovich—Manual for the Fresenius BPS-08 Device.

*Fresenius Medical Care Holdings, Inc.* v. *Baxter International Inc. and Baxter Healthcare Corporation*, Declaration of David J. Silbert.

*Fresenius Medical Care Holdings, Inc.* v. *Baxter International Inc. and Baxter Healthcare Corporation*, Exhibit 1 to Declaration of David J. Silbert—Office Actions Dated Nov. 24, 1998, Jun. 4, 1999 and Oct. 20, 1999 in U.S. Appl. No. 09/067,922.

*Fresenius Medical Care Holdings, Inc.* v. *Baxter International Inc. and Baxter Healthcare Corporation*, Exhibit 2 to Declaration of David J. Silbert—Decision of the Board of Patent Appeals and Interferences Dated Aug. 28, 2003.

*Fresenius Medical Care Holdings, Inc.* v. *Baxter International Inc. and Baxter Healthcare Corporation*, Exhibit 3 to Declaration of David J. Silbert—Excerpts from the Deposition of Thomas D. Kelly.

*Fresenius Medical Care Holdings, Inc.* v. *Baxter International Inc. and Baxter Healthcare Corporation*, Exhibit 4 to Declaration of David J. Silbert—Office Action Dated Sep. 22, 1992 from U.S. Appl. No. 07/688,174.

*Fresenius Medical Care Holdings, Inc.* v. *Baxter International Inc. and Baxter Healthcare Corporation*, Exhibit 5 to Declaration of David J. Silbert—Kerns Patent.
*Fresenius Medical Care Holdings, Inc.* v. *Baxter International Inc. and Baxter Healthcare Corporation*, Exhibit 6 to Declaration of David J. Silbert—Non-Color Copy of a Screen Shot of the "SVS Screen" on the Accused Fresenius 2008K Machine.
*Fresenius Medical Care Holdings, Inc.* v. *Baxter International Inc. and Baxter Healthcare Corporation*, Exhibit 7 to Declaration of David J. Silbert—Non-Color Copy of a Screen Shot of the "Kt/V Screen" on the Accused Fresenius 2008K Machine.
*Fresenius Medical Care Holdings, Inc.* v. *Baxter International Inc. and Baxter Healthcare Corporation*, Exhibit 8 to Declaration of David J. Silbert—Excerpts from Baxter's Final Infringement Contentions Relating to Its Contentions That Fresenius Infringes the '131 and '434 Patents.
*Fresenius Medical Care Holdings, Inc.* v. *Baxter International Inc. and Baxter Healthcare Corporation*, Fresenius' Reply in Support of Cross-Motion for Summary Judgment of Non-Infringement.
*Fresenius Medical Care Holdings, Inc.* v. *Baxter International Inc. and Baxter Healthcare Corporation*, Reply Declaration of David J. Silbert.
*Fresenius Medical Care Holdings, Inc.* v. *Baxter International Inc. and Baxter Healthcare Corporation*, Exhibit A to Supplemental Declaration of David J. Silbert—Excerpts From Baxter's Final Infringement Contentions ("Baxter FIC") Relating to Its Contentions That Fresenius Infringes the '131 and '434 Patents.
*Fresenius Medical Care Holdings, Inc.* v. *Baxter International Inc. and Baxter Healthcare Corporation*, Exhibit B to Supplemental Declaration of David J. Silbert—Excerpts From Four Different Versions of Baxter's Preliminary Infringement Contentions Relating to Its Contentions That Fresenius Infringes the '131 and '434 Patents.
*Fresenius Medical Care Holdings, Inc.* v. *Baxter International Inc. and Baxter Healthcare Corporation*, Exhibit C to Supplemental Declaration of David J. Silbert—Baxter's Responses to Fresenius Second Set of Interrogatories, Served on Dec. 22, 2004.
*Fresenius Medical Care Holdings, Inc.* v. *Baxter International Inc. and Baxter Healthcare Corporation*, Exhibit D to Supplemental Declaration of David J. Silbert—Excerpts from the Deposition of Martin Crnkovich.
*Fresenius Medical Care Holdings, Inc.* v. *Baxter International Inc. and Baxter Healthcare Corporation*, Exhibit E to Supplemental Declaration of David J. Silbert—Excerpts from the Deposition of Dr. Richard A. Ward.
*Fresenius Medical Care Holdings, Inc.* v. *Baxter International Inc. and Baxter Healthcare Corporation*, Exhibit F to Supplemental Declaration of David J. Silbert—Excerpt from the McGraw Hill Dictionary of Scientific and Technical Terms (Fifth Edition).
*Fresenius Medical Care Holdings, Inc.* v. *Baxter International Inc. and Baxter Healthcare Corporation*, Exhibit G to Supplemental Declaration of David J. Silbert—Order Granting in Part and Denying in Part Motion to Compel Supplemental Disclosures Pursuant to Patent Local Rules 3-1, Entered on Feb. 4, 2004.
*Fresenius Medical Care Holdings, Inc.* v. *Baxter International Inc. and Baxter Healthcare Corporation*, Exhibit H to Supplemental Declaration of David J. Silbert—Screen Shot of the "Home" Screen on the Accused 2008K Hemodialysis Machine.
*Fresenius USA, Inc.* v. *Baxter International Inc. and Baxter Healthcare Corporation*, Baxter's Initial Disclosures Under Fed. R. Civ. P. 26(a)(1).
*Fresenius USA, Inc.* v. *Baxter International Inc. and Baxter Healthcare Corporation*, Defendants' Reponses to Plaintiffs' First Set of Interrogatories (Nos. 1-7).
*Fresenius USA, Inc.* v. *Baxter International Inc. and Baxter Healthcare Corporation*, Defendants' Motion for Partial Summary Judgment of Infringement.
*Fresenius USA, Inc.* v. *Baxter International Inc. and Baxter Healthcare Corporation*, Declaration of Michael J. Abernathy in Support of Defendants' Motion for Partial Summary Judgment of Infringement.
*Fresenius USA, Inc.* v. *Baxter International Inc. and Baxter Healthcare Corporation*, Exhibit DX 14 to Declaration of Michael J. Abernathy in Support of Defendants' Motion for Partial Summary Judgment of Infringement—Pages from Webster's Ninth New Collegiate Dictionary (1984).
*Fresenius USA, Inc.* v. *Baxter International Inc. and Baxter Healthcare Corporation*, Exhibit DX 15 to Declaration of Michael J. Abernathy in Support of Defendants' Motion for Partial Summary Judgment of Infringement—Fresenius' Second Supplemental Response to Interrogatory Nos. 5 and 13 Dated Nov. 23, 2004.
*Fresenius USA, Inc.* v. *Baxter International Inc. and Baxter Healthcare Corporation*, Exhibit DX 16 to Declaration of Michael J. Abernathy in Support of Defendants' Motion for Partial Summary Judgment of Infringement—Claim Construction Order Dated Nov. 22, 2004.
*Fresenius USA, Inc.* v. *Baxter International Inc. and Baxter Healthcare Corporation*, Exhibit DX 17 to Declaration of Michael J. Abernathy in Support of Defendants' Motion for Partial Summary Judgment of Infringement—Joint Request For Supplemental Claim Construction Hearing and Joint Supplemental Claim Construction Statement Pursuant To Patent Local Rule 4-3 Dated Dec. 22, 2004.
*Fresenius USA, Inc.* v. *Baxter International Inc. and Baxter Healthcare Corporation*, Exhibit DX 18 to Declaration of Michael J. Abernathy in Support of Defendants' Motion for Partial Summary Judgment of Infringement—Supplemental Joint Claim Construction and Prehearing Statement Under Patent Local Rule 4-3 Dated Aug. 17, 2004.
*Fresenius USA, Inc.* v. *Baxter International Inc. and Baxter Healthcare Corporation*, Exhibit DX 19 to Declaration of Michael J. Abernathy in Support of Defendants' Motion for Partial Summary Judgment of Infringement—Joint Claim Construction and Prehearing Statement Under Patent Local Rule 4-3 Dated Jan. 26, 2004.
*Fresenius USA, Inc.* v. *Baxter International Inc. and Baxter Healthcare Corporation*, Exhibit DX 20 to Declaration of Michael J. Abernathy in Support of Defendants' Motion for Partial Summary Judgment of Infringement—Defendants/Counter-Plaintiffs' Supplemental Claim Construction Brief Dated Aug. 31, 2004.
*Fresenius USA, Inc.* v. *Baxter International Inc. and Baxter Healthcare Corporation*, Exhibit DX 21 to Declaration of Michael J. Abernathy in Support of Defendants' Motion for Partial Summary Judgment of Infringement—Plaintiffs' Responsive Claim Construction Brief Dated Mar. 22, 2004.
*Fresenius USA, Inc.* v. *Baxter International Inc. and Baxter Healthcare Corporation*, Exhibit DX 22 to Declaration of Michael J. Abernathy in Support of Defendants' Motion for Partial Summary Judgment of Infringement—Joint Case Management Conference Statement and [Proposed] Order Dated Jul. 5, 2004.
*Fresenius USA, Inc.* v. *Baxter International Inc. and Baxter Healthcare Corporation*, Declaration of Thomas D. Kelly in Support of Defendants' Motion for Partial Summary Judgment of Infringement.
*Fresenius USA, Inc.* v. *Baxter International Inc. and Baxter Healthcare Corporation*, Exhibit DX 1 to Declaration of Thomas D. Kelly in Support of Defendants' Motion for Partial Summary Judgment of Infringement—Fresenius USA 2008K Hemodialysis Machine Operator's Manual.
*Fresenius USA, Inc.* v. *Baxter International Inc. and Baxter Healthcare Corporation*, Exhibit DX 2 to Declaration of Thomas D. Kelly in Support of Defendants' Motion for Partial Summary Judgment of Infringement—Fresenius USA 2008K Hemodialysis System Technician's Manual for the Fresenius 2008K Machine.
*Fresenius USA, Inc.* v. *Baxter International Inc. and Baxter Healthcare Corporation*, Exhibit DX 3 to Declaration of Thomas D. Kelly in Support of Defendants' Motion for Partial Summary Judgment of Infringement—User/Machine Interface for the Fresenius 2008K Machine, Including the Touch Screen in the Center of the Interface, a Numeric Keypad Below the Touch Screen, Up and Down Keys to the Left of the Keypad, and a "CONFIRM" Button to the Right of the Keypad.
*Fresenius USA, Inc.* v. *Baxter International Inc. and Baxter Healthcare Corporation*, Exhibit DX 4 to Declaration of Thomas D. Kelly in Support of Defendants' Motion for Partial Summary Judgment of Infringement—Home Screen of the Fresenius 2008K Touch Screen.

*Fresenius USA, Inc. v. Baxter International Inc. and Baxter Healthcare Corporation*, Exhibit DX 4A to Declaration of Thomas D. Kelly in Support of Defendants' Motion for Partial Summary Judgment of Infringement—Copy of DX 4 in Which the Operational Parameter and Subscreen Buttons Have Been Highlighted for Demonstrative Purposes.

*Fresenius USA, Inc. v. Baxter International Inc. and Baxter Healthcare Corporation*, Exhibit DX 4B to Declaration of Thomas D. Kelly in Support of Defendants' Motion for Partial Summary Judgment of Infringement—Copy of DX 4 in Which the "Temperature" Button Has Been Highlighted for Demonstrative Purposes.

*Fresenius USA, Inc. v. Baxter International Inc. and Baxter Healthcare Corporation*, Exhibit DX 4C to Declaration of Thomas D. Kelly in Support of Defendants' Motion for Partial Summary Judgment of Infringement—Copy of DX 4 in Which the "Dialysate Flow" Button Has Been Highlighted for Demonstrative Purposes.

*Fresenius USA, Inc. v. Baxter International Inc. and Baxter Healthcare Corporation*, Exhibit DX 4D to Declaration of Thomas D. Kelly in Support of Defendants' Motion for Partial Summary Judgment of Infringement—Copy of DX 4 in Which the "Conductivity" Button Has Been Highlighted for Demonstrative Purposes.

*Fresenius USA, Inc. v. Baxter International Inc. and Baxter Healthcare Corporation*, Exhibit DX 4E to Declaration of Thomas D. Kelly in Support of Defendants' Motion for Partial Summary Judgment of Infringement—Copy of DX 4 in Which the "UF Goal," "UF Time" and "UF Profile" Buttons Have Been Highlighted for Demonstrative Purposes.

*Fresenius USA, Inc. v. Baxter International Inc. and Baxter Healthcare Corporation*, Exhibit DX 4F to Declaration of Thomas D. Kelly in Support of Defendants' Motion for Partial Summary Judgment of Infringement—Copy of DX 4 in Which the "UF Rate" Button Has Been Highlighted for Demonstrative Purposes.

*Fresenius USA, Inc. v. Baxter International Inc. and Baxter Healthcare Corporation*, Exhibit DX 5 to Declaration of Thomas D. Kelly in Support of Defendants' Motion for Partial Summary Judgment of Infringement—the Next in the Series of Shots Including DX4 that Fairly and Accurately Shows the "Home" Screen of the Fresenius 2008K Touch Screen While the Machine Was Performing an Ultrafiltration Profile. The "UF Goal" is still set to 3000 mL. The "UF time," however, Has Now Diminished to 2 hours and 45 minutes.

*Fresenius USA, Inc. v. Baxter International Inc. and Baxter Healthcare Corporation*, Exhibit DX 6 to Declaration of Thomas D. Kelly in Support of Defendants' Motion for Partial Summary Judgment of Infringement—the "UF Profile" Subscreen of the Fresenius 2008K Touch Screen.

*Fresenius USA, Inc. v. Baxter International Inc. and Baxter Healthcare Corporation*, Exhibit DX 6A to Declaration of Thomas D. Kelly in Support of Defendants' Motion for Partial Summary Judgment of Infringement—Copy of DX6 in Which the "UF Goal" and "UF Time" Buttons Have Been Highlighted for Demonstrative Purposes.

*Fresenius USA, Inc. v. Baxter International Inc. and Baxter Healthcare Corporation*, Exhibit DX 6B to Declaration of Thomas D. Kelly in Support of Defendants' Motion for Partial Summary Judgment of Infringement—Copy of DX 6 in Which the Nine Buttons that Graphically Represent the Prescribed Manner in Which Ultrafiltration Will Be Carried Out Have Been Highlighted for Demonstrative Purposes.

*Fresenius USA, Inc. v. Baxter International Inc. and Baxter Healthcare Corporation*, Exhibit DX 6C to Declaration of Thomas D. Kelly in Support of Defendants' Motion for Partial Summary Judgment of Infringement—Copy of DX 6 in Which the Enlarged Display of the Selected Profile Has Been Highlighted for Demonstrative Purposes.

*Fresenius USA, Inc. v. Baxter International Inc. and Baxter Healthcare Corporation*, Exhibit DX 6D to Declaration of Thomas D. Kelly in Support of Defendants' Motion for Partial Summary Judgment of Infringement—Copy of DX 6 in Which the "Maximum UF Rate" Display Has Been Highlighted for Demonstrative Purposes.

*Fresenius USA, Inc. v. Baxter International Inc. and Baxter Healthcare Corporation*, Exhibit DX 6E to Declaration of Thomas D. Kelly in Support of Defendants' Motion for Partial Summary Judgment of Infringement—Copy of DX 6 in Which the Button Displaying the Selected Profile Graphically Has Been Highlighted for Demonstrative Purposes.

*Fresenius USA, Inc. v. Baxter International Inc. and Baxter Healthcare Corporation*, Exhibit DX 7 to Declaration of Thomas D. Kelly in Support of Defendants' Motion for Partial Summary Judgment of Infringement—"UF Profile" Subscreen of the Fresenius 2008K Touch Screen.

*Fresenius USA, Inc. v. Baxter International Inc. and Baxter Healthcare Corporation*, Exhibit DX 7A to Declaration of Thomas D. Kelly in Support of Defendants' Motion for Partial Summary Judgment of Infringement—Copy of DX 7 in Which the "UF Goal" and "Maximum UF Rate" Displays Have Been Highlighted for Demonstrative Purposes.

*Fresenius USA, Inc. v. Baxter International Inc. and Baxter Healthcare Corporation*, Exhibit DX 8 to Declaration of Thomas D. Kelly in Support of Defendants' Motion for Partial Summary Judgment of Infringement—Subscreen Used for Creating Customized UF Profiles in the Fresenius 2008K.

*Fresenius USA, Inc. v. Baxter International Inc. and Baxter Healthcare Corporation*, Exhibit DX 9 to Declaration of Thomas D. Kelly in Support of Defendants' Motion for Partial Summary Judgment of Infringement—"Dialysate" Subscreen of the Fresenius 2008K Touch Screen.

*Fresenius USA, Inc. v. Baxter International Inc. and Baxter Healthcare Corporation*, Exhibit DX 9A to Declaration of Thomas D. Kelly in Support of Defendants' Motion for Partial Summary Judgment of Infringement—Buttons Highlighted for Demonstrative Purposes in a Copy of DX 9.

*Fresenius USA, Inc. v. Baxter International Inc. and Baxter Healthcare Corporation*, Exhibit DX 10 to Declaration of Thomas D. Kelly in Support of Defendants' Motion for Partial Summary Judgment of Infringement—the Deaeration Pump Located Within the Fresenius 2008K Machine.

*Fresenius USA, Inc. v. Baxter International Inc. and Baxter Healthcare Corporation*, Exhibit DX 10A to Declaration of Thomas D. Kelly in Support of Defendants' Motion for Partial Summary Judgment of Infringement—Pump Highlighted for Demonstrative Purposes in a Copy of DX 10.

*Fresenius USA, Inc. v. Baxter International Inc. and Baxter Healthcare Corporation*, Exhibit DX 11 to Declaration of Thomas D. Kelly in Support of Defendants' Motion for Partial Summary Judgment of Infringement—Concentrate Pumps Located Within the Fresenius 2008K Machine.

*Fresenius USA, Inc. v. Baxter International Inc. and Baxter Healthcare Corporation*, Exhibit DX 11A to Declaration of Thomas D. Kelly in Support of Defendants' Motion for Partial Summary Judgment of Infringement—Pumps Highlighted for Demonstrative Purposes in a Copy of DX 11.

*Fresenius USA, Inc. v. Baxter International Inc. and Baxter Healthcare Corporation*, Exhibit DX 12 to Declaration of Thomas D. Kelly in Support of Defendants' Motion for Partial Summary Judgment of Infringement—UF Pump Located Within the Fresenius 2008K Machine.

*Fresenius USA, Inc. v. Baxter International Inc. and Baxter Healthcare Corporation*, Exhibit DX 12A to Declaration of Thomas D. Kelly in Support of Defendants' Motion for Partial Summary Judgment of Infringement—Pump highlighted for Demonstrative Purposes in a Copy of DX 12.

*Fresenius USA, Inc. v. Baxter International Inc. and Baxter Healthcare Corporation*, Exhibit DX 13 to Declaration of Thomas D. Kelly in Support of Defendants' Motion for Partial Summary Judgment of Infringement—Circuit Board Containing a Microprocessor Located Within the Fresenius 2008K Machine.

*Fresenius USA, Inc. v. Baxter International Inc. and Baxter Healthcare Corporation*, Defendants' Reply in Support of Their Motion for Partial Summary Judgment of Infringement and Opposition to Plaintiffs' Cross-Motion.

*Fresenius USA, Inc. v. Baxter International Inc. and Baxter Healthcare Corporation*, Supplemental Declaration of Michael J. Abernathy in Support of Defendants' Reply in Support of Their Motion for Partial Summary Judgment of Infringement and Opposition to Plaintiffs' Cross-Motion.
*Fresenius USA, Inc.* v. *Baxter International Inc. and Baxter Healthcare Corporation*, Exhibit DX 18 to Supplemental Declaration of Michael J. Abernathy in Support of Defendants' Reply in Support of Their Motion for Partial Summary Judgment of Infringement and Opposition to Plaintiffs' Cross-Motion—Advanced Power Technology's Notice of Motion and Motion for Leave to Amend Its Final Invalidity Contentions from *IXYS Corp.* v. *Advance Power Technology Inc.*, No. C-02-3942 MHP (N.D.Cal.).
*Fresenius USA, Inc.* v. *Baxter International Inc. and Baxter Healthcare Corporation*, Exhibit DX 19 to Supplemental Declaration of Michael J. Abernathy in Support of Defendants' Reply in Support of Their Motion for Partial Summary Judgment of Infringement and Opposition to Plaintiffs' Cross-Motion—Reply in Support of Advanced Power Technology's, Inc.'s Motion for Leave to Amend Its Final Invalidity Contentions from *IXYS Corp.* v. *Advance Power Technology Inc.*, No. C-02-3942 MHP (N.D. Cal.).
*Fresenius USA, Inc.* v. *Baxter International Inc. and Baxter Healthcare Corporation*, Exhibit DX 20 to Supplemental Declaration of Michael J. Abernathy in Support of Defendants' Reply in Support of Their Motion for Partial Summary Judgment of Infringement and Opposition to Plaintiffs' Cross-Motion—Slip Opinion dated Feb. 26, 2004 from *Immersion Corp.* v. *Sony Computer Entertainment Amer. Inc.*, No. C-02-710 CW (WDB) (N.D. Cal.) (Brazil, Mag.J.).
*Fresenius USA, Inc.* v. *Baxter International Inc. and Baxter Healthcare Corporation*, Exhibit DX 21 to Supplemental Declaration of Michael J. Abernathy in Support of Defendants' Reply in Support of Their Motion for Partial Summary Judgment of Infringement and Opposition to Plaintiffs' Cross-Motion—Email Received by Michael Abernathy from Stuart Gasner Dated Dec. 16, 2004.
*Fresenius USA, Inc.* v. *Baxter International Inc. and Baxter Healthcare Corporation*, Exhibit DX 22 to Supplemental Declaration of Michael J. Abernathy in Support of Defendants' Reply in Support of Their Motion for Partial Summary Judgment of Infringement and Opposition to Plaintiffs' Cross-Motion—Letter Dated Feb. 20, 2003 from Joseph P. Reagen to Thomas J. Raubauch.
"A World of EMI Solutions for Complex Shielding Demands" brochure, Schlegel Corporation, 1994.
"Abstracts from the Second International Symposium on Modeling in Artificial Kidney and Plasma Exchange," Artif. Organs, vol. 8, No. 1, 1984, pp. 116-123.
"Apple Lisa" printed from http://oldcomputers.net (p. 1 of 4); printed on Jan. 18, 2005.
"Cardiac Surgery in Hemodialysis Patients" printed from www.ncbi.nlm.nih.gov printed Feb. 16, 2005.
"dti TechnAlert," Journal of Medical Engineering & Technology, vol. 13, No. 3 (May/Jun. 1989), pp. 204-205.
"Evaluation Report: Dialysis Equipment," Journal of Medical Engineering & Technology, vol. 13, No. 3 (May/Jun. 1989), pp. 185-188.
"Infection Control When Servicing Medical and Laboratory Equipment," Journal Of Medical Engineering & Technology, vol. 13, No. 3 (May/Jun. 1989), pp. 177-180.
"Learning More About Medical EMC Pre-Certification" Jack Cowper, Tektronix, Inc, EE-Evaluation Engineering, May 1994, pp. 102-104.
"New Products," Journal of Medical Engineering & Technology, vol. 13, No. 3 (May/Jun. 1989), pp. 200-203.
"News, Trends and Techniques," Journal of Medical Engineering & Technology, vol. 13, No. 3 (May/Jun. 1989), pp. 197-199.
"Simplified Modelling of Sodium Transfer During Haemodialysis" article. (apparently undated).
"Sodium Dependant Trans-Cellular Water Shift During Dialysis," Proc. Int. Symp. Kinetic Mod. Artif. Org., Rostock-Wamemunde, 1982.
"The prediction of Drop Size From Intravenous Infusion Controllers," Journal of Medical Engineering & Technology, vol. 13, No. 3 (May/Jun. 1989), pp. 166-176.
"Touch Up" Touch Zone Table Generator, Version 2.0., User's Guide, Elographics, Inc. 1988.
"Variation of Ultrafiltration and Dialysate Sodium," Baldamus CA, Mion C., Shaldon S. (eds): Improvements in Dialysis Therapy, Contrib. Nephrol. Basel, Karger, 1989, vol. 74, pp. 176-181.
AccuTouch® Product Manual (Revision 3.1), Elo TouchSystems, Inc., 1988, 1992, 1994.
American Journal of Kidney Diseases, vol. II, No. 2, Sep. 1982.
APS-II Model 3000 Programmer with Model 3030 Function Pack Technical Manual, Pacesetter Systems, Inc., 1988.
Article from National Library of Medicine, "Heart Surgery with Cardiopulmonary Bypass in Patients on Chronic Dialysis Treatment: our experience" printed from www.ncbi.nlm.nih.gov dated Feb. 16, 2005.
Article from National Library of Medicine, "The Perioperative Management of Dialysis for Patients Undergoing Coronary Artery Bypass Surgery with Chronic Renal Failure", www.ncbi.nlm.nih.gov printed Apr. 4, 2005.
Articles from Jef Raskin about the history of the Macintosh, articles printed from JefRaskin@aol.com; 1996.
Austin Jon W. et al., "The Heart Lung Machine & Related Technologies of Open Heart Surgery," Phoenix Medical Communication, 1990.
Bassen, H., et al, "CDRH Laboratory Evaluation of Medical Devices for Susceptibility to Radio-Frequency Interference," Electromagnetic Inteference, pp. 107-1-5. (apparently undated).
Bauer, H. et al., "Influence of Variation of Ultrafiltration Rate on Cardiovascular Stability During Dialysis,", 1989, vol. 74, pp. 154-158.
Biomedizinische Technik (Biomedical Engineering), Prof. Dr-Ing Boenick Berlin et al., Vortrage der 14. Jahrestagung der Deutschen Gesellschaft fur Biomedizinische Technik e.V. Sep. 19-21, 1991 in Berlin.
Biomedizinische Technik (Biomedical Engineering), Prof. Dr-Ing Boenick Berlin et al., Vortrage der 22. Jahrestagung der Deutschen Gesellschaft fur Biomedizinische Technik e.V. gemeinsam mit der Osterreichischen und der Schweizerischen Gesellschaft für Biomedizinische Technik Sep. 7-10, 1988 in Stuttgart.
Biomedizinische Technik (Biomedical Engineering), Prof. Dr-Ing Boenick Berlin et al., Vortrage der 24. Jahrestagung der Deutschen Gesellschaft fur Biomedizinische Technik e.V., Sep. 1990.
Biomedizinische Technik (Biomedical Engineering), Prof. Dr-Ing Boenick Berlin et al., Vortrage der 25. Jahrestagung der Deutschen Gesellschaft fur Biomedizinische Technik e.V. Sep. 12-14, 1991 in Berlin.
Braun B., "Advancing the Science & Art of High-Flux Dialysis, HD-Secura" brochure, Medical Equipment, Inc. (apparently undated).
Brewis, Alistair et al., "Thorax", The Journal of the British Thoracic Society, , vol. 40 No. 2, Feb. 1985.
Cardiologia, Rivista Scientifica Dell, An Official Journal of Associazione Nazionale Medici Cardiologi Ospedalieri, Prof. Pier Luigi Prati, vol. 26 N. 9—Sep. 1996.
Cardiopulmonary Bypass, Second Edition, Glenn P. Gravlee, M.D., et al; 2000.
Cecere, Giovanni et al.Perfusion 2002; "A 10-year Review of Pediatric Perfusion Practice in North America", (pp. 83-89), 2002.
Dialyse-System DS 701 brochure, Fresnium Medical Care, 1989.
Dialyse-System DS 701 Brochure. (apparently undated).
DOS and Windows Drive Guide Version 2.0, Elo TouchSystems, Inc., 1987-1991, 1994.
ELODEV™ Touchscreen Drive Program Version 1.5 Installation Guide and Programmer's Reference Manual (Manual Version 3.1), EloGraphics, Inc., 1987-1991, 1993.
European Journal of Cardio Thoracic Surgery, Springer International, Coronary Artery Bypass Grafting in Chronic Renal Dialysis Patients; Intensive Perioperative Dialysis and Extensive Usage of Arterial Grafts (cover page—pp. 505-507) 1994.
Farrel, P.C. et al., "Performance Characteristics of Disposable Hemodialyzers," Dialysis and Transplantation, pp. 44-52, Jun./Jul. 1976.
Farrell, Peter et al., "Hemodialyzer reuse: Estimation of area loss from clearance data," Kidney International, vol. 3, pp. 446-450, 1974.

Fleig, Gordon E. "Optimizing Dialysis Using Sodium-Volume Modeling," Cordis Dow Research, Concord, California, Feb. 8, 1982.

Funck-Brentano, J. L., "Sodium-Free Water Clearance in Hemodialysis", International Society for Artificial Organs, 1981, pp. 51-53.

Goldsmith, Rainer et al Ergonomics an office publication of the Ergonomics Society and International Ergonomics Association, published monthly (vol. 32, 1989).

Gotch, Frank A., "Mass Transport in Re-Used Dialysers," Present at the Clinical Dialysis & Transplant Forum, pp. 1-13, Nov. 1980.

Gotch, Frank A. et al., "Formaldehyde Kinetics in Reused Dialyzers," Transactions, American Society for Artificial Internal Organs, vol. 29, 1983.

Bilinsky, Richard T. et al., "Hemodialysis Coil Reuse: A Safe and Economical New Method," JAMA, vol. 218, No. 12, pp. 1806-1808, Dec. 20, 1971.

Groom, Robert C. et al. "Alternative Method of Ultralfiltration After Cardiopulmonary Bypass", The Society of Thoracic Surgeons, (pp. 573-574) 1994.

Impuls Sistema de Dialisis (apparently undated).

International Journal of Human-Computer Interaction, vol. 2, No. 1, 1990.

International Journal of Man-Machine Studies, vol. 25, No. 3, Sep. 1986.

Jef Raskin, "Will Computers Ever Become Easy to Use?", vol. 40, No. 2, Feb. 1997 (pp. 98-101).

Journal of Ambulatory Monitoring, Stuart Meldrum, vol. 2 (1989).

Journal of American Nephrology Nurses Association, "Anna", vol. 14, No. 2, Apr. 1987.

Journal of Clinical Engineering, vol. 15, No. 1, Jan.-Feb. 1990.

Journal of Clinical Engineering, vol. 16, No. 2, (Mar./Apr. 1991).

Journal of Medical Engineering & Technology, vol. 13, No. 3, (May/Jun. 1989).

Journal of the International Anesthesia Research Society, "Anesthesia and Analgesia", vol. 66, No. 9, Sep. 1987(pp. 899-901).

Khoo, Michelle S.C. MD, et al American Journal of Kidney Diseases, Outcome and Complications of Intraoperative Hemodialysis During Cardiopulmonary Bypass With Potassium-Rich Cardioplegia, vol. 14, No. 6 (Jun.) 2003: pp. 1247-1255.

Kimura G. et al., "Prediction of Postdialysis Serum Sodium Concentration and Transcellular Fluid Shift Without Measuring Body Fluid Volumes," International Society for Artificial Organs, 1983, pp. 410-415.

Kimura, G. et al, "A Simulation Study of Transcellular Fluid Shifts Induced by Hemodialysis," Kidney International, vol. 24 (1983), pp. 542-548.

Kimura, G. et al., "A Computerized Model to Analyze Transcellular Fluid Shift During Hemofiltration," International Society for Artificial Organs, 1982, pp. 31-36.

Klein, Elias et al., "The Multidisciplinary Approach to Develop Artificial Organs", 2003, pp. 305-317.

Macintosh: The First Popular GUI, "A Computer for the Best of Us" (p. 1 of 4), undated.

Mion C. et al., "Clinical Implementation of Sodium Modeling," Baldamus CA, Improvements in Dialysis Therapy, Contrib. Nephrol. Basel, Karger, 1989, vol. 74, pp. 200-206.

Mion C. et al., "Effects of Ultrafiltration on Body Fluid Volumes and Transcapillary Colloid Osmotic Gradient in Hemodialysis Patients," Baldamus, CA, Improvements in Dialysis Therapy, Contrib. Nephrol. Basel, Karger, 1989, vol. 74, pp. 170-175.

Mion C. et al., "Principles of Fluid Dynamics and Circulatory Control in Eng-Stage Renal Failure," Baldamus CA, Improvements in Dialysis Therapy, Contrib. Nephrol. Basel, Karger, 1989, vol. 74, pp. 207-220.

Mion C., et al., "Optimizing Dialysis by Variation of Ultrafiltration Rate and Sodium Concentration Controlled by Continuous Measurement of Circulating Blood Volume," Baldamus CA, Improvements in Dialysis Therapy, Contrib. Nephrol. Basel, KArger, 1989, vol. 74, pp. 182-190.

Murisasco, A. et al., "Separation of NA$^+$ and H$_2$O Transport During Hemodialysis and Quantification of High-Low NA$_{Di}$ Levels During Sequential Sodium Therapy," vol. XXIX Trans Am Soc Artif. Intern Organs, 1983, pp. 645-648.

Nephron, S. Karger Medical and Scientific Publishers, Intraoperative versus Routine Hemodialysis in End-Stage Renal Disease Patients Undergoing Open-Heart Surgery, (pp. 170-175), 1992.

Okada, Hirokazu et al. Nephrology Dialysis Transplantation, "Does Intensive Perioperative Dialysis Improve the Results of Coronary Artery Bypass Grafting in Haemodialysed Patients?," (1999) 14: 771-775.

Sams® 9000 Perfusion System, Marketing Brochure, 1988.

Sams® 9000 Perfusion System, Touch the Vision, Aug. 7, 1989.

SmartSet Touchscreen Controller Family Technical Reference Manual (Manual Version 1.0), Elographics, Inc., 1993.

Srikanthan R. et al., "Cost-Effectiveness of a Low Dialysate Flow Rate in Hemodialysis: A Short-Term Comparative Study," Dialysis & Transplantation, vol. 19, No. 3, Mar. 1990, pp. 125-126.

The Japanese Journal of Thoracic Surgery, vol. No. 10 (pp. 833-837), 1991.

The Journal of the Japanese Association for Thoracic Surgery, vol. 41, No. 7, (pp. 25-30) Jul. 1993.

The Sams 9000 Perfusion System manual. (apparently undated).

TN-401 Haemodialysis System Brochure. (apparently undated).

TouchBack™ Version 1.2 Programmer's Reference Manual (Manual Version 2.0a), Elographics, Inc., 1988, 1989, 1993.

Weiss M. et al., "Information System Designed with users and Operating Rooms in Mind", Medical Device & Diagnostic Industry, pp. 68-71, Nov. 1989.

HD Secura Dialyse Operating Manual, 79 pages, (apparently undated).

Monitral SC 30, 6 pages, (apparently undated).

DPM Dialysis Programmer Module, Ultrafiltration and Dialysate Osmolality Modeling, 2 pages, (apparently undated).

Compudial/PS1, The Dialysis System That Takes Care of Itself. So You Can Take Care of Your Patients, 5 pages, (apparently undated).

Sams 5500 Pump with Sara® Self-Adjusting Roller Assembly Advertisement, 3 pages, Oct./Nov. 1975.

Compudial PS/1 Hemodialysis Machine Manual No. 721-2100, Revision B (40468), 64 pages, (apparently undated).

Compudial/KP1 Computer Dialysis Systems, Inc. Advertisement, 2 pages, (apparently undated).

Hemodialysis System TN-401 Series, 4 pages, (apparently undated).

Haemodialysis System TN 501C Series, 4 pages, (apparently undated).

ABG Semca Dialyse, 12 pages, (apparently undated).

HD Secura-Plus, 34 pages, (apparently undated).

"UF Control: B-D Drake Willock's Intelligent Solution to Accurate Fluid Management," 2 pages, (apparently undated).

Hemodialysis System TN-401 Series, 2 pages, (apparently undated).

"An Improved Procedure for Rinsing of Cordis Capillary Kidneys," Schmitz, W. and Henegen, M. from the Department of Medicine, University of Koln (Cologne), Germany, 30, undated.

"The Clinical Use of Electolyte—And UF—Variation By the Computer Modeling System CMS08," Fresenius Clinical Aplications, 1986.

"Reutilisateur—Pour Rein Artificiel 704000," 2 pages, marketing brocure pulished by ABG Semca, S.A., (apparently undated).

"The Acme Model 2500 Digital Bedside Scale, Symposium on Multiple Use: Addendum," 1 page, Acme Medical Scales, Jan. 1980.

Milroyal Central Dialysate System Instruction Manual, Jul. 1969.

Hone, P.W.E. et al., "Hemodialyzer Performance: An Assessment of Currenlty Avaliable Units," Journal of Dialysis 1(3), 285-310 (1977).

Request for Filing of Reexamination of U.S. Patent No. 5,247,434 and related documents, undated.

Request for Filing of Reexamination of U.S. Patnt No. 6,284,131 and related documents, undated.

Opening Expert Witness Report of Dr.-Günter Rau regarding the Invalidity of Certain Claims of U.S. Patent Nos. 5,247,434; 6,284,131; 5,326,476; and 5,744,027, undated.
Opening Expert Witness Report of Stephen G. Kunin regarding Inequitable Conduct During Prosecution of the Patents-In-Suit, undated.
Opening Expert Witness Report of Robert C. Phares in the *Matter of Fresenius Medical Care Holdings, Inc. and Fresenius USA, Inc. v. Baxter International, Inc. and Baxter Healthcare Corporation*, undated.
Opening Expert Witness Report of Terrence K. Jones in the *Matter of Fresenius Medical Care Holdings, Inc. and Fresenius USA, Inc. v. Baxter International, Inc. and Baxter Healthcare Corporation*, undated.
Opening Expert Witness Report of Charles Ragsdale regarding the Invalidity of Certain Claims of U.S. Patent No. 5,744,027, undated.
Opening Expert Witness Report of Mr. James Causey Regarding the Invalidity of Certain Claims of U.S. Patent Nos. 4,274,434, 5,326,476, 5,744,027 and 6,284,131, undated.
Opening Expert Witness Report of Mr. Jeff Riley in the *Matter of Fresenius v. Baxter*, undated.
Opening Expert Witness Report of Dr. Richard A. Ward Regarding the Invalidity of Certain Claims of U.S. Patent Nos. 5,326,476 and 5,486,286, undated.
Expert Report of John Turner, undated.
Rebuttal Expert Report of Dr. Lee W. Henderson, undated.
Rebuttal Expert Report of J. Dennis Bruner, Ph.D., P.E., undated.
Expert Report of Lawrence J. Goffney, Jr., undated.
Expert Report of Richard F. Ferraro Regarding Infringement of U.S. Patent Nos. 5,247,434; 6,284,131 B1; 5,326,476; 5,486,286; and 5,774,027, undated.
Rebuttal Expert Report of Richard F. Ferraro Regarding the Validity of U.S. Patents: 5,247,434; 6,284,131 B1; 5,326,476; and 5,774,027 and attached Addendum A-J., undated.
Fresenius' Motion For Summary Judgment of Invalidity of the Asserted Claims of U.S. Patent Nos. 5,247,434 and 6,284,131 and attached Exhibits 1-35, undated.
District Court Order in response to Fresenius' Motion For Summary Judgment of Invalidity of the Asserted Claims of U.S. Patent Nos. 5,247,434 and 6,284,131 and Baxter's Motion for Partial Summary Judgment of Validity, undated.
Declaration of Robert Phares in Support of Fresenius' Motion for Summary Judgment of Invalidity of the Asserted Claims of U.S. Patent Nos. 5,247,434 and 6,284,131, undated.
Declaration of Thomas S. McClenahan in Support of Fresenius' Motion for Summary Judgment of Invalidity of the Asserted Claims of the U.S. Patent Nos. 5,247,434 and 6,284,131 and attached Exhibits 1 through 35, undated.
Fresenius' Opposition to Defendants' Motion for Partial Summary Judgment of Validity, undated.
Declaration of James Causey in Support of Fresenius' Opposition to Defendants' Motion for Partial Summary Judgment of Validity, undated.
Declaration of Jeff Riley in Support of Fresenius' Opposition to Defendants' Motion for Partial Summary Judgment of Validity and attached Exhibit A, undated.
Declaration of Thomas S. McClenahan in Support of Fresenius' Opposition to Defendants' Motion for Partial Summary Judgment of Validity and Exhibits A to Z, undated.
Declaration of Richard Alan Griewski in Opposition to Defendants' Motion for Partial Summary Judgment of Validity and Exhibit A to C, undated.
Fresenius' Reply Brief in Support of its Motion for Summary Judgment of Invalidity of the Asserted Claims of U.S. Patent Nos. 5,326,476 and 5,744,027, undated.
Fresenius' Reply to Baxter's Opposition to Fresenius' Motion for Summary Judgment of Invalidity of the Asserted Claims of U.S. Patent Nos. 5,247,434 and 6,284,131, undated.
Declaration of Dr. Ben J. Lipps in Support of Fresenius' Reply Regarding Fresenius' Motion for Summary Judgment of Invalidity of the Asserted Claims of U.S. Patent Nos. 5,247,434 and 6,284,131, undated.

Declaration of Michael J. Abernathy In Support of Baxter's Opposition to Fresenius' Motion for Summary Judgment of Invalidity of the Asserted Claims of U.S. Patent Nos. 5,326,476 and 5,744,027 and attached Exhibits 2-8, 12, 13 and 15, undated.
Declaration of Richard F. Ferraro In Support of Baxter's Opposition to Fresenius' Motion for Summary Judgment of Invalidity of the Asserted Claims of U.S. Patent Nos. 5,326,476 and 5,744,027 and attached Exhibit 1, undated.
Fresenius' Notice of Motion and Motion For Summary Judgment of Invalidity of the Asserted Claims of U.S. Patent Nos. 5,326,476 and 5,744,027; Memorandum of Points & Authority in Support Thereof, undated.
Declaration of Thomas S. McClenahan In Support of Fresenius' Notice of Motion and Motion For Summary Judgment of Invalidity of the Asserted Claims of U.S. Patent Nos. 5,326,476 and 5,744,027; Memorandum of Points & Authority in Support Thereof and attached Exhibits 1-34, undated.
Declaration of Charles Ragsdale In Support of Fresenius' Motion for Summary Judgment of Invalidity of the Asserted Claims of U.S. Patent Nos. 5,326,476 and 5,744,027, undated.
Declaration of Richard A. Ward In Support of Fresenius' Motion for Summary Judgment of Invalidity of the Asserted Claims of U.S. Patent Nos. 5,326,476 and 5,744,027, undated.
Declaration of Limin Zheng In Support of Fresenius' Motion for Summary Judgment of Invalidity of the Asserted Claims of U.S. Patent Nos. 5,326,476 and 5,744,027 and attached Exhibits A, B and D-I, undated.
Fresenius' Motion for Summary Judgment of Invalidity of the Asserted Claims of U.S. Patent Nos. 5,247,434 and 6,284,131, undated.
Court entered judgment on the jury's findings of Jul. 17, 2006.
Baxter's motion for judgment as a matter of law to set aside the jury's findings filed on Jul. 28, 2006.
Direct and cross-examinations from transcripts of Mr. James Causey pp. 829 to 832 and 859 to 874, undated.
Direct and cross-examinations from transcripts of Mr. Gunter Gau pp. 601 to 611, undated.
Fresenius' Opposition to Baxter's Rule 50(b) Renewed Motion for Judgment As a Matter of Law dated Aug. 16, 2006.
Defendants' Motion For Partial Summary Judgment of Validity dated Mar. 7, 2006.
Declaration of Michael J. Abernathy in Support of Defendants' Motion for Partial Summary Judgment of Validity and attached Exhibits 1-2, 3a, 3b, 5-8, 11-20 and 23-26, undated.
Baxter's Opposition to Fresenius' Motion for Summary Judgment of Invalidity of the Asserted Claims of U.S. Patent Nos. 5,247,434 and 6,284,131 dated Mar. 21, 2006.
Declaration of Dr. J. Dennis Bruner in Support of Baxter's Opposition To Fresenius' Motion for Summary Judgment of Invalidity of the Asserted Claims of U.S. Patent Nos. 5,247,434 and 6,284,131, undated.
Declaration of Michael J. Abernathy in Support of Baxter's Opposition To Fresenius' Motion for Summary Judgment of Invalidity of the Asserted Claims of U.S. Patent Nos. 5,247,434 and 6,284,131 and attached Exhibits 1, 2, 4-15, 17, 18, 22, 23, 25, 26, 35, 46, 48, 54 and 60, undated.
Declaration of Richard F. Ferraro in Support of Baxter's Opposition To Fresenius' Motion for Summary Judgment of Invalidity of the Asserted Claims of U.S. Patent Nos. 5,247,434 and 6,284,131, undated.
Baxter's Opposition To Fresenius' Motion for Summary Judgment of Invalidity of the Asserted Claims of U.S. Patent Nos. 5,326,476 and 5,774,027 filed Mar. 21, 2006.
Declaration of Dr. Lee W. Henderson In Support of Baxter's Opposition to Fresenius' Motion for Summary Judgment of Invalidity of the Asserted Claims of U.S. Patent Nos. 5,326,476 and 5,744,027, undated.
Declaration of Martin J. Cnkovich in Support of Fresenius' Reply Regarding Fresenius' Motion for Summary Judgment of Invalidity of the Asserted Claims of U.S. Patent Nos. 5,247,434 and 6,284,131 and attached Exhibit A, undated.
Declaration of Thomas S. McClenahan in Support of Fresenius' Reply To Baxter's Opposition to Fresenius' Motion for Summary Judgment of Invalidity of the Asserted Claims of U.S. Patent Nos. 5,247,434 and 6,284,131 and attached Exhibits C, D, E, G, H, I, J, K and L, undated.
Reply Memorandum in Support of Defendants' Motion for Partial Summary Judgment of Validity (pp. 1 to 20), undated.
Order Denying Fresenius' Motion for Summary Judgment of Invalidity of the '476 and '027 Patents, undated.

Bench Memorandum Regarding the Construction of Certain Limitations of Claim 7 of U.S. Patent No. 5,326,476.
Baxter's Bench Memorandum Regarding Claim 7 of the '476 Patent, undated.

* cited by examiner

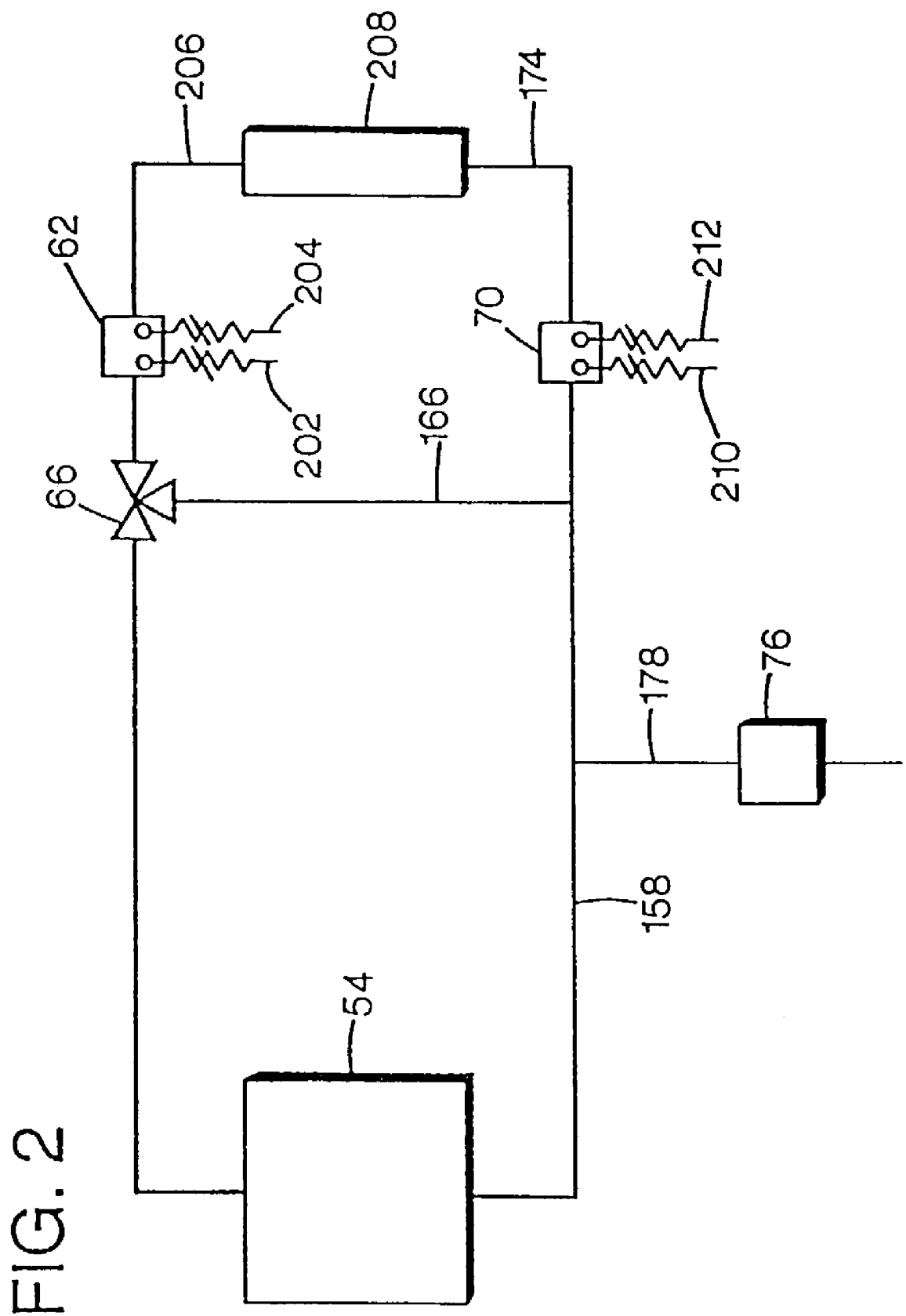

METHODS FOR KIDNEY DIALYSIS

RELATED APPLICATIONS

This application is a continuation of U.S. patent application Ser. No. 09/711,240 filed on Nov. 13, 2000, now abandoned, which is a continuation of U.S. patent application Ser. No. 09/067,922 filed on Apr. 28, 1998, now abandoned, which is a continuation of U.S. patent application Ser. No. 08/479,688, filed on Jun. 7, 1995, now U.S. patent No. 5,744,027, which is a divisional of U.S. patent application Ser. No. 08/122,047, filed on Sep. 14, 1993, now U.S. Pat. No. 5,486,286, which is a divisional of U.S. patent application Ser. No. 07/688,174, filed on Apr. 19, 1991, now U.S. Pat. No. 5,247,434.

FIELD OF THE INVENTION

The present invention relates to improvements in kidney dialysis machines.

BACKGROUND OF THE INVENTION

Kidney dialysis machines are well known in the art and are illustrated, for example, in U.S. Pat. Nos. 3,598,727, 4,172,033, 4,267,040, and 4,769,134.

While machines according to the prior art provide a number of advantageous features, they nonetheless have certain limitations. The present invention seeks to overcome certain drawbacks of the prior art and to provide new features not heretofore available.

A discussion of the features and advantages of the present invention is deferred to the following detailed description, which proceeds with reference to the accompanying drawings.

BRIEF DESCRIPTION OF THE DRAWINGS

FIG. 2 is a schematic diagram showing flow path locations and components of a pre-dialyzer flow sensor and a post-dialyzer, flow sensor according to the present invention.

DETAILED DESCRIPTION

Hydraulic Circuit

Figure 1A:
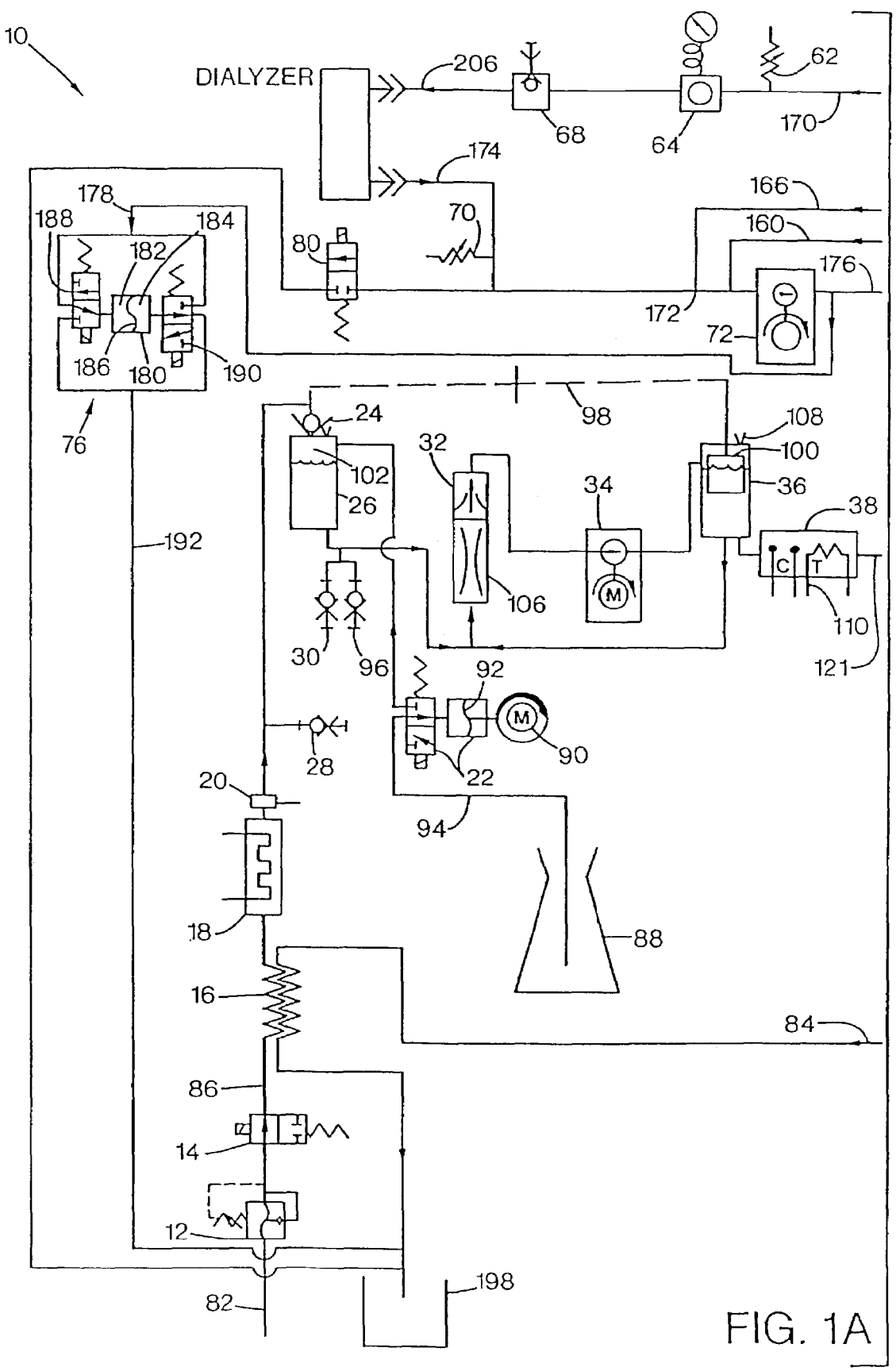
FIGS. 1A and 1B show a schematic hydraulic diagram of a preferred embodiment of a kidney dialysis machine according to the present invention.
Figure 1B:
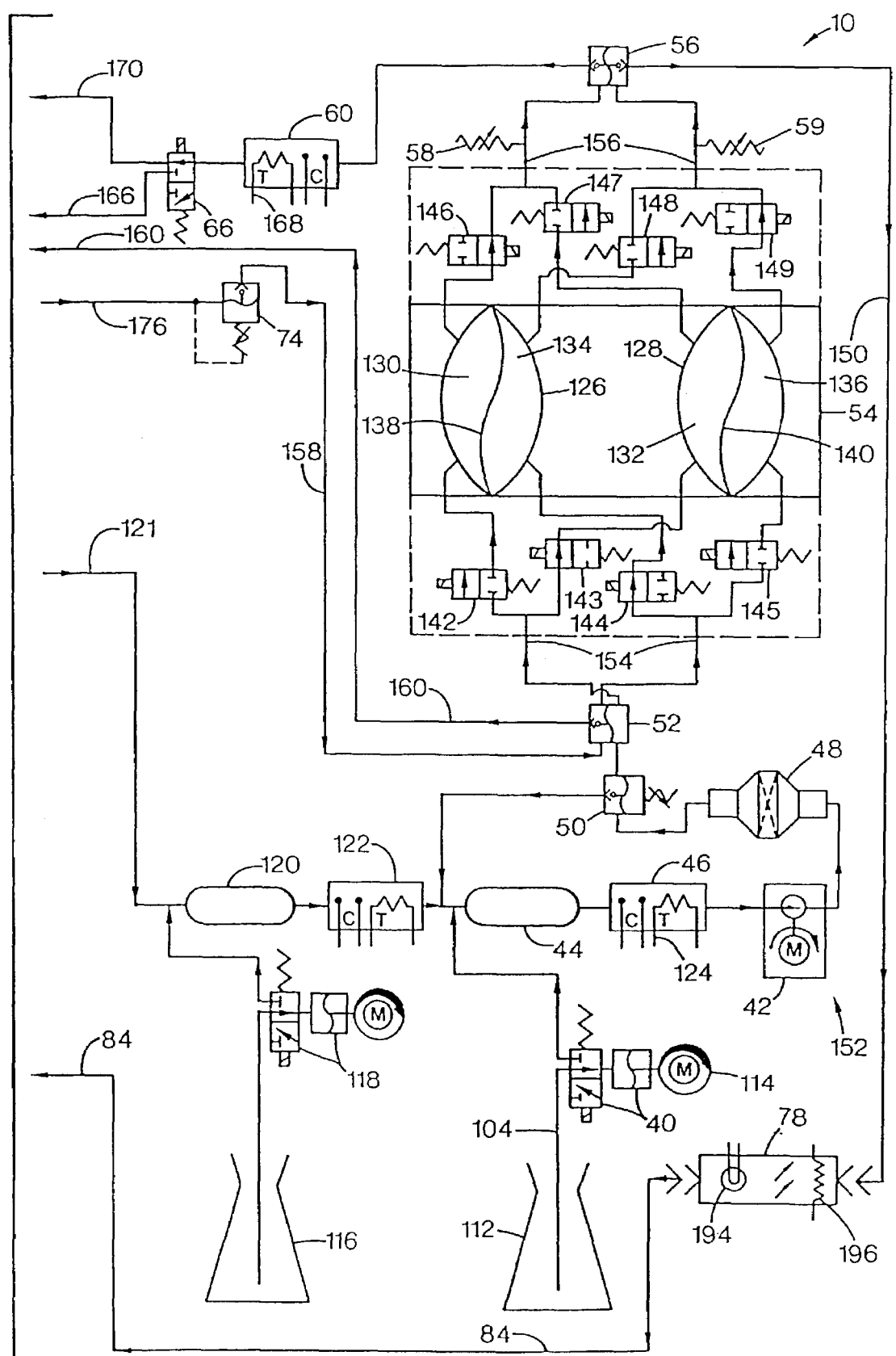

A hydraulic circuit 10 representing a preferred embodiment of an improved hemodialysis machine according to the present invention is illustrated in FIGS. 1A and 1B. The hydraulic circuit 10 is comprised of the following principal components: an incoming water pressure regulator 12, a water on/off valve 14, a heat exchanger 16, a heater 18, a safety thermostat 20, an "A" concentrate pump 22, a supply valve 24, an air gap chamber 26, an "A" rinse fitting 28, a "B" rinse fitting 30, a deaeration sprayer 32, an air removal pump 34, a vented air trap 36, an "A" conductivity probe 38, a "B" concentrate pump 40, a supply pump 42, a "B" mix chamber 44, a "B" conductivity probe 46, a dialysate filter 48, a supply regulator 50, an input pressure equalizer 52, a flow equalizer 54, an output pressure equalizer 56, end-of-stroke sensors 58 59 a dialysate conductivity probe 60, a pre-dialyzer flow sensor 62, a dialysate pressure transducer 64, a bypass valve 66, a dialysate sample port 68, a post-dialyzer flow sensor 70, a dialysate pressure pump 72, a UF removal regulator 74, a UF flow meter 76, a blood-leak detector 78, and a rinse valve 80. The aforementioned components are interconnected as shown in FIGS. 1A and 1B.

The incoming water pressure regulator 12 is coupled to a pressurized water source 82 and reduces and stabilizes the water supply pressure to a level of about 20 psig.

The water on/off valve 14 opens when machine power is on, thereby allowing water to flow from the source 82 into the hydraulic circuit 10. When the machine power is off, the water on/off valve 14 is closed.

The heat exchanger 16 transfers heat from "spent" or effluent dialysate, passing through conduit 84, to the cooler incoming water passing through conduit 86 as these two liquids pass countercurrently through separate but adjacent compartments in the heat exchanger 16. In this way, the incoming water is warmed, which reduces the amount of heat energy that must be supplied to the water by the heater 18.

The heater 18 further warms the incoming water to a suitable temperature for hemodialysis, which is about 38° C. A typical heater 18 is a resistance type known in the art, rated at about 1500 watts. The heater 18 includes a downstream thermistor 20 or analogous temperature-sensing device. A thermistor as known in the art is essentially a temperature-sensitive resistor which experiences a change in electrical resistance that is inversely proportional to a corresponding change in temperature. The thermistor 20 is coupled to the machine's microprocessor (not shown in FIGS. 1A and 1B) which utilizes signals from the thermistor for turning the heater 18 on and off as required to maintain the water temperature at the proper level.

The "A" concentrate pump 22 propels either "acid" or "acetate" concentrate as known in the art from a container thereof 88 into the air gap chamber 26. The "A" concentrate pump 22 is a fixed-volume cam-driven pump. A stepper motor 90 calibratable to rotate a precise number of rotations per minute is preferably used to drive the "A" concentrate pump 22. The stepper motor includes a shaft (not shown) to which is mounted a cam (not shown) which engages a flexible diaphragm 92, thereby delivering a known volume of "A" concentrate per each rotation of the cam. An optical sensor (not shown) on the cam monitors the angular rotation of the cam for processing by the microprocessor (not shown). The microprocessor, using information pertaining to dialysate flow rate and concentrate parameters entered by the machine operator using a touch screen (described in detail hereinbelow), calculates the amount of concentrate necessary to achieve a correct ratio of water and "A" concentrate for hemodialysis therapy. The microprocessor thereby adjusts the angular velocity of the stepper motor shaft.

An "A" concentrate line 94 is used to deliver "A" concentrate from the supply 88 thereof to the "A" concentrate pump 22. When rinsing the machine, the "A" concentrate line 94 is coupled to the "A" rinse fitting 28 which serves as a source of rinse water for the "A" concentrate line.

When disinfecting the machine, the "A" concentrate line 94 is coupled to a disinfect fitting 96 which enables the "A" concentrate pump 22 to deliver a chemical disinfectant to the "A" concentrate line 94.

Heated water enters the air gap chamber 26 through the supply valve 24. The supply valve 24 is actuated by a lever 98. The lever 98 is coupled to a float 100 inside the air trap 36. Thus, the float 100 controls water flow into the hydraulic circuit 10 by opening the supply valve 24 when the water level supporting the float drops and by closing the supply valve 24 when the water level in the air trap 36 rises.

The air gap 102 in the chamber 26 is at atmospheric pressure. The air gap 102 helps prevent incoming water from flowing backward (upstream) in the event of a pressure drop in the water supply 82.

A proximity sensor (not shown in FIG. 1A but described in further detail hereinbelow) is built into the "A" fitting 28. The proximity sensor senses when the "A" concentrate line 94 is coupled to the "A" rinse fitting 28 and when it is not, thereby serving as an important safety interlock feature which prevents unsafe operation of the machine.

The "B" rinse fitting 30 supplies water for rinsing the "B" concentrate line 104. During rinse, the "B" concentrate line 104 is coupled to the "B" rinse fitting 30. During acetate dialysis, the "B" concentrate line 104 is also coupled to the "B" rinse fitting 30 for recirculation of acetate dialysate solution therethrough.

The "B" rinse fitting 30 is also provided with a proximity sensor (not shown in FIG. 1A but described in further detail hereinbelow) similar to that provided with the "A" rinse fitting 28.

The hydraulic circuit includes components operable to remove dissolved gases from the liquid passing therethrough. Otherwise, if the liquid were not deaerated, dissolved gases therein could adversely affect the course of a dialysis treatment, including the accuracy at which the machine performs ultrafiltration of the patient. To facilitate deaeration, liquid flows through the air-removal sprayer 32 at a rate of about 1500 mL/min at a subatmospheric pressure (about 500 mmHg). The reduced pressure is attained by aspirating the liquid via the air-removal pump 34 through a flow restrictor 106 upstream of the air-removal sprayer 32. The air-removal sprayer 32 breaks the liquid into small droplets as it is subjected to the subatmospheric pressure, which favors the formation of air bubbles.

The air trap 36 vents air bubbles liberated from the liquid by the deaeration sprayer 32 through a vent opening 108 open to the atmosphere. The air trap also contains the float 100 discussed hereinabove.

The "A" conductivity probe 38 measures the electrical conductivity of the mixture of water and "A" concentrate. Conductivity is an accurate way to ascertain whether the "A" concentrate solution has been correctly proportioned. The conductivity measured at the "A" conductivity probe 38 can vary depending upon the ionic strength and electrolytic profile of the "A" concentrate. Since conductivity will be affected by temperature, the "A" conductivity probe 38 is also provided with a thermistor 110. The thermistor 110 is coupled to the microprocessor (not shown) which performs the necessary temperature compensation.

The "B" concentrate pump 40 delivers bicarbonate concentrate from a supply thereof 112 and is operable only during bicarbonate dialysis therapy. The "B" concentrate pump 40 is a fixed-volume cam-driven pump similar to the "A" concentrate pump 22. The "B" concentrate pump 40 is driven by a stepper motor 114. As with the "A" concentrate pump, the angular velocity of the stepper motor shaft is monitored by an optical sensor. The optical sensor is connected to the machine's microprocessor which calculates the amount of "B" concentrate necessary to achieve a correct dialysate composition for safe hemodialysis therapy and correspondingly controls the angular velocity of the cam. The "B" concentrate pump 40 will automatically compensate for changes in dialysate flow rate in the event that said flow rate is changed during a dialysis treatment by increasing or decreasing the pump rate.

FIG. 1B also shows an optional third concentrate supply 116, a third fixed-volume cam-driven concentrate pump 118 operable in the same manner as the "A" and "B" concentrate pumps 22, 40, a corresponding mixing chamber 120 (coupled to the conductivity probe 38 via a conduit 121) and conductivity probe 122.

The "B" mix chamber 44 provides thorough mixing of the "B" concentrate with the proportioned mixture of "A" concentrate and water to form dialysate before the dialysate enters the "B" conductivity probe 46.

The "B" conductivity probe 46 monitors dialysate conductivity. Electronic circuitry (not shown) coupled to the "B" conductivity probe 46 subtracts the conductivity measured at the "A" conductivity probe 38 from the conductivity measured at the "B" conductivity probe 46. During acetate dialysis, the difference in these conductivity readings should be zero. Since conductivity measurements are affected by temperature, a thermistor 124 is included with the "B" conductivity probe 46 to provide temperature compensation of the "B" conductivity reading. The thermistor 124 also comprises a portion of a redundant high temperature alarm subsystem.

Before describing the hydraulic circuit any further, it is appropriate to briefly describe the flow equalizer 54. The flow equalizer 54 comprises a first chamber 126 and a second chamber 128 of substantially equal volume. Each chamber 126, 128 is comprised of two compartments, one termed a "pre-dialyzer" or "pre" compartment 130, 132 and the other a "post-dialyzer" or "post" compartment 134, 136. Each pair of opposing "pre" and "post" chambers is separated by a flexible diaphragm 138, 140. Solenoid-actuated valves 142-149 control the filling and emptying of each compartment. In general, each compartment 130, 132, 134, 136 is completely filled before its contents are discharged. Also, the "pre" compartments 130, 132 are alternately filled and discharged and the "post" compartments 134, 136 are alternately filled and discharged. Also, filling a "pre" compartment 130, 132 causes a corresponding discharge of an opposing "post" compartment 134, 136, respectively. The "pre" compartments 130, 132 alternately fill from the supply pump 42 and alternately discharge to the dialyzer. The "post" compartments 134, 136 alternately fill with "spent" dialysate returning from the dialyzer and discharge the spent dialysate to a drain line 150. For example, dialysate from the supply pump 42 enters the "pre" compartment 132, thereby displacing the diaphragm 140 in FIG. 1B to the right, causing the "post" compartment 136 to empty. Simultaneously, "post" compartment 134 fills while "pre" compartment 130 empties.

The flow equalizer 54 operates via a four-phase cycle. In the first phase, valves 142, 145, 147, and 148 turn on, thereby filling the "pre" compartment 130 with fresh dialysate and displacing the diaphragm 138 to the right in FIG. 1B. Such displacement of the diaphragm 138 expels "spent" dialysate contained in the "post" compartment 134, which has a volume equal to the volume in the "pre" compartment 130, to pass to the drain line 150. At the same time, effluent dialysate from the dialyzer enters the "post" compartment 136, thereby forcing the diaphragm 140 to be displaced to the left in FIG. 1B to expel an equal volume of fresh dialysate from the "pre" compartment 132 to the dialyzer. In the second phase, all the solenoid valves 142-149 turn off for a short period of time (about 125 m sec). This brief shut-off eliminates adverse affects on ultrafiltration accuracy that would otherwise result if at least two of said valves were open at the same time. In the third phase, solenoid valves 143, 144, 146, and 149 are energized, causing the "post" compartment 134 to fill with effluent dialysate from the dialyzer, thereby expelling fresh rash dialysate from "pre" compartment 130 to the dialyzer. Also, the "pre" compartment 132 simultaneously fills with fresh dialysate from the supply pump 42, thereby expelling effluent dialysate from the remaining "post" compartment 136 to the drain line 150. In the fourth phase, all the solenoid valves 142-149 are again turned off for about 125 msec.

Since the volumes of opposing "pre" and "post" compartments 130 134 and 132, 136 are equal, the flow equalizer 54 volumetrically balances the flow of dialysate to and from the dialyzer. A further benefit of such volumetric equality is that dialysate flow to the dialyzer can be accurately measured over a wide range of flow rates.

The supply pump 42 has two functions: (a) to supply an adequate dialysate flow volume and pressure to fill the flow equalizer compartments with dialysate, and (b) to create a flow of dialysate through a loop 152 comprised of the dialysate filter 48, the supply regulator 50, the "B" mix chamber 44, and the "B" conductivity probe 46. The supply pump 42 delivers dialysate at a maximum regulated pressure of 12.5 psig and at a flow rate approximately 50 mL/min higher than the dialysate flow rate set by the operator using the touch screen.

The dialysate filter 48 is used to occlude downstream passage of particulate foreign material into the flow equalizer 54. The supply regulator 50 is adjusted to an output pressure of approximately 16 psig. Whenever the "pre" and "post" compartments of the flow equalizer 54 reach the end of a fill cycle during phases 1 or 3, pressure builds up in the loop 152. As the pressure increases to about 16 psig, the supply regulator 50 opens sufficiently to pass the dialysate output of the supply pump 42 through the loop 152 until the next phase 1 or 3.

The input pressure equalizer 52 equilibrates hydraulic pressures at the inlets 155 of the flow equalizer 54 so that the compartments 130, 132, 134, 136 fill at the same rate. Likewise, the output pressure equalizer 56 equilibrates hydraulic pressures at the outlets 156 of the flow equalizer 54. The input and output pressure equalizers are discussed in greater detail hereinbelow.

The input pressure equalizer 52 also automatically equilibrates the pressure of the dialysate flowing through the downstream lines 158, 160 with the pressure of dialysate at the flow equalizer inlets 154. Whenever the pressure at the flow equalizer inlets 154 exceeds the pressure generated by the dialysate pressure pump 72, the input pressure equalizer 52 restricts the flow of dialysate in lines 158, 160. Such equilibration of pressures allows both chambers 126, 128 in the flow equalizer 54 to be filled at identical rates.

End-of-stroke sensors 58, 59 are provided at the outlets 156 of the output pressure equalizer. The end-of-stroke sensors 58, 59 verify when the flow equalizer compartments have reached the end of a fill cycle (end of stroke). When the compartments are full, the end-of-stroke sensors 58, 59 send a no-flow signal to the machine's microprocessor, indicating that the compartments are full.

The dialysate conductivity probe 60 measures the conductivity of the dialysate before it enters the dialyzer. The machine's microprocessor compares the measured conductivity with an expected conductivity value (discussed in detail hereinbelow) based upon concentrate-formulation information entered by the operator using the touch screen. If the measured dialysate conductivity is excessively above or below the expected conductivity value, the machine's microprocessor activates a conductivity alarm. Also, the bypass valve 66 is triggered during a conductivity alarm to divert dialysate away from the dialyzer through conduit 166.

The dialysate conductivity probe 60 includes a thermistor 168 which allows temperature compensation of the conductivity reading. The electronic signal from the thermistor 168 is also utilized to provide a dialysate temperature display on the machine's touch screen as well as primary high and low temperature alarm limits. The dialysate conductivity as measured by the conductivity probe 60 is also displayed on the machine's touch screen.

The dialysate flow sensor 62 includes a self-heating variable thermistor as well as a reference thermistor (not shown in FIG. 1A, but discussed in detail hereinbelow). The dialysate flow sensor 62 is used mainly as a bypass monitor. Whenever the machine is in bypass, the resulting lack of dialysate flow past the flow sensor 62 serves as a verification that the bypass valve 66 is functioning correctly.

The dialysate pressure transducer 64 senses dialysate pressure and converts the pressure reading into an analog signal proportional to the dialysate pressure. The analog signal is utilized by the machine's microprocessor as the basis for a dialysate pressure display on the touch screen, pressure alarms, and other dialysate control functions (not shown in FIGS. 1A and 1B).

The bypass valve 66 protects the hemodialysis patient in the event of a temperature or conductivity alarm by diverting dialysate flow away from the dialyzer. The bypass valve 66 is a three-way solenoid valve which, when triggered, occludes the conduit 170 leading to the dialyzer and shunts the dialysate flow through conduit 166 to a location 172 downstream of the dialyzer.

The dialysate sample port 68 is an appliance which allows the operator to obtain a sample of the dialysate using a syringe for independent testing.

A second dialysate flow sensor 70 is located in the post-dialyzer ("venous") line 174. The second flow sensor 70 is constructed similarly to the first flow sensor 62 and is discussed in detail hereinbelow. The second flow sensor 70 is utilized for checking the accuracy of the machine's ultrafiltration capability.

The dialysate pressure pump 72 is situated downstream of the dialyzer. An accompanying recirculation loop comprising lines 158, 160 conducts effluent dialysate to the inlet pressure equalizer 52. The recirculation loop 158, 160 thereby helps equilibrate pressure differences that might otherwise be transmitted to the flow equalizer 54 and also serves as a source of hydraulic pressure sufficient to fill the UF flow meter 76 when demanded thereby.

The dialysate pressure pump 72 circulates dialysate at a constant flow rate of 1500 mL/min through the recirculation loop 158, 160 without affecting the overall dialysate flow rate through the hydraulic circuit 10. As a result, the dialysate pressure pump 72 is usable to adjust pressure differences across the dialyzer membrane.

As long as the dialysate pressure pump 72 receives an adequate volume of dialysate for pumping, the flow dynamics of dialysate through the hydraulic circuit 10 are unaffected. However, should liquid be removed from the recirculation loop 158, 160, the dialysate pressure pump will attempt to replace that lost volume by demanding more volume from the dialyzer. Since the flow equalizer 54 maintains volumetric constancy of dialysate passing to and from the dialyzer, the only fluid available to replace any fluid lost from the loop 158, 160 must come from the dialyzer itself. Hence, by precisely controlling the amount of liquid removed from the recirculation loop 158, 160 (using the UF flow meter 76), the operator can precisely control the amount of liquid that must be removed from the hemodialysis patient via the dialyzer.

Since the dialysate pumped by the dialysate pressure pump 72 has a partially restricted flow, a sufficient pressure is thereby provided at the input of the UF removal regulator 74. The UF removal regulator 74 regulates hydraulic pressure at the input 178 of the UF flow meter 76.

The UF flow meter 76 is comprised of a chamber 180 separated into two subcompartments 182, 184 via a diaphragm 186. Each subcompartment 182, 184 has a corresponding valve 188, 190, respectively, associated therewith. Either subcompartment 182, 184 of the UF flow meter 76 can only fill when the corresponding valve 188, 190 is opened. Whenever a first subcompartment 182 is filling, the opposing second compartment 184 is emptying its contents to a drain line 192. The rate of UF removal through the UF flow meter 76 is governed by the rate at which the corresponding valves 188, 190 are alternately opened and closed.

Whenever liquid leaves the recirculation loop 158, 160 through the UF flow meter 76, correspondingly less liquid is recirculated through the recirculation loop 158, 160. This causes a corresponding "starvation" at the input 172 of the dialysate pressure pump 72 which generates a corresponding decrease in dialysate pressure in the dialyzer. The decreased dialysate pressure causes a volume of liquid to be removed from the patient that is equal to the volume of liquid removed from the recirculation loop 158, 160 via the UF flow meter 76. These volumes will be equal so long as the dialyzer has an ultrafiltration capability sufficient to remove said volume from the patient at the desired rate.

Effluent dialysate expelled from the flow equalizer 54 passes through and is monitored for the presence of blood by the blood-leak detector 78. The blood-leak detector 78, discussed in further detail hereinbelow, comprises a light source 194 and a photocell 196 which monitors light transmitted through the effluent dialysate solution passing therethrough. If blood leaks through the dialyzer membrane from the patient into the dialysate the dialysate passing through the blood-leak detector 78 will absorb a portion of the light passing therethrough. The corresponding decrease in the amount of light reaching the photocell 196, if the decrease is excessive, triggers a blood-leak alarm by the machine.

Effluent dialysate from the blood-leak detector 78 is routed through conduit 84 to the heat exchanger 16, then to a drain 198.

The rinse valve 80 allows the UF flow meter 76 to remove rinse water from the recirculation loop 158, 160 at a rate of about 4 L/h. Such rinsing ensures an adequate flushing of the recirculation loop 158, 160 and UF flow meter 76. However, since liquid is removed from the loop 158, 160 at a relatively high rate during rinse, the rinse valve 80 also allows an equivalent volume of liquid to be added back to the loop 158, 160.

User Interface

In the preferred embodiment, a touch screen user interface is employed.

Touch screens are known in the art and are commercially available from a number of sources, including Elographics West of San Diego, Cal. The use of touch screens in user interface applications for medical equipment is also known, as shown for example in U.S. Pat. Nos. 4,974,599 and 4,898,578, the disclosures of which are incorporated herein by reference.

In the prior art, as illustrated by the above-referenced patents, touch screens have been used in conjunction with computers and CRTs to provide a control panel that can be changed under computer control. The means by which a computer, a CRT, and a touch screen can be cooperatively operated in this fashion is well known and does not, per se, form a part of this invention.

Figure 7:
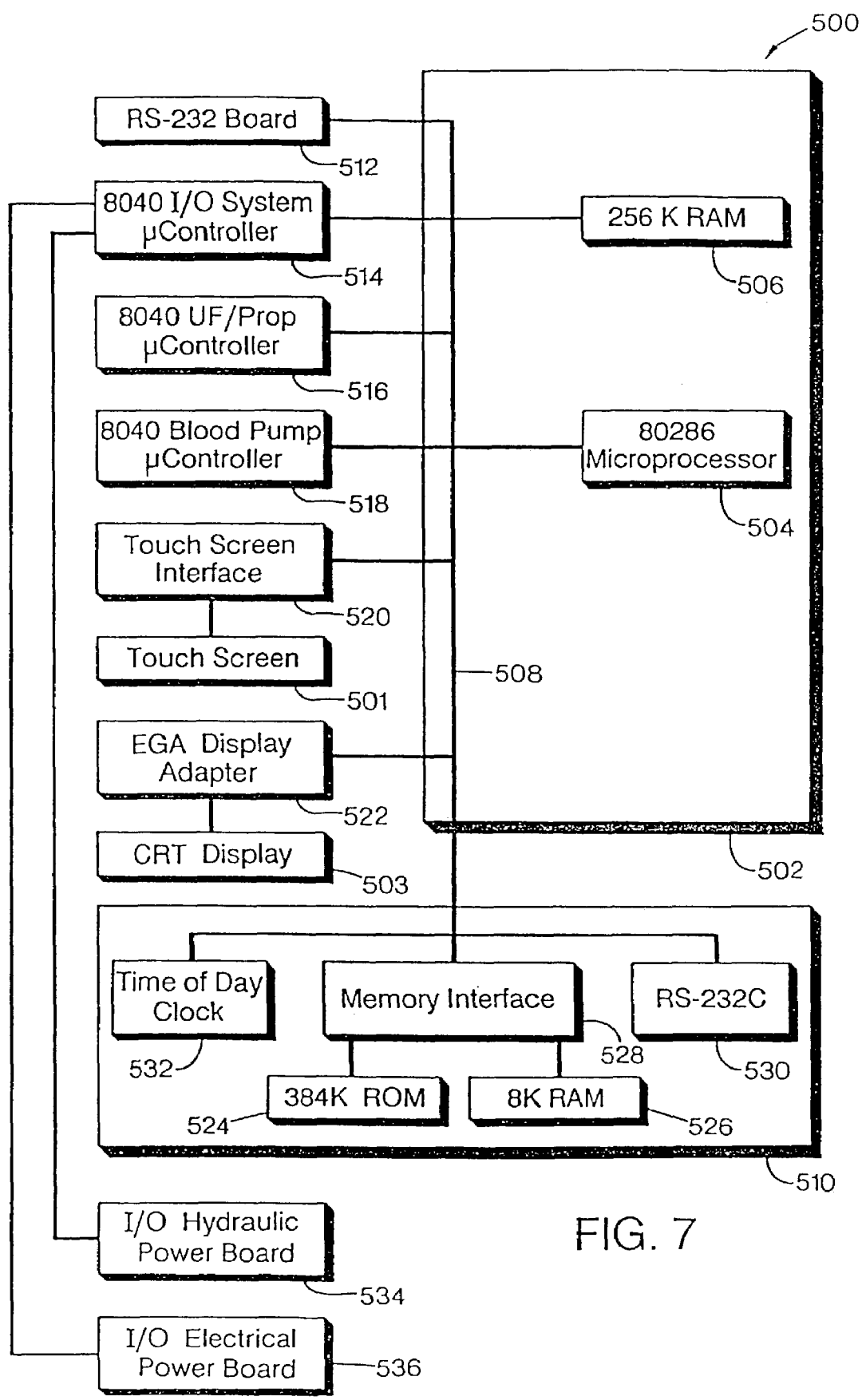
FIG. 7 shows a block diagram of a computer system used in the preferred embodiment.

FIG. 7 shows a block diagram of the computer system 500 that is used to control the touch screen 501, CRT display 503, and other components of the apparatus. This computer is programmed in the language 'C' in a conventional manner to accomplish the dialogue and other functions subsequently described.

Figure 8:
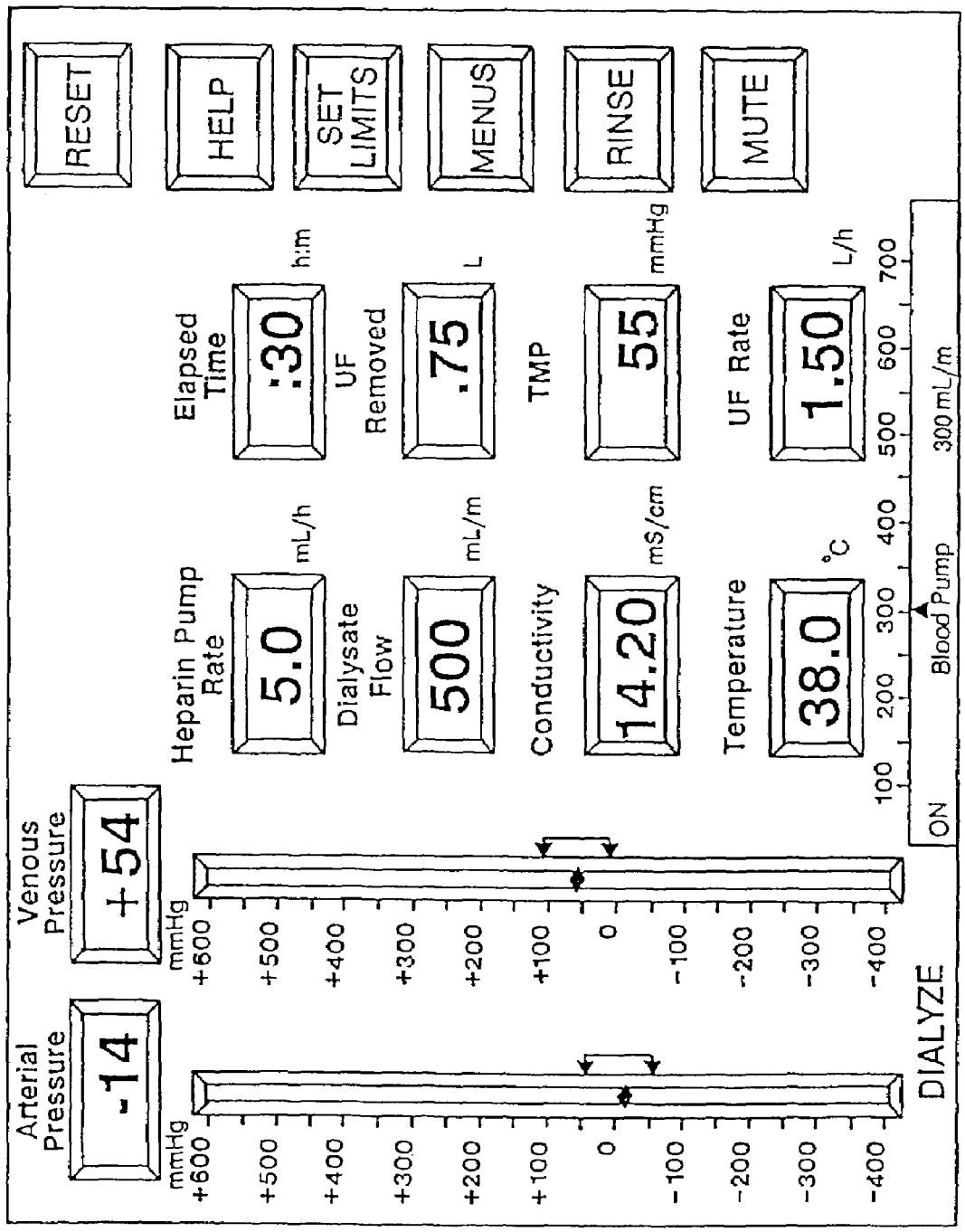
FIG. 8 shows a touch screen display used in the preferred embodiment.

FIG. 8 shows the touch screen display that is usually presented to the operator of the system of FIG. 7. As can be seen, the primary treatment parameters are displayed. These include the heparin pump rate, the dialysate flow rate, the dialysate conductivity, the dialysate temperature, the elapsed treatment time, the total ultrafiltrate removed, the transmembrane pressure, and the ultrafiltration rate. Also displayed are the patient's arterial and venous blood pressure (both in column of mercury form and in numeric form). A linear indicator at the bottom of the screen indicates the blood pump flow rate. A space at the top of the screen is reserved for alarm and help messages. These elements of the display are detailed more fully in Appendix A beginning at page Reference 1.

Most of these display elements are in a bordered box. The border serves as a visual alarm indicator and changes color and flashes if a corresponding alarm limit is violated.

A number of buttons are displayed on the right hand side of the display. The first is a RESET button and is used to reset alarm conditions after an alarm condition is corrected. HELP guides the user through a variety of help messages. SET LIMITS sets the alarm limits for various parameters including arterial pressure, venous pressure and TMP. MENUS replaces the buttons on the right hand side of the display with additional buttons corresponding to additional control functions, while maintaining the displayed parameters elsewhere on the screen. RINSE initiates the rinse mode, provided the interlocks are met. MUTE silences most audio alarms for 100 seconds. Additional buttons can appear in this part of the screen and are detailed in the Reference Section of Appendix A. Button locations are reprogrammable and can have multiple legends associated with them. Also, their positions on the touch screen can be varied by reprogramming.

Figure 9:
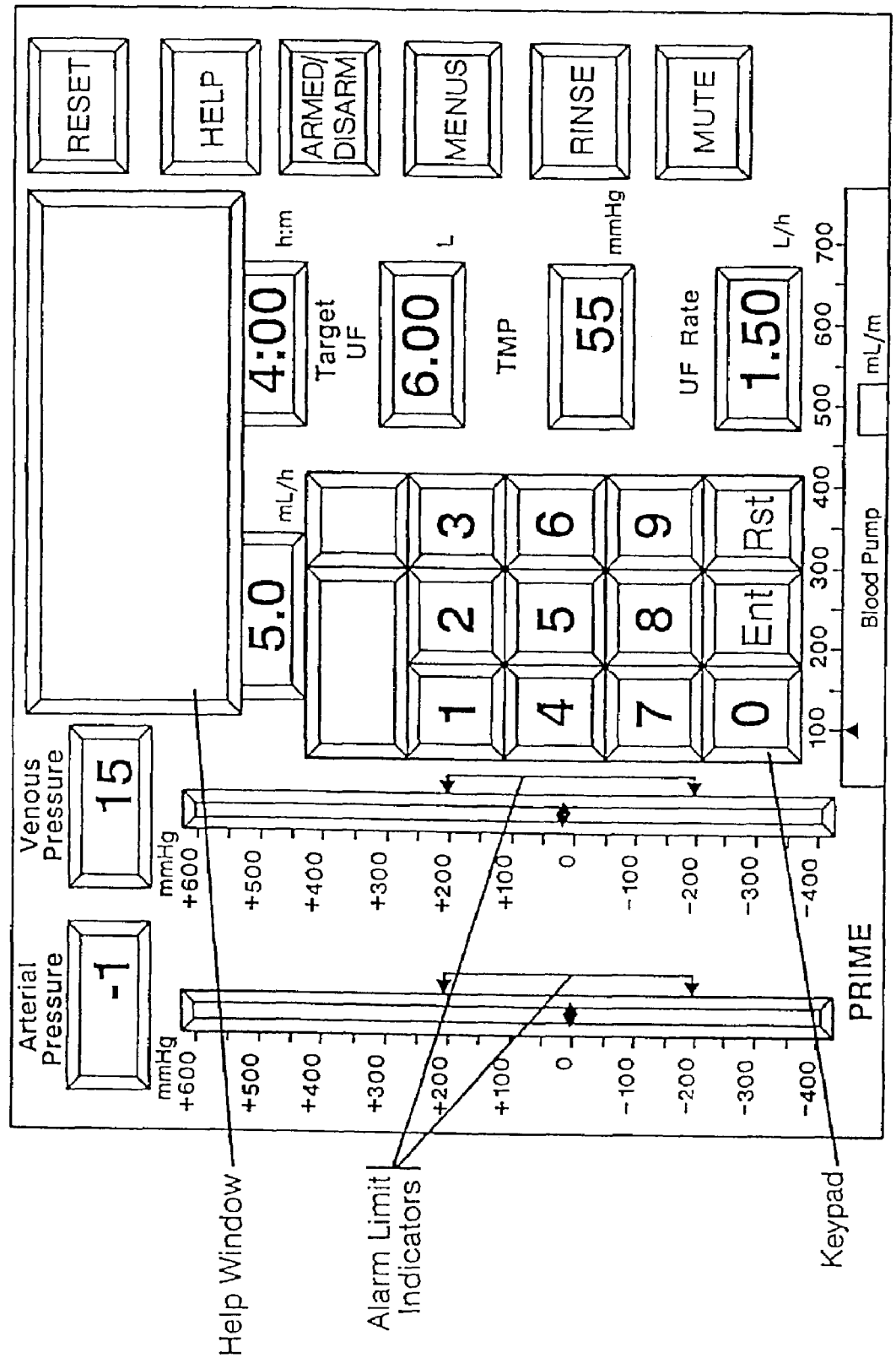
FIG. 9 shows the touch screen of FIG. 8 with a calculator window for data entry.

If it is desired to change one of the displayed parameters, such as the heparin pump rate, the operator simply touches the corresponding indicator. A calculator-like keyboard then pops up in a window superimposed on the display, as shown in FIG. 9. On this keyboard, the user can enter the new value for the selected parameter. Once the desired parameter is entered in this fashion, the operator presses ENTER on the calculator display and the calculator display disappears. The revised parameter is substituted in the corresponding indicator (with its border highlighted) and the user is prompted, through a button that appears at the lower right hand side of the screen, to verify the entered change. If the VERIFY button is not touched shortly after displayed, the VERIFY button disappears and the machine continues with its previous parameter. If timely verified, the change takes effect. In the preferred embodiment, the user has between one and five seconds to verify the parameter.

Some parameters are not susceptible to representation by a single number displayed in a parameter window. Exemplary are parameters that are programmed to change over time (so-called profiled parameters). In this class are the sodium concentration of the dialysate solution, the bicarbonate concentration of the dialysate solution, kT/V, and the ultrafiltration rate.

Figure 10:
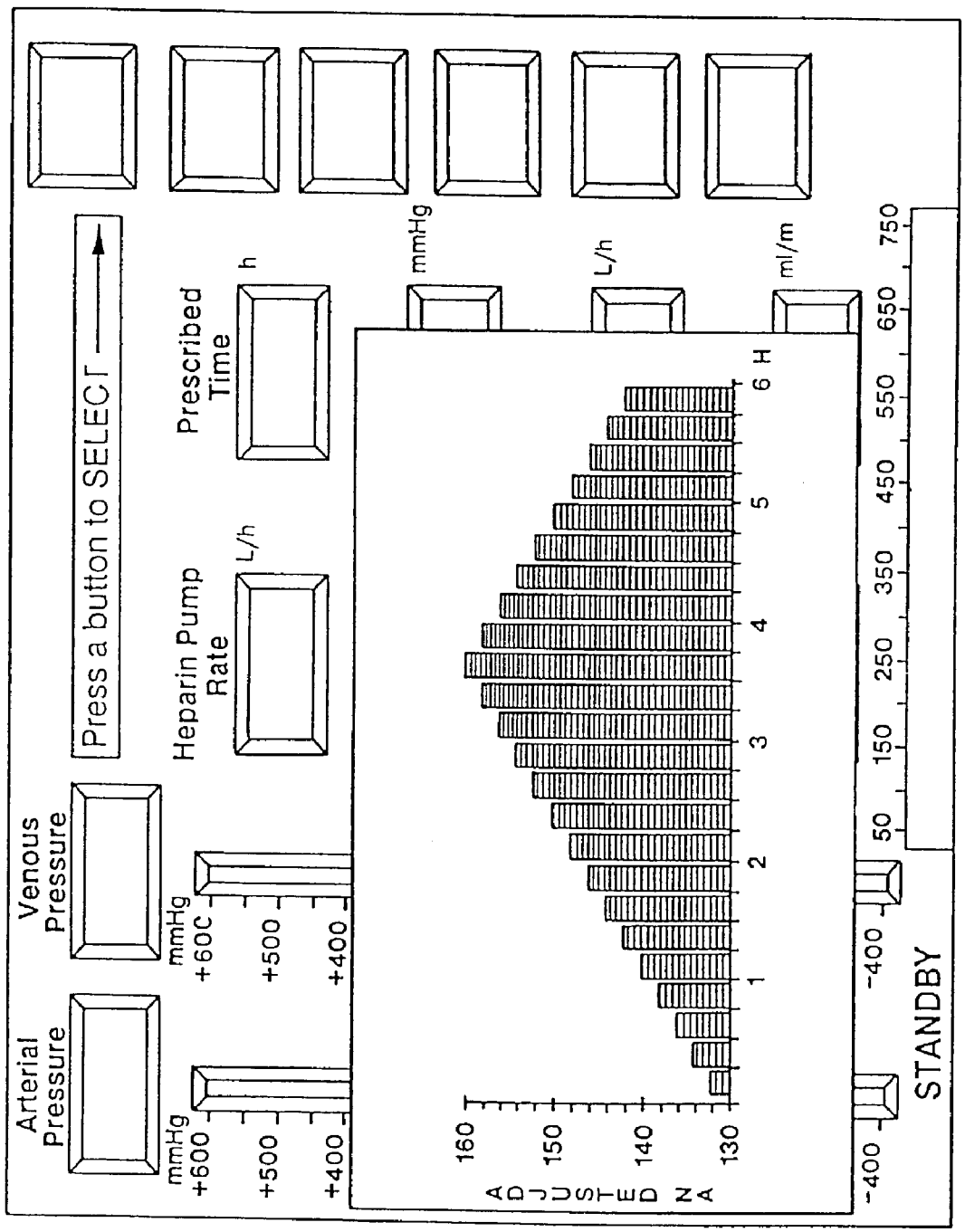
FIG. 10 shows a profile entry screen used in the preferred embodiment.

In the preferred embodiment, such profiled parameters are selectably displayed in the form of bar graphs on the display screen. Using sodium as an example, the Y-axis represents sodium concentrations in the range of 130-160 mEq/L. The X-axis represents the treatment period, broken down into fifteen minute intervals. Such a display is shown in FIG. 10.

The use of bar graphs to display profiled parameters is known in the art. The prior art fails, however, to provide a convenient manner by which data characterizing the profile curve may be entered into the machine. Typically, such data entry has been accomplished through a keypad on which data for each discrete time period is entered. However, this approach requires dozens of key presses and provides numerous opportunities for error.

In the preferred embodiment, in contrast, profiled parameters are entered by simply tracing the desired profile curve on the touch screen.

Figure 11:
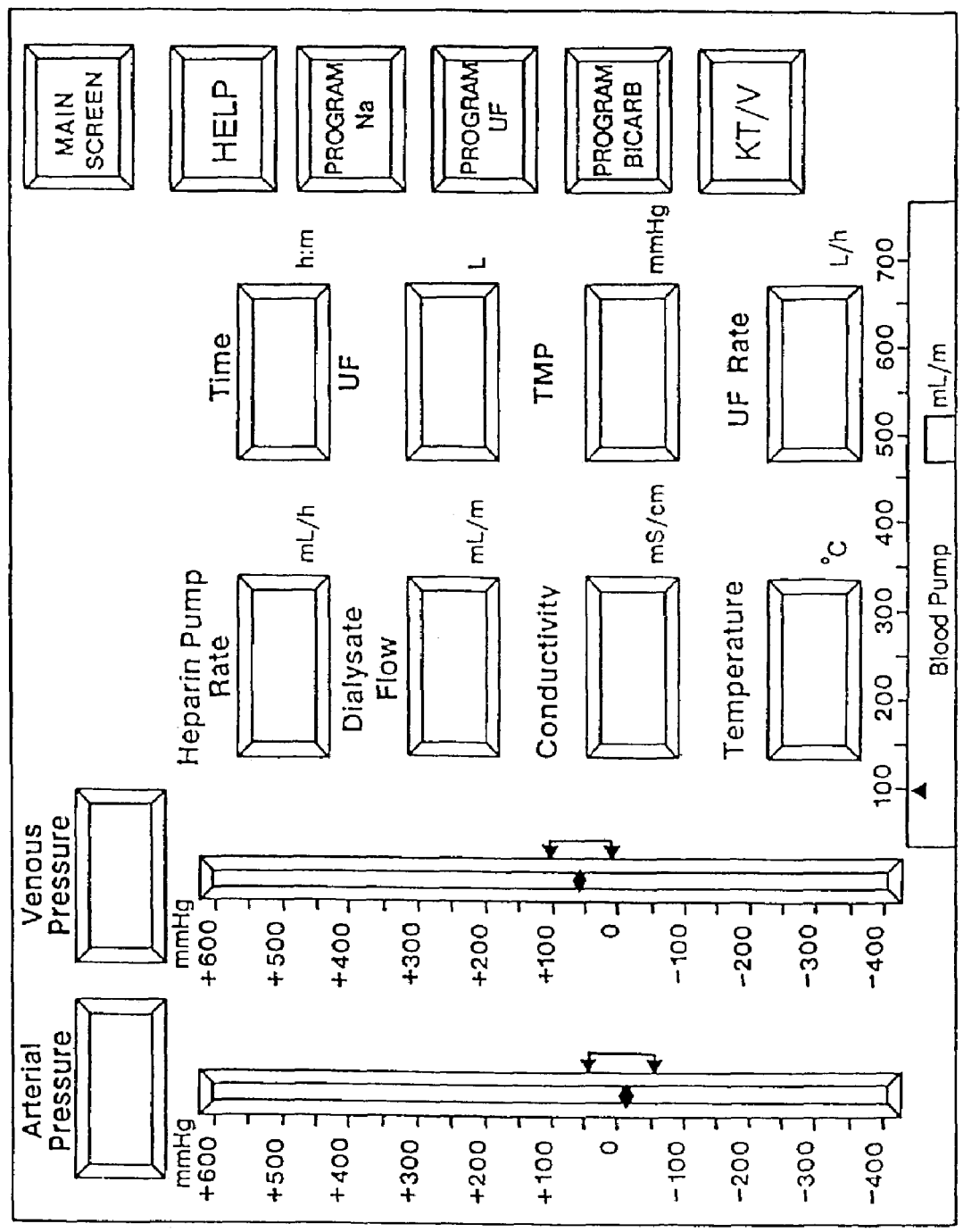
FIG. 11 shows a programming screen used in the preferred embodiment.

In more detail, programming of profiled parameters is performed as follows:

From the main touch screen display of FIG. 8, the user presses MENUS. The programming screen of FIG. 11 then appears, which includes along its right hand side buttons corresponding to the programming of sodium, bicarbonate, kT/V, and ultrafiltration. The parameter desired to be programmed is then selected by touching the corresponding button.

In response to this touch, the screen of FIG. 10 appears. If a profile has already been programmed, it is displayed in bar graph fashion on this screen. Otherwise, the graph is empty.

Before permitting the user to program the sodium profile, the machine first solicits the sodium value of the sodium concentrate being used. This data is entered on a pop-up keypad. If the treatment time was not earlier programmed, the machine also solicits this data by means of a pop-up keypad.

The user then traces the desired profile curve on the touch screen, and the computer virtually simultaneously displays a series of bars corresponding to the traced curve.

Alternatively, the user can touch the screen at discrete points on the desired profile curve. To program a linear increase in sodium from 140 to 160 mEq/L, for example, the user would touch the graph at 140 at the ordinate corresponding to the beginning of the treatment to interval, and 160 at the ordinate corresponding to the end of the treatment interval. The computer would then fit a linearly increasing series of bars between these points.

Discrete touches can also be used to program stepped profiles. If the first hour of treatment is to be at 150 mEq/L and the second hour is to be at 135 mEq/L, the user would first touch the screen at 150 at the ordinate corresponding to the beginning of the first hour. At the ordinate corresponding to the end of the first hour, the user would press at two locations. First at 150 (to cause the computer to fill in the intervening period with bars corresponding to 150), and again at 135. Finally, the user would touch the screen at 135 at the ordinate corresponding to the end of the second hour. The computer would then fill in the second hour with bars corresponding to 135.

After the desired profile curve has been entered, the ENTER button is pressed to set the program in the machine.

In the preferred embodiment, the computer "snaps" the height of each bar to one of a series of discrete values. In the case of sodium, these discrete values are spaced in 1 mEq/L steps.

Displayed on the screen during this programming operation is a numeric data window in which the numeric counterpart to a particular bar may be displayed. When the curve is first traced, the computer displays in this window the numerical parameter corresponding to each bar as it is defined. After the profile has been programmed, the numeric counterpart to any bar can be displayed by first touching a LOCK button that locks the curve, and then touching the bar in question.

After the profile has been set, the user may wish to alter it in certain respects. One way, of course, is to simply repeat the above-described programming procedure. Another is to adjust the height of a particular bar. This can be accomplished in one of two ways. The first is simply to touch the bar to be altered. The height of the bar tracks movement of the user's finger. The second way of adjustment is to first select a bar to be adjusted by repeatedly touching (or pressing and holding) a Right Arrow button until the desired bar is highlighted. (The Right Arrow button causes highlighting to scroll through the bars, left to right, and cycles back to the left-most bar after the right-most bar. The highlighting indicates the bar that is selected.) The numeric parameter corresponding to the selected bar is displayed in the numeric data window. This value can then be adjusted by Up and Down arrow keys that cause the displayed parameter to increase and decrease, respectively. In the preferred embodiment, the Up and Down arrow keys cause the sodium parameter to change in steps of 0.1 mEq/L, one-tenth the resolution provided in the original data entry, procedure. A similar ratio holds with other parameters programmed in this fashion. Again, the ENTER button is pressed to complete the programming operation.

As with other parameters, profiled parameters must also be verified before they take effect.

After the above-detailed data profiling operations are completed, data corresponding to the programmed profile is stored in the computer's memory. Periodically, such as once every fifteen minutes, a timed interrupt in the system's software program causes the computer to poll this memory for the value of the programmed parameter for the next time interval (here fifteen minutes). The physical parameter is adjusted accordingly using conventional adjustment mechanisms.

Once treatment has begun, the system only permits bar graph-bars corresponding to upcoming time intervals to be programmed. Bars corresponding to past time intervals reflect treatment history and cannot be changed. To readily distinguish past from future, the bars corresponding to each are displayed in different colors.

Additional details on sodium programming, as well as details of bicarbonate and ultrafiltration programming, are contained in Appendix D.

In all aspects of the interface, the user is guided from one touch to the next by a feature of the preferred embodiment wherein the button that the user is most likely to press next is highlighted. For example, when the machine is in Rinse mode and is nearing completion of these operations, the Self-Test button is highlighted, indicating that this is the next likely operation. Similarly, when the Self-Test operation is nearing completion, the Prime button is highlighted. By this arrangement, even novice users are easily guided through the machine's various phases of operations.

In addition to the above-described user interface, communications with the dialysis machine can also be effected by an RS-232C serial data interface 530 and by a data card.

Data cards (also known as memory cards or RAM cards) are known in the art, as represented by U.S. Pat. Nos. 4,450,024, 4,575,127, 4,617,216, 4,648,189, 4,683,371, 4,745,268, 4,795,898, 4,816,654, 4,827,512, 4,829,169, and 4,896,027, the disclosures of which are incorporated herein by reference. In the preferred embodiment, a data card can be used both to load treatment parameters into the machine and to download logged patient parameters from the machine for therapy analysis.

Among the treatment parameters that can be provided to the machine by a data card are the ultrafiltration profile, the sodium profile, the bicarbonate profile, the blood pump flow rate, the treatment time, the desired ultrafiltration removal volume, the dialysate flow rate, the dialysate temperature, the blood pressure measurement schedule and alarms, and the heparin prescription.

Among the patient parameters that are logged by the machine and that can be downloaded to a memory card for later therapy analysis are: temporal data relating to dialysate temperature and conductivity (both of which are typically measured at several points in the fluid circuit), venous, arterial, dialysate, systolic and diastolic pressures, blood flow rate, total blood processed, ultrafiltration rate, total ultrafiltrate removed, the ultrafiltrate goal, and the machine states.

Additionally, the data card can convey to the machine certain codes that, when read by the machine, initiate special operations. These operations include calibration mode, technician mode, enabling the blood pressure monitoring function, modifying the parameters transmitted over the serial port for diagnostics, and others.

The card used in the preferred embodiment is commercially available from Micro Chip Technologies under the trademark ENVOY and provides 32K of data storage in EEPROM form. Similar cards are also available from Datakey.

When a card containing treatment parameters is read by the machine, the stored parameters do not immediately take effect. Instead, each is displayed on the screen and the operator is asked, through prompts that appear on the screen, to verify each individually. If a parameter is not verified, that aspect of machine operation is left unchanged. In the preferred embodiment, the parameters loaded from a memory card are displayed in their respective parameter windows and each is highlighted in sequence, with the system soliciting verification of the parameter in the highlighted window.

In alternative embodiments, a plurality of parameters are be displayed for verification as a group.

Returning now to FIG. 7, the computer system 500 that controls the user interface and other aspects of machine operations is built around an IBM-AT compatible motherboard 502 that includes an Intel 80286 microprocessor 504 and 256K of RAM 506 interconnected by an AT bus 508. Into expansion slots in this motherboard plug seven additional boards: a memory board 510, an RS-232 board 512 (which is dedicated to controlling a patient blood pressure monitor), an Input/Output system controller board 514, an ultrafiltration/proportioning system controller board 516, a blood pump system controller board 518, a touch screen interface board 520, and an EGA display adapter board 522.

The computer system has five primary responsibilities: (1) user interface (i.e., through the CRT display and the touch screen); (2) state machine control (i.e., rinse, prime, dialyze, etc.); (3) microcontroller communications; (4) conducting of self-tests; and (5) calibrations. These functions are carried out by the AT-computer in conjunction with the above-listed expansion boards.

Turning now to a more detailed description of each component, the memory board 510 contains the firmware for the 80286 microprocessor. The memory board can hold up to 384K of read only memory (ROM) 524 and 8K of nonvolatile static random access memory (RAM) 526. Also included on the memory board is a memory interface 528, an RS-232C interface 530, and a time of day clock 532. The interface 528 is conventional and simply handles the addressing of memories 524 and 526. The RS-232C interface is for general purpose use (as opposed to the RS-232 interface 512 that is dedicated to use with a blood pressure monitor) and is typically used to remotely provide programming instructions to, and to interrogate patient treatment data from, the machine. The time of day clock 532 is used, inter alia, to time/date stamp patient data as it is acquired and to provide a time of day reference by which automated machine operations (such as unattended warm-up) may be controlled.

The host control program is written in the 'C' programming language. This code is compiled, linked and loaded into the ROM 524. The purpose of the host control program is to:

Gather data from the Input/Output, Blood Pump and Ultrafiltration controller sub-systems, and output control functions to the various controller sub-systems;

Input data from the user interface touch screen;

Monitor the data for violation of alarm limits and usage operating conditions, and to set the appropriate program alarm condition indicators;

Evaluate the data to determine the current operating state of the control program, i.e., Standby, Rinse, Self-Test, Prime, and Dialyze; and Update the display data to the CRT portion of the user interface.

The RAM memory 526 is used to store calibration and machine parameters.

In order for the memory board to operate without conflict with the host AT-motherboard, the motherboard must be modified by disabling the data buffers above address 256K. The memory controller's ROM space is mapped into the address space from 256K to 640K, with the portion between 256K and 312K being mapped also to address range 832K to 888K. The code at this upper address range is configured as a BIOS extension, which results in the ROM being given control by the motherboard's BIOS software following power-on initialization. Unlike the standard BIOS extensions, the host code does not return to the BIOS after being given control.

The RS-232 board 512 permits computerized remote control of a patient blood pressure monitor. Suitable blood pressure monitors that are adapted for RS-232 control are available from Spacelabs of Hillsboro, Oreg.

The touch screen interface board 520 is commercially available as part number E271-400 from Elographics and is designed to operate with the E272-12 touch panel 501 that is used in the preferred embodiment. The function of the interface board 520 is to translate signals returned from the touch screen into a data format suitable for use by the 80286 microprocessor 504. Terminate and stay resident software for driving the interface board 520 is available from Elographics.

The EGA display adapter card 522 is conventional and provides RGB signals to the CRT display 503.

The three microcontroller subsystems (the blood pump system 518, the ultrafiltration/proportioning system 516, and the I/O system 514) are particularly detailed in the following discussion.

Blood Pump System

The blood pump controller 518 is built using an Intel 8040 microcontroller and is responsible for controlling or monitoring five subsystems. They are (1) the blood pump; (2) the blood pressure measurement (arterial, venous and expansion chamber): (3) heparin delivery: (4) level adjust; and (5) ambient temperature. The blood pump controller operates in conjunction with a blood pump power board (not shown) that controllably provides operating power to devices controlled by the blood pump controller.

In still more detail, the primary operation of the blood pump controller 518 is to supply power to the blood pump motor such that the pump head will turn and pump at a rate selected by the operator.

The blood pump controller system consists of the following major components:

| Description | Location |
| --- | --- |
| User parameter entry | Host controller |
| Software Speed Error Control | Blood Pmp Controller |
| Hardware Speed Error Control | BP Power Board |
| Optical speed sensor | On motor shaft |
| Motor Power Driver Circuitry | BP Power Board |

The operator enters the desired blood pump rate information on the video screen (CRT) touch panel. The host controller (80286 microprocessor) converts this information to the appropriate motor rate which it then sends to the Blood Pump controller (8040) on the Blood Pump controller board. The 8040 controller converts the motor rate information to an analog level, which is fed to a motor speed control IC (LM2917-8) on the Blood Pump Power board.

An optical speed sensor is mounted on the rear shaft of the blood pump motor, with an LED being positioned on one side of the shaft, and a photo transistor on the opposite side. The shaft has two holes drilled through it, with each hole being perpendicular to the shaft and to each other. This results in four optical pulses received per shaft revolution.

This tachometer signal is monitored by both the LM2917-8 and the 8040 controller. The LM2917-8 provides quick responding speed control by comparing the motor speed with the desired speed information from the 8040. The result of this comparison is an error signal which provides an input to the motor power driver circuit.

The motor power driver provides a +24 V pulse width modulated drive to the motor at a frequency of approximately 30 KHz. This drive is current limit protected, to prevent damage in the event of a stalled motor.

The 8040 compares the tachometer motor speed information with the desired speed commanded by the 80286 and corrects the level provided to the LM2917-8 accordingly. In this way the 8040 guarantees the ultimate accuracy of the pump, with the LM2917-8 circuit not requiring any calibration. In addition, the 8040 can monitor for control problems, such as under speed or over speed, which may result from failures in the LM2917-8 or motor drive circuitry.

The 8040 also monitors the motor speed independent of the tachometer signal using the motor's back EMF. Periodically (every 0.5 second) the motor drive is turned off for approximately 6 millisecond and the voltage at the motor terminals is measured. Though this does not result in as precise an indication as the tachometer signal, gross failures can be determined, such as when the tachometer signal is lost.

Blood Pressure Measurement

The blood pressure measurements include the venous, arterial and expansion chamber (for Single Needle treatment) pressures. All three measurement systems include identical hardware. Each pressure is sensed by a SenSym SCX15 gauge sensing pressure transducer mounted to the Blood Pump Power board. Each transducer is connected to a differential amplifier designed to provide a measurement range from −400 to +600 mmHg. The output of each amplifier drives an A/D input channel of the Blood Pump Control system, at which point it is converted to a 10 bit digital value. The calibration of each of the pressure inputs is handled entirely in software, requiring that the design of each amplifier guarantee that its output remain within the A/D input range of 0 to +5 V over the input pressure range and over all component tolerances.

Heparin Delivery

Heparin delivery is accomplished by stepping a stepper motor which rotates the pinion of a rack and pinion mechanism. The pinion moves the rack, and the mechanical fixture is such that the plunger of the heparin syringe moves the same distance. The stepper motor is controlled by the 8040 microcontroller located on the Blood Pump Controller board 518. When the operator enters a desired heparin rate in milliliters per hour (mL/h) via the front panel touch screen, the host 80286 microprocessor converts this information to the appropriate motor step rate and passes it to the Blood Pump microcontroller. The Blood Pump microcontroller outputs a motor step rate logic signal to the Blood Pump Power board where the heparin motor power drive circuitry energizes the appropriate stepper motor coil.

The motor step rate logic signal from the Blood Pump microcontroller 518 is also input to the I/O Controller board 8040 microcontroller 514. The I/O microcontroller monitors this signal to determine if the heparin motor is going the appropriate speed. If it determines that an overspeed condition exists, it disables the heparin motor via a disable line that goes to the Blood Pump Power board.

There are two optical sensors to provide information about the state of the heparin pump. The disengage sensor detects when the front panel syringe holder arm is in the disengage position. The end-of-stroke sensor detects when the pinion is raised up on the rack, which occurs when the gear teeth are not meshed. This is an indication of an overpressure condition. The Blood Pump microcontroller monitors the state of these sensors and passes the information to the host 80286 microprocessor.

Level Adjust

The level adjust system allows the operator to change the blood level in the arterial and venous drip chambers. A level up and level down button exists for each drip chamber. The 8040 microcontroller on the Blood Pump Controller board 518 monitors the button positions. When a button is pressed, a valve selects that drip chamber power is supplied to the motor such that the pump head of a peristaltic pump rotates to apply a positive or negative pressure to the drip chamber. The software logic only accepts one button press at a time. If two buttons are pressed simultaneously, both are ignored.

The motor drive circuitry is located on the Blood Pump Power Board. The motor may be driven in the forward or reverse direction. A direction signal from the Blood Pump Controller Board, along with a pulse width modulated motor rate signal controls two bipolar half bridge motor drivers. Both half bridge motor drivers receive the same motor rate signal, while the motor direction signal is high at one and low at the other to determine the direction the motor runs. The half bridge drivers provide a 24 V pulse width modulated drive voltage of approximately 30 KHz to the motor.

Other details of the level adjusts are described hereinbelow.

Ambient Temperature Control

The purpose of the cabinet cooling system is to keep the internal temperature of the cabinet lower than the 50° C. maximum temperature at which the electronic components are guaranteed to operate. (Most electronic components are rated to operate at 60° C., the exception is the solid state relay used for heater control.) A fan is located at the base of the cabinet and exhausts the warm cabinet air. An intake vent for the ambient room temperature is located below the CRT on the back of the machine.

The cabinet cooling system consists of the following major components:

| Description | Location |
|---|---|
| Cabinet Fan | Base of cabinet |
| Blood Pump Temperature IC | Blood Pump Power Board |
| Misc I/O Temperature IC | Misc I/O Electronics Pwr Bd. |
| Software Fan Control | Host controller |
| Cabinet Fan Drive | Blood Pump Power Board |

The two LM35DZ temperature ICs are located on the Blood Pump and Misc I/O Electronics power boards. This IC outputs a voltage linear with temperature in ° C. (10.0 mV/° C.). These temperature readings are input to the fan control software.

The fan control software always responds to the higher of the two temperatures. Typical values are as follows. At 46° C. the fan turns on in the low speed mode and at 48° C. it turns on in the high speed mode. There is a 2° C. of hysteresis at these threshold temperatures, i.e., the fan returns to low speed at 46° C. and turns off at 44° C. In addition, at 60° C. a cabinet temperature alarm occurs that results in the machine shutdown state.

The fan power driver is located on the Blood Pump Power board. A motor rate signal from the Blood Pump Controller board determines the duty cycle of a 30 KHz pulse width modulated signal. This signal is input into a passive filter to provide a DC signal to the motor.

UF/Proportioning Control System

The ultrafiltration/proportioning (UF/PROP) controller 516 is built using an Intel 8040 microcontroller and is responsible for controlling the systems associated with ultrafiltration and dialysate preparation. This controller operates in conjunction with an ultrafiltration/proportioning power card (not shown) that controllably provides operating power to devices controlled by the ultrafiltration/proportioning controller. Six subsystems are controlled or monitored by the UF/Proportioning controller 516. They are:
 a. Temperature Control
 b. Proportioning Control
 c. Flow Control
 d. UF Removal Control
 e. Conductivity Monitoring
 f. Temperature Monitoring Temperature Control The UF/PROP system 516 controls the dialysate temperature by enabling a zero voltage crossing solid state relay, which provides the power to a 1500 W heater (item 18 in FIG. 1A), with a 5 Hz pulse width modulated digital signal (heater-enable signal). The duty cycle of the heater-enable signal is updated every 0.5 seconds with the sum of the past duty cycle and a temperature error correction value. The correction value is proportional to the difference between the desired temperature (stored by the host) and the measured control temperature (measured immediately down stream of the heater housing).

The host-determined desired temperature is calculated using the user-entered desired temperature and the stable "B" conductivity probe (item 46 in FIG. 1B) temperature. If the stable "B" conductivity probe temperature is different from the user-entered desired temperature by more than 0.05° C., then the control temperature threshold sent to the UF/PROP controller is updated so that the "B" conductivity probe temperature will equal the user-entered desired temperature. In this way, the dialysate temperature at the "B" conductivity probe will be adjusted so that flow rate and ambient temperature effects on the "B" conductivity probe temperature (and the primary temperature, displayed on the video screen) will be compensated. This control temperature adjustment is performed a maximum of every 5 minutes.

Proportioning Control

The UF/PROP system 516 controls the concentrate(s) to water proportioning ratios by controlling the dialysate flow rate, the "A" concentrate 5 flow rate, and the "B" concentrate flow rate.

The "A" and "B" concentrate pumps (items 22 and 40, respectively, in FIG. 1A) are stepper-motor driven (each by a cam/follower) diaphragm pumps which deliver a calibrated volume of concentrate per stepper motor revolution. Their flow rates are controlled by controlling the speed of the stepper motors. The concentrate pumps are unidirectional and utilize the proper actuation of a three-way valve for their intake and output pumping strokes. The intake stroke is synchronized by a signal that is generated by an optical interrupter sensor which senses a pin mounted on the cam of the pump assembly. Further details pertaining to the "A" and "B" concentrate pumps are described hereinbelow.

The UF/PROP controller 516 utilizes the fact that the stepper motors require 200 motor steps per revolution (between each synchronization pulse) to check the concentrate pumps for stepping errors. If late or early synchronization pulses are received then the associated error conditions are reported on the screen during the Technician Mode of the machine (further details provided hereinbelow).

During the Rinse Mode, the host determines the concentrate treatment mode based on the "A" and "B" rinse port interlock information (further details provided hereinbelow). If the "B" concentrate line (FIG. 1B item 104) is not coupled to the "B" rinse port (FIG. 1A, item 30), a bicarbonate treatment is initiated by setting the proportioning ratios and the conductivity alarm limits appropriately. Conversely, if the "B" concentrate line is coupled to the "B" rinse port, an acetate treatment is initiated (further details provided hereinbelow). Using the dialysate flow rate and the proportioning ratios, the host determines the associated concentrate flow rates and stores the concentrate pump speeds in the UF/PROP controller. The proportioning mode (for acetate or bicarbonate dialysis) cannot be changed in the Prime or Dialyze Modes.

The control of the dialysate flow rate is described in the following Flow Control section of the UF/PROP controller description.

Flow Control

The UF/PROP system 516 controls the dialysate flow rate by controlling the time between the switching of the flow equalizer (FIG. 1B, item 54) valves (provided that all the fluid within the flow equalizer chambers has been exchanged).

The average flow equalizer volume is calibrated (measured) during the Calibration Mode. The time between the switching of the flow equalizer valves (FIG. 1B, items 142-149) is scaled by the host (according to the calibration constant) and stored in the UF/PROP controller so that the user entered desired dialysate flow rate is achieved.

To guarantee the complete fluid transfer to/from the flow equalizer chambers (FIG. 1B, items 126, 128) two flow sensors (FIG. 1B, items 58, 59; described in further details hereinbelow) are located within the fluid path to detect the absence of dialysate flow. The time at which both sensors detect no flow has been defined as end of stroke. The end-of-stroke time has been defined as the time between the moment an end of stroke was sensed and the desired flow equalizer valve switch time. Since the supply pump speed controls the instantaneous dialysate flow rate, the UF/PROP controller servos the supply pump speed in order to maintain a consistent end-of-stroke time.

Since the flow equalizer volume is calibrated and the end-of-stroke time is controlled, the UF/PROP system 516 can accurately control the dialysate flow rate to the user-entered value.

UF Removal Control

The UF/PROP system 516 controls the UF removal rate by controlling the time between the switching of the UF flow meter valves (FIG. 1B, items 142-149). The UF/PROP system controls the accumulated UF volume by counting the number of UF flow meter strokes.

Since the UF flow meter volume is calibrated (measured) in the Calibration Mode, the rate which the host (80286 microprocessor) passes to the UF/PROP controller (number of seconds between valve switches) is scaled so that the user-entered UF removal rate is achieved.

In the same way, the user-entered UF removal volume is scaled by the UF flow meter's stroke volume to a number of UF meter strokes. The host passes the number of UF meter strokes to the UF/PROP controller. The UF/PROP controller will then switch the UF flow meter valves and decrement the stroke number, at the desired rate, as long as the stroke number is greater than zero. The host can then calculate the UF removal volume accumulated by subtracting the number of UF flow meter strokes remaining, scaled by the stroke volume, from the operator-entered desired UF removal volume. The accumulated volume is displayed during the Dialyze Mode. This value remains during the Rinse Mode and is cleared upon the entry of the Self Test Mode.

In Rinse, the UF removal rate is 3.6 L/h and the video screen indicates no UF volume accumulated. During the Self Test Mode, no UF removal occurs except during specific self tests performed by the machine (no UF volume is accumulated). In the Prime Mode, the UF removal rate is set by the operator and is no greater than 0.5 L/h (no UF volume is accumulated). During the Dialyze Mode, the UF removal rate is set by the operator and is limited to between 0.1 and 4.00 L/h. For UF removal to occur in the Dialyze Mode the following conditions must be met:
  1. A target UF volume and a UF rate have been entered (or treatment time and target UF volume have been entered and a machine-calculated UF rate is used).
  2. The blood pump is pumping.
  3. The target UF volume has not been reached.

Conductivity Monitoring

Conductivity is used as a measurement of the electrolyte composition of the dialysate. Conductivity is usually defined as the ability of a solution to pass electrical current. The conductivity of dialysate will vary due to the temperature and the electrolyte composition of the dialysate.

The UF/PROP system measures conductivity at two locations (conductivity probes) in the hydraulic circuit using alternating-current resistance measurements between each of the conductivity probes' electrode pairs. The two flow path locations are at the "A" conductivity probe (FIG. 1A, item 38) and the "B" conductivity probe (FIG. 1B, item 46).

One electrode of each of the probes is stimulated with a 1 kHz ac voltage while the other is held at virtual ground (current sense electrode). Two voltages are produced by the resistance measurement circuit. The ratio of the voltages is proportional to the resistance of the respective probe. The resistance of the probes has been modeled as a function of temperature and conductivity. Since each of the conductivity probes contains a thermistor, the temperature at each of the probes is known. Using the model that was derived for the probes, the temperature measured at the probes, and the resistance measured at the probes the conductivity is calculated.

Each conductivity probe is calibrated during the Calibration Mode, at which time the resistance of each probe is measured at a known conductivity and temperature (by the use of an external reference meter) for the scaling of the probe's base resistance in the relationship described previously.

The UF/PROP system 516 generates alarms from the measured conductivities at the "A" and "B" probes. Since these conductivity alarms are used to verify the proportioning ratios, the alarms are generated by testing the "A" conductivity and the "B" portion of the total conductivity ("B" portion="B" conductivity–"A" conductivity). The alarm limits are determined from the concentrate treatment mode and are stored in the UF/PROP controller by the host. Therefore only during a bicarbonate dialysis treatment would the host store a non-zero expected "B" conductivity portion.

The host determines the concentrate treatment mode during the Rinse Mode by reading the "A" and "B" rinse port interlock information. If the "B" concentrate line is not on the "B" rinse port; a bicarbonate treatment is initiated by setting the proportioning ratios and the conductivity alarm limits appropriately. Conversely, if the "B" concentrate line is coupled to the "B" rinse port, an acetate treatment is initiated. Upon exiting the Rinse Mode the concentrate treatment mode is set for the remainder of the dialysis treatment (concentrate treatment mode is only adjusted in the Rinse Mode).

Temperature Monitoring

The UF/PROP system 516 measures the dialysate temperature at three locations in the fluid path. The first location is directly after the heater (FIG. 1A, item 18) and this thermistor, the heater thermistor (FIG. 1A, item 20), is used for the primary temperature, control feedback. The next two thermistors (FIG. 1A, item 110 and FIG. 1B, item 124) are contained in the "A" and "B" conductivity probes (FIG. 1A, item 38 and FIG. 1B, item 46, respectively). These temperatures are used to temperature-compensate the "A" and "B" conductivity measurements. The "B" conductivity temperature is also used to generate a backup high temperature alarm.

The temperature measurement circuit used throughout the machine consists of a voltage divider with a Thevenin Equivalent circuit of 3062 Ω in series with a 7.55 V supply. The voltage divider circuit when connected to the thermistor used in the temperature measurement system referenced to ground produces the voltage to temperature relationship of $T(° C.)=(3.77V-Vtemp)(12.73)(° C./V)+37° C.$ The tolerance on the component parameters used in the temperature measurement system can be as great as 10%, therefore the temperature-to-voltage relationship must be calibrated. Calibration of the temperature measurements is a two-point calibration done at 30 and 40° C. The calibration procedure results in a calibration constant for both the slope and the offset for each temperature probe/circuit.

In the UF/PROP controller the voltage described above as Vtemp is measured for the three temperature probes in its system on a scheduled basis (every 0.2 seconds for the "A" and "B" temperatures and every 1 second for the heater temperature).

The temperature that is displayed on the video screen is measured at the primary ("dialysate") conductivity probe 60, located just before the bypass valve 66 (see FIG. 1B), by the I/O controller.

Input/Output Control System

Nine subsystems are controlled or monitored by the I/O control system 514. They are:
  Air detector
  Blood leak detector
  Dialysate pressure monitor
  Heparin pump overspeed monitor
  Bypass system and flow sensor
  Conductivity monitor
  Temperature monitor
  Line clamp
  Power fail alarm

Air Detector

The air detector assembly utilizes a set of 2 MHz piezo crystals. One crystal functions as an ultrasonic transmitter and the second crystal functions as a receiver. The transmitter and receiver are housed in separate but identical assemblies. There is a distance of 0.20 inch between these assemblies into which the venous blood line is placed during dialysis. The emitter is driven by a 2 MHz squarewave that is derived from a crystal oscillator located on an I/O Electrical Power board 536 that is connected to the I/O controller 514 by a ribbon cable. When there is fluid in the blood line between the crystal assemblies, the 2 MHz signal is coupled to the detector assembly. The return signal from the detector assembly is amplified and rectified by two independent circuits also located on the I/O Electrical Power board 536. These dc output levels are monitored using two different methods. The first method is the software generated alarm and the second is the hardware generated alarm.

Software Alarm Detection (Primary Alarm)

One output is fed from the I/O Electrical Power board 536 to an A to D converter and read by the 8040 microcontroller on the I/O Controller board 514. This value is averaged over a 400 msec time period and reduced by multiplying it by 15/16 and subtracting 50 mV (for noise immunity). This new value is then converted back to an analog level to be used as an alarm limit. This software generated limit is compared to the rectified dc signal from the detector. The output state of this comparator is monitored by the on-board 8040. When the unaveraged signal falls below the software generated limit for longer than a calibratable time period, an alarm occurs. Sensitivity of the software alarm is 10 microlitres at 300 mL/min blood flow.

Hardware Alarm Detection (Secondary Alarm)

The hardware alarm is redundant to the software generated alarm. This alarm uses two comparators on the I/O Electrical Power board 536. One comparator looks for a minimum dc level from the rectified detector signal which guarantees the presence of fluid in the venous tubing. The second comparator is ac-coupled to react to a large air bubble in the tubing. Sensitivity of this detector is approximately 300 microliters at 300 mL/min blood flow. Both comparator outputs are wire OR'd together so that either comparator will generate an alarm.

Blood Leak Detector

The detector assembly consists of a high-efficiency green LED and a photocell. These components are installed into a housing through which spent dialysate passes.

Both of these components connect to the I/O Hydraulic Power board. The LED is connected to a voltage-to-current converter on an I/O Hydraulic Power board 534 (which is also connected to the I/O controller 514 by a ribbon cable). The input to this circuitry comes from the I/O Controller board 514. The photocell is tied to the +5 V reference supply through a 750 k ohm resistor. This provides a voltage divider which is monitored on the I/O Controller board.

The current through the LED is adjustable and controlled via a D to A output from the I/O Controller board. The light intensity of the LED is adjusted to illuminate the photocell to a point where its resistance is below the alarm threshold. During a blood leak, the presence of blood in the housing attenuates the light striking the photocell which causes an increase in both the photocell resistance and voltage. The increase in voltage (monitored by the microcontroller on the I/O controller board) results in a blood-leak alarm.

Further details on the blood-leak detector are provided hereinbelow.

Dialysate Pressure Monitor

The dialysate pressure is sensed by a resistive bridge pressure transducer (FIG. 1A, item 64) located just upstream of the dialyzer. The transducer is connected to a differential amplifier circuit on the I/O Hydraulics Power board 534 designed to provide a measurement from -400 to +500 mmHg. The differential amplifier circuit also has an offset input that comes from a software calibratable variable, DAC_OFFSET. The output of the amplifier drives an A/D input channel of the I/O Controller system, at which point it is converted to a 10 bit digital value. The calibration of the pressure input is handled entirely in the software, requiring that the design of the amplifier guarantee that the output remains within the A/D input range of 0 to +5 V over the input pressure range and over all component tolerances.

Heparin Pump Overspeed Monitor

To ensure that the heparin pump does not exceed its set speed, the I/O controller board software monitors a clock signal from the Blood Pump Controller board that is equivalent to ¼th the heparin pump step rate. In the event that a heparin pump overspeed occurs, the I/O controller board disables the heparin pump via a hardware line that goes to the Blood Pump Power board and notifies the host of the alarm.

To determine if the heparin pump is running at the correct speed, the time required for ten clock signals to occur is measured (and stored in variable HEPTIMER) and compared against a minimum time period that is set by the host (HP_P_MIN). If the measured period is less than the host set limit, a normal-speed alarm occurs. The host is notified of the normal-speed alarm and the heparin pump is disabled via the hardware line to the Blood Pump Power board.

When the heparin pump rate changes, the host resets the minimum time period, HP_P_MIN, and the I/O controller waits for the first clock signal to restart the timer (this first clock is not counted as one of the ten). In this way, the alarm logic is resynchronized with the heparin pump stepper motor.

The I/O controller board 514 also monitors the total amount of heparin delivered in the high-speed bolus mode. When it receives clock signals at a rate faster than a predetermined speed, it assumes the pump is operating in the high-speed mode. It has a high-speed counter, H_SPD_CNTR, that is set by the host. If more high-speed counts occur than are in the counter, a high speed alarm occurs. The host is notified of the high-speed alarm and the heparin pump is disabled via the hardware line to the Blood Pump Power board.

Bypass System and Flow Sensor

The bypass mode is initiated when a primary dialysate alarm is detected by the I/O Controller board, when a redundant dialysate alarm is detected by the UF/PROP Controller board 516, when the host requests bypass, or when the manual bypass button is pushed.

The bypass valve (FIG. 1B, item 66) is in the bypass position when deenergized. It is driven from the nominal +24 V supply with a straight on/off transistor control on the I/O Hydraulics Power board.

To verify that there is not a failure in the bypass system, a flow sensor (FIG. 1A, item 62) located upstream of the dialyzer and just downstream of the bypass valve checks for flow. If flow exists during bypass, a Bypass Fail Alarm is triggered and the machine is put in the safe, nonfrmnctional, Shutdown state. If there is no flow when not in the bypass mode, a No Flow alarm is generated. (Further details on the flow sensor are provided hereinbelow.)

This flow sensor consists of two thermistors. The first is a reference thermistor used to determine the fluid temperature. The second thermistor uses thermal dilution to sense the fluid flow. The voltage outputs from the thermistors on the I/O Hydraulics Power board 534 drive A/D input channels on the I/O Controller board where they are converted to 10 bit digital values. A software algorithm in the I/O Controller code uses these inputs to determine the flow condition. The design of the voltage divider guarantees that the output remains within the A/D input range of 0 to +5 V over the input temperature/flow range and over all component tolerances.

Conductivity Monitoring

The dialysate conductivity probe (FIG. 1B, item 60) comprises two stainless steel probes inserted into the flow path just prior to the dialyzer. The drive signal for the conductivity probes is a capacitive-coupled squarewave generated on the I/O Hydraulic board 534. This signal is sent to the conductivity probe and a monitor circuit. Both the monitor circuit and the return signal are rectified and filtered. These dc values are routed to I/O Controller board 514 along with the temperature signal.

On the I/O controller board, the temperature, conductivity, and conductivity reference signals are input to an A-to-D converter that is monitored by the on-board 8040 microcontroller. The microcontroller calculates the temperature-compensated conductivity. This value is then displayed on the CRT as the conductivity in milliSiemens per centimeter (mS/cm).

Temperature Monitoring

The thermistor (FIG. 1B, item 168) installed in the dialysate conductivity probe (FIG. 1B, item 60) changes its resistance in response to changes in temperature. The values for dialysate conductivity and temperature measured at this probe are displayed on the CRT and are used to generate the primary alarms for patient safety. If either value is outside preset alarm limits, a bypass condition and an audio alarm occur.

The thermistor is wired to a resistor divider network on the I/O hydraulic board. The output of this divider network is sent to the Miscellaneous I/O controller board 514 where it is monitored by the onboard 8040 microcontroller via an A-to-D converter network. From this information, the controller calculates, the temperature using offset and gain parameters stored in the host from the calibration. Calibration of the temperature measurement is a two-point procedure done at 30 and 40° C.

Line Clamp

The line clamp opens with a solenoid and clamps with a spring return. When the solenoid is not energized, the spring pushes the plunger away from the solenoid. This causes the plunger to clamp the blood tubing. When the solenoid is energized, it pulls the plunger in with enough force to overcome the spring force. This unclamps the blood tubing. In the event of a power failure, the solenoid is de-energized causing the blood line to be clamped.

The solenoid is controlled by the line clamp board. On the line clamp board is a pulse-width modulated current controller. This circuit applies sufficient current to the line clamp solenoid to pull in the plunger. After pull in, the controller ramps the current down to a level capable of holding the line clamp open. This cutback in current reduces the temperature of the solenoid, resulting in a more reliable device. Also located on the line clamp board, is a quick-release circuit which helps dissipate the power stored in the solenoid. The result of this circuitry is a quicker and more repeatable clamp time over the life of the machine.

Control for the line clamp comes from the Miscellaneous I/O controller board 514 via the I/O power board 536. The control signal for clamp and unclamp is optically coupled on the line clamp board. This provides electrical isolation between the high voltage used to operate the line clamp and the low voltage used for the control signals from the microprocessor.

Power Fail Alarm

The power-fail alarm circuitry is located on the Misc I/O Electrical Power board 536, and includes a CMOS power state flip flop powered by a 1 Farad (F) capacitor. The flip flop, which can be toggled by either the front panel power button or the 80286 system controller, provides the following functions:

Whenever power is not supplied to the machine (i.e., when the +5 V supply is off) and the flip flop is in the on state, power is supplied from the 1 F capacitor to the audio alarm device. Whenever power is supplied to the machine, the flip flop's output state is ready by the 80286, which provides indication of the intended machine power state. Also, when the flip flop is in the on state, power is supplied to the front panel power switch LED.

The first function listed above results in the power fail alarm. The alarm occurs either if the machine loses power while it is running, or if the front panel power button is pressed "on" when there is no power supplied to the machine. The alarm can be silenced by toggling the flip flop off via pressing "off" the front panel power button.

Additional details of the preferred computer system 500 are provided, inter alia, in Appendix C.

Reference has been made to five appendices (A-E) which form part of the specification hereof and which further detail certain aspects of the preferred embodiment.

Bypass Valve Flow Sensor

The dialysis machine of the present invention includes a bypass valve flow sensor which is utilized to confirm that dialysate flow to the dialyzer is completely interrupted during bypass. The bypass valve flow sensor comprises a first thermistor 202 and a second thermistor 204, as shown schematically in FIG. 2. FIG. 2 also shows in simplified schematic form the flow equalizer 54, the bypass valve 166, and a dialyzer 208. The first and second thermistors 202, 204 are of a negative-temperature coefficient (NTC) type known in the art. The first, or "sensing," thermistor 202 is energized with a 20 mA constant current while the second, or "reference," thermistor 204 is driven with a negligibly small current.

The electrical resistance of both thermistors 202, 204 is measured using electronic circuitry (not shown). The resistance R(T) of each thermistor 202, 204 at a given temperature T is determined by the following relationship:

$$R(T)=(K_1)\exp(-K_2 T)$$

where $K_1$ and $K_2$ are constants. Hence, the thermistor resistance is a function of its temperature.

Since the electrical power input to the reference thermistor 204 is negligibly small, the temperature of the reference thermistor 204 will be substantially equal to that of the liquid surrounding it, whether flowing or not, at all times. The sensing thermistor 202, on the other hand, is powered by a substantial constant current. Hence, the sensing thermistor 202 will undergo appreciable self-heating. During conditions of no dialysate flow past the thermistors 202, 204, such as during bypass, the temperature of the reference thermistor 204 will be equal to the temperature of the dialysate surrounding the reference thermistor 204. However, the no-flow temperature of the sensing thermistor 202, as a result of self-heating, will be substantially greater than the temperature of the reference thermistor 204. During conditions when dialysate is flowing past the thermistors 202, 204, the temperature of the reference thermistor 204 will, again, be equal to the temperature of the dialysate. The temperature of the sensing thermistor 202, while greater than that of the reference thermistor 204, will be somewhat lower than the temperature thereof would otherwise be during no-flow conditions. This is because dialysate flowing past the sensing thermistor 202 will conduct a portion of the self-heating energy away from the thermistor 202, thereby lowering the temperature of the thermistor 202. The bypass flow sensor can detect flow as low as about 3 mL/min.

Since the sensing thermistor 202 is driven with a constant-current source, the amount of power input into the thermistor 202 is limited according to the relationship $P=I^2 R$. As a result, the ultimate self-heating temperature achievable by the sensing thermistor 202 will self-limit, thereby protecting the sensing thermistor 202 from a damaging thermal runaway condition.

The two thermistors 202, 204 are calibrated by measuring the electrical resistance across them individually under conditions of no dialysate flow at both 30 and 40° C. A mathematical relationship is utilized during calibration which equates the resistance of the sensing thermistor, 202 and the resistance of the reference thermistor 204 at any temperature between 30 and 40° C. If Rh(t) represents the sensing thermistor resistance at T=t, and Rr(t) represents the reference thermistor resistance at T=t, then, at no dialysate flow, Rh(t)=A Rr(t)+B, where A and B are calibration constants determined by the equations shown below (since Rh(30), Rh(40), Rr(30), and Rr(40) are measured during calibration):

$$Rh(30)=A \cdot Rr(30)+B$$

$$Rh(40)=A \cdot Rr(40)+B$$

Hence, if the thermisior resistances are equal, then the electronic circuitry (not shown) coupled to the thermistors 202, 204 recognizes such equal resistance as indicating a "no dialysate flow" condition. However, if 5 the resistances of the first and second thermistors 202, 204 are not equal, which occurs when any dialysate flow (greater than about 3 mL/min) is passing by the first and second thermistors 202, 204, the electronic circuitry recognizes a "dialysate flow" condition. Therefore, whenever the machine is in bypass, if the electronic circuitry senses that the resistances across the first and second thermistors 202, 204 is unequal, indicating flow, the machine will trigger an alarm condition to notify the operator of failure of the bypass valve 66.

The advantage of the bypass valve flow sensor 62 as described hereinabove is that it enables the dialysate bypass valve 66 to be tested functionally, i.e., via a determination of whether or not the bypass valve 66 actually shut off the flow of dialysate to the dialyzer 208. This is the first known use of such a flow sensor in a hemodialysis machine. Other bypass valve sensors known in the relevant art merely test whether or not, for example, the bypass valve has been energized. One example of such a mechanism is a sensor that determines whether or not a solenoid controlling the valve has shifted position in response to application of current thereto. In the present invention, in contrast, the bypass valve flow sensor verifies that the bypass valve 66 has actually seated properly.

Further details and engineering data pertaining to the bypass valve flow sensor can be found in Appendix A, pp. ET 52-ET 57 ("Flow Sensing"), ET 75 ("Bypass Fail Alarm"), Hydraulic Theory 9 ("Flow Sensor" and "Bypass Valve"), EC 13 ("Bypass Fail Detection"), and EA 11 ("Bypass System and Flow Sensor").

No-Ultrafiltration-During-Bypass Sensor

This feature, shown schematically as item 70 in FIGS. 1A and 2, utilizes a first and a second thermistor 210, 212 in a manner similar to the bypass valve flow sensor 62 discussed above. The first and second thermistors 210, 212 are exposed to dialysate flowing through conduit 174 just downstream of the dialyzer 208 but upstream of the bypass line 166.

This feature 70 is utilized during automatic testing of machine functions, as controlled by the machine's microprocessor. During such a test, dialysate flow is bypassed from the dialyzer 208. The flow equalizer 54 volumetrically matches the volume of dialysate that would ordinarily enter the dialysate compartment (not shown) of the dialyzer 208 with the volume of dialysate exiting the dialyzer 208. During bypass, the volume of dialysate passing through the bypass valve 66 and bypass line 166 is equal to the volume passing back through the flow equalizer 54 via line 158. Since the UF line 178 is occluded by the UF flow meter 76, any dialysate flow past the first and second thermistors 210, 212 in either direction must be due to dialysate flow passing through the dialyzer membrane (not shown) into the blood compartment (not shown) thereof or from the blood compartment thereof into the dialysate compartment thereof. If such flow is detected, the machine triggers an operator alarm.

Further details and engineering data pertaining to the no-UF-during-bypass sensor can be found in Appendix A, pp. ET 52-ET 57 ("Flow Sensing"), and Hydraulic Theory 10 ("Flow Sensor").

Automatic Testing of Ultrafiltration Function

This feature is utilized during automatic testing of machine functions that occurs before the machine is used for patient treatment. This automatic test is controlled by the machine's microprocessor along with other self-test routines. One example of when ultrafiltration-function testing is automatically engaged is when the machine is in rinse and producing dialysate without any prevailing dialysate alarms such as temperature and conductivity. A complete self-test routine begins when the operator touches the "test" button on the touch screen before beginning a dialysis treatment. (See Appendix A, pp. Operation 3 (Step 10).)

In order to test the ultrafiltration function, the dialysate lines 174, 206 (FIGS. 1A and 2) must be connected together, enabling dialysate to circulate therethrough without having to use a dialyzer. Because a dialyzer is not used, the flow equalizer 54 discharges a volume of dialysate into line 206 that is substantially equal to the volume of dialysate passing through line 174. Hence, a volumetrically closed loop is formed wherein dialysate exits the flow equalizer 54 through the outlets 156 thereof, passes through lines 206 and 174 coupled together, and reenters the flow equalizer 54 through the inlets 154 thereof. Included in this closed loop is the UF flow meter 76. The UF flow meter 76 permits a discrete volume of fluid to be removed from the closed loop. Also included in the closed loop is the dialysate pressure transducer 64.

To perform the test, the UF flow meter 76 removes about 3 mL of dialysate from the closed loop. This removal of 3 mL is sufficient to lower the dialysate pressure measured at the transducer 64 by about 200 to 300 mmHg. If there are no leaks in the closed loop, this lowered pressure will remain substantially constant. The machine will monitor the depressed dialysate pressure for about 30 seconds during which the pressure must remain within a ±50 mmHg limit of the initial low value. If the pressure rises and passes a limit, the machine will trigger an operator alarm.

Further/pertinent details concerning this feature and the UF flow meter can be found in Appendix A, pp. EA 7 ("UF Removal Control"), EC 25-EC 26 ("UF Protective System"), EC 29-EC 30 ("UF Test"), M 6 ("Flow Equalizer"), M 9 ("UF Removal Flowmeter"), M 17-M 19 ("Dialysate Flow Control System Performance"), and Hydraulic Theory 7 ("Flow Equalizer").

Automatic Setting of Proportioning Mode Based Upon Connection of Concentrate Lines As described hereinabove, the concentrate rinse fittings, e.g., the "A" and "B" rinse fittings 28, 30, respectively (FIG. 1A), are equipped with proximity sensors which sense whether or not the corresponding concentrate lines 94, 104, respectively, are connected thereto. Such information regarding whether or not a concentrate line is coupled to a corresponding rinse fitting is utilized by the machine's microprocessor to set the correct proportioning mode, e.g., acetate or bicarbonate dialysis.

For example, during the machine's "dialyze" mode, if the machine's microprocessor receives a signal indicating that the "B" concentrate line 104 is coupled to the "B" rinse fitting 30, the machine will operate only the "A" concentrate pump 22. If the "B" concentrate line 104 is not coupled to the "B" rinse fitting 30, the machine will operate both the "A" and "B" concentrate pumps 22, 40, respectively. See Appendix A, pp. EA 5-EA 6 ("Proportioning Control"), and EA 7-EA 8 ("Conductivity Monitoring").

Such connections of the "A" and "B" concentrate lines 94, 104 also dictate the proportioning ratio of "A" concentrate. During acetate dialysis, the volumetric ratio of "A" concentrate to dialysate is 1:35. During bicarbonate dialysis with Drake Willock brand concentrates, for example, the volumetric ratio of "A" concentrate to dialysate is 1:36.83. Hence, the machine automatically adjusts the pumping rate of the "A" concentrate pump 22 in response to whether or not the "B" concentrate line 104 is coupled to the "B" rinse fitting 30.

Figure 3A:
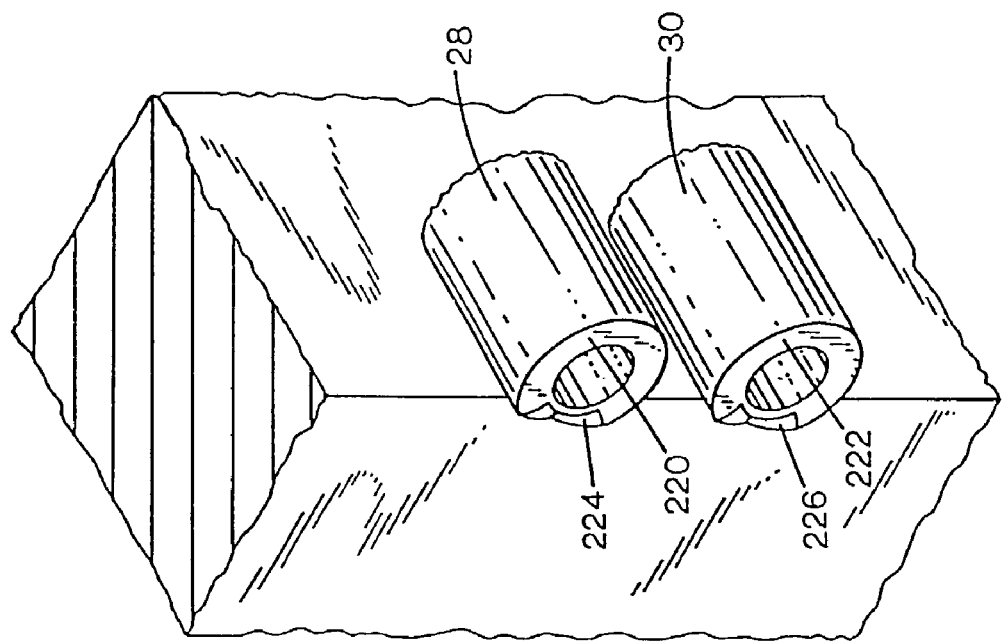
FIGS. 3A and 3B are isometric and schematic diagrams, respectively, of a concentrate-line proximity sensor comprising a portion of the automatic proportioning mode setting feature of the present invention.
Figure 3B:
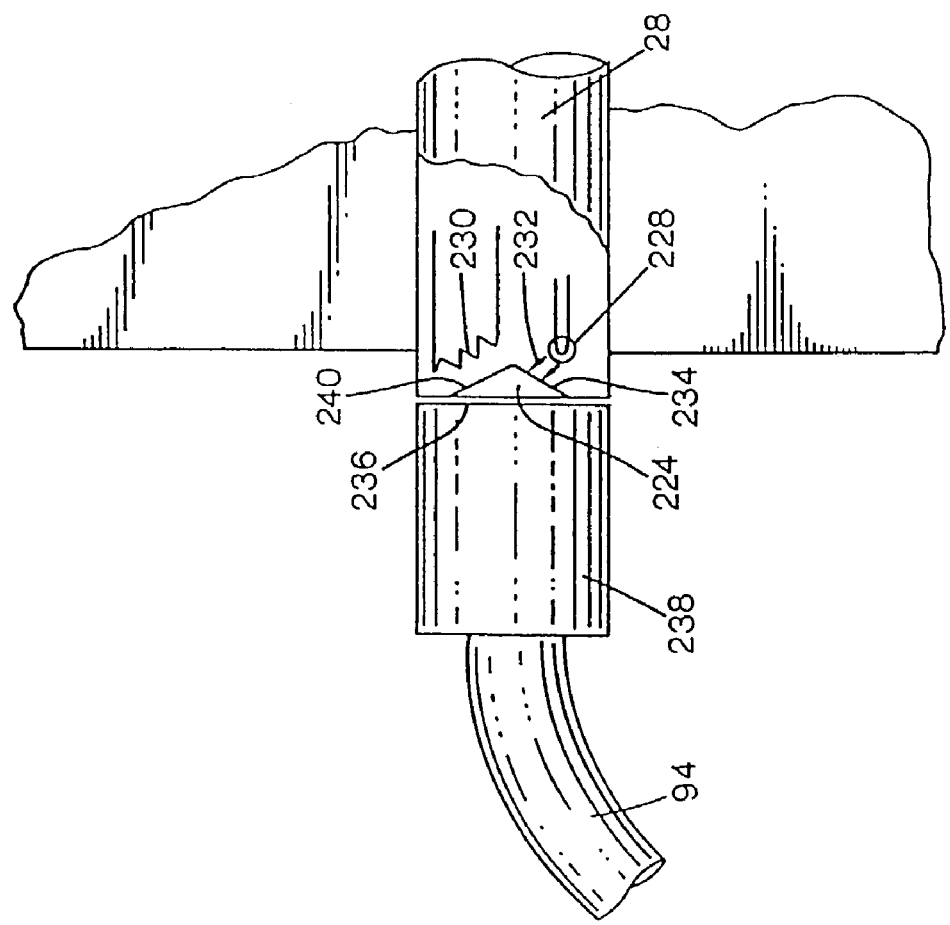

The proximity sensors are shown in FIGS. 3A and 3B. FIG. 3A is an isometric depiction of, for example, the "A" and "B" rinse fittings 28, 30 situated on the right side 218 of the machine. (See Appendix A, pp. Components & Functions 11). On the annular surface 220, 222 of each rinse fitting is an angled depression 224, 226, respectively. As depicted in the right-side elevational view of the "A" rinse fitting 28 shown in FIG. 3B, beneath the angled depression 224 is a light-emitting diode (LED) 228 (shown schematically). A photosensor 230 of a type known in the art is also situated beneath the angled depression 224. The LED 228 is energized with a pulsatile signal in the kilohertz range (so as to not be fooled by 60 Hz illumination). The LED 228 and photosensor 230 are oriented such that light 232 from the LED 228 passes through a first face 234 of the angled depression 224, is reflected off an annular surface 236 of a connector 238 on the end of the "A" concentrate line 94, passes through a second face 240 of the angled depression 224 to be sensed by the photosensor 230.

So long as the photosensor 230 receives reflected light from the LED 228, the machine's microprocessor circuitry (not shown) "interprets" such a condition as indicating that the "A" concentrate line 94 is coupled to the "A" rinse fitting 28. If the light 232 does not reflect so as to impinge the LED 230, the microprocessor circuitry "interprets" such a condition as indicating that the "A" concentrate line 94 is not coupled to the "A" rinse fitting 28 but is coupled to, e.g., a supply of "A" concentrate.

Prediction of Dialysate Conductivity

The software controlling the operation of the machine's microprocessor includes a routine for predicting correct dialysate conductivity. Such predictions automatically reflect the particular brand of concentrate being used, since different groups of concentrate brands require different proportioning to yield a dialysate having a correct ionic strength and electrolytic profile.

Various groups of concentrates are currently marketed. These include: (1) bicarbonate concentrates manufactured by Cobe (utilizable for variable sodium and variable bicarbonate dialysis and intended to be diluted at a ratio of 1 part "A" concentrate to 1.43 parts "B" concentrate to 45 parts dialysate); (2) bicarbonate concentrates manufactured by Drake Willock (utilizable for variable sodium dialysis only and intended to be diluted at a ratio of 1 part "A" concentrate to 1.83 parts "B" concentrate to 36.83 parts dialysate); and (3) acetate concentrates intended to be diluted at a ratio of 1 part acetate concentrate to 35 parts dialysate. The machine is "instructed" or programmed by a technician as to which brand of concentrate is being used. Such programming is done using the touch screen with the machine in the "calibration" mode. See, e.g., Appendix A, pp. Preventive Maintenance 8, Calibration Screen #1, item 17.

The software utilizes a different algorithm for each group of concentrates and for acetate or bicarbonate dialysis using concentrates within any single group, to calculate a baseline "calculated" conductivity value. Each algorithm requires that certain data be entered by the operator using the touch screen. For example, for bicarbonate dialysis, the machine will "ask" the operator to enter baseline (i.e., not adjusted up or down relative to a standard, or non-variable, proportioning ratio) values for sodium and bicarbonate ion concentrations. Assuming proper proportioning of the concentrates, the machine will determine a "calculated" dialysate conductivity. Before beginning a dialysis treatment, when the machine is proportioning concentrate and producing dialysate at the proper temperature, the touch screen will display an "actual" dialysate conductivity value as measured by the dialysate conductivity probe 60 (FIG. 1B) and "ask" the operator to verify the correctness of that value against the value stated to be correct by the concentrate manufacturer on the concentrate label. See Appendix A, pp. operation 3. If the operator responds that the displayed conductivity value is correct, the machine will compare the displayed "actual" value with the "calculated" value. If the "calculated" value is different from the displayed value, the machine will regard the displayed baseline value as correct since the operator "told" the machine that the displayed value is correct. The machine will also calculate the ratio of the displayed baseline value over the calculated baseline value and will multiply any subsequently determined calculated value during the dialysis treatment by the ratio to obtain new "expected" conductivity values. For example, for variable sodium dialysis, the operator will program the variable sodium profile to be delivered to a patient over the course of the upcoming dialysis treatment. Whenever the machine changes the sodium concentration during the course of treatment as programmed by the operator, which accordingly changes the dialysate conductivity, the machine will redetermine a "calculated" conductivity value and apply said ratio to determine a new "expected" conductivity value. These expected conductivity values are used by the machine to calculate and set upper and lower conductivity alarm limits at ±5% of the initial or adjusted "expected" conductivity value.

For Cobe brand bicarbonate concentrates, the calculated baseline dialysate conductivity is determined by the following algorithm:

$$\text{calculated conductivity in mS/cm} = [-0.036 + 3.7x^{10-5}([Na^+]-130)][HCO_3] + [14.37 + 0.101([Na^+]-130)]$$

where the operator enters the baseline concentrations of sodium and bicarbonate using the touch screen.

For Drake Willock brand bicarbonate concentrates, the calculated baseline conductivity of bicarbonate dialysate is determined by the following algorithm:

$$\text{calculated conductivity in mS/cm} = 0.1038[Na^+] - 0.54$$

where the operator enters the baseline concentration of sodium using the touch screen.

For all brands of acetate concentrates, the calculated baseline conductivity of acetate dialysate is determined by the following algorithm:

$$\text{calculated conductivity in mS/cm} = 0.0895[Na^+] + 1.41$$

where the operator enters the baseline concentration of sodium using the touch screen.

For bicarbonate dialysis, the machine will also automatically set alarm limits around the conductivity measured at the "A" conductivity probe 38 (FIG. 1A) in a similar manner. (During acetate dialysis, the conductivity at the "A" conductivity probe 38 is equal to the conductivity at the dialysate conductivity probe 60, so setting of alarm limits around the conductivity at the "A" conductivity probe is not necessary.) For bicarbonate dialysis, the machine "assumes" that the "A" concentrate is being proportioned properly (at the correct proportioning ratio), based upon the operator having verified that the displayed dialysate conductivity value is correct. The machine determines a baseline "calculated" conductivity at the "A" conductivity probe based on baseline sodium and bicarbonate concentrate information provided by the operator via the touch screen. The machine then calculates a ratio of the actual conductivity as measured at the "A" conductivity probe 38 over the calculated conductivity at the "A" conductivity probe. Then, whenever the machine changes the sodium concentration during the course of a dialysis treatment as programmed by the operator, the machine will determine a new calculated conductivity value and apply said ratio to determine a new "expected" conductivity value at the "A" conductivity probe.

For Cobe brand bicarbonate concentrates, the calculated baseline conductivity at the "A" conductivity probe is determined by the following algorithm:

$$\text{calculated conductivity in mS/cm} = [-0.110 + 9.7 \times 10^{-5}([Na^+]-130)][HCO_3] + [15.04 + 0.105([Na^+]-130)]$$

where the operator enters the baseline sodium and bicarbonate concentrations using the touch screen.

For Drake Willock brand bicarbonate concentrates, the calculated baseline conductivity at the "A" conductivity probe is determined by the following algorithm:

$$\text{calculated conductivity in mS/cm} = 0.1114[Na^+] - 5.90$$

where the operator enters the baseline sodium concentration using the touch screen.

Further information on this feature is in Appendix A, pp. ET 23-ET 28 ("UF/Proportioning System"), and EC 34 ("Conductivity Verify Test").

Controlling Flow Equalizer End-of-Stroke Time

As discussed hereinabove, the flow equalizer 54 (FIG. 1B) operates via a four-phase cycle. In the first and third phases, "pre" compartments 130, 132 and "post" compartments 134, 136 alternately fill and discharge their contents. In the second and fourth phases, the valves 142-149 controlling liquid ingress and egress from the "pre" and "post" chambers are all in the off position for about 125 msec. During these brief second and fourth phases, therefore, no dialysate is flowing to the dialyzer.

Preferably, at the beginning of the second and fourth phases, the diaphragms 138, 140 will have already reached end of stroke. Further preferably, the diaphragms 138, 140 will have reached end of stroke at the same instant.

End of stroke is the moment when, for example, the "post" compartment 134 has reached a completely full condition during a phase after starting from a completely empty condition at the start of the phase. In accordance with the above, it is preferable, for example, that the filling of the "post" compartment 134 reach end of stroke at the same instant as filling of the "pre" compartment 132 during a phase and that filling of the "post" compartment 136 reach end of stroke at the same instant as filling of the "pre" compartment 130 during a different phase. Such simultaneous reaching of end of stroke eliminates ultrafiltration inaccuracies that otherwise could result if the "pre" and "post" compartments (e.g., 130 and 136) being, say, filled during a phase are not filled at exactly the same rate.

Since valves 143, 144, 146, and 149 all turn on at the same instant that valves 142, 145, 147, and 148 turn off, and vice versa, and since each pair of compartments 130, 134 and 132, 136 have exactly the same volume, it is possible to have pairs of compartments (130, 136, and 134, 132) reach end of stroke at the same instant. However, assuming that each chamber 126, 128 has exactly the same flow restriction therethrough, achieving simultaneous end of stroke requires at least that pressures at the inlets 154 be matched and that pressures at the outlets 156 be matched.

Figure 4:
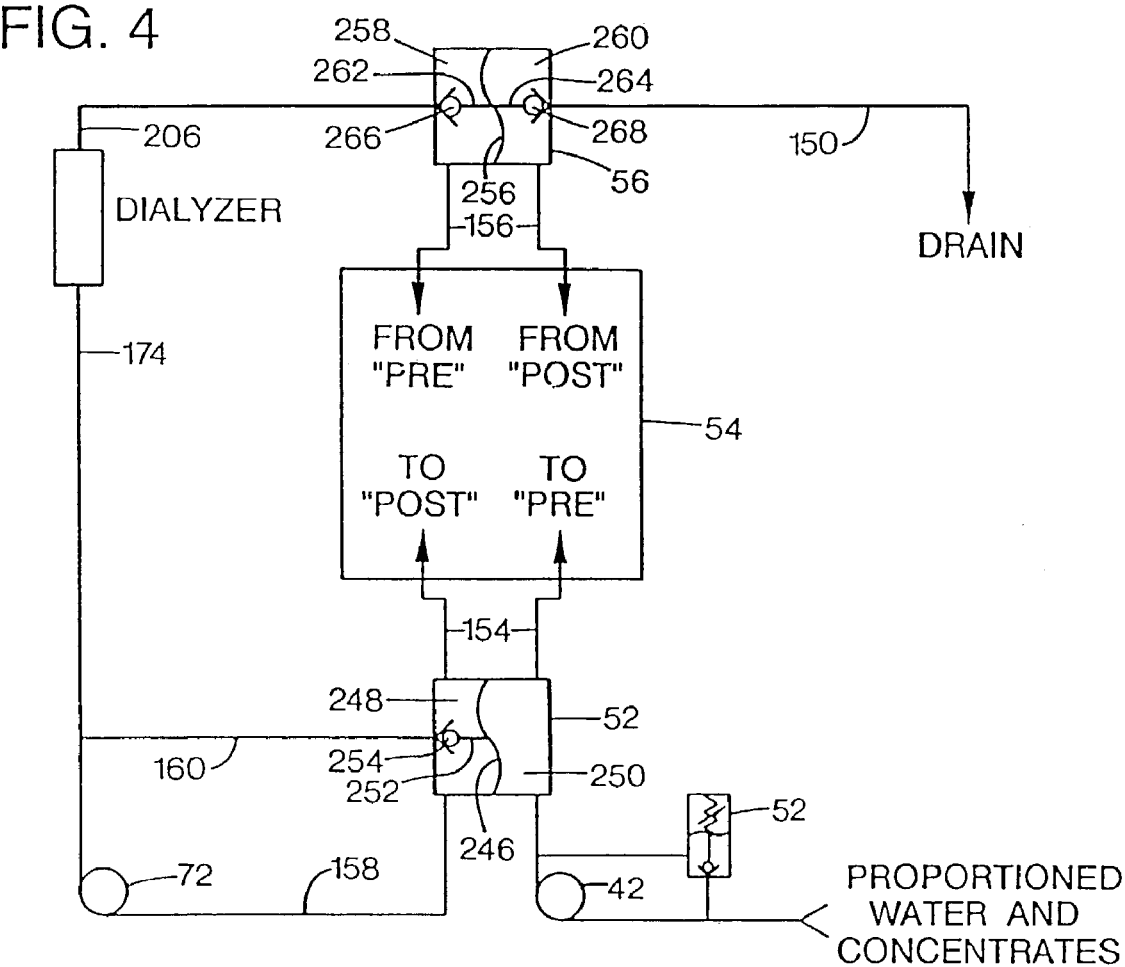
FIG. 4 is a schematic diagram showing the interconnection of input and output pressure equalizers into the hydraulic flow path of the present invention.

To achieve such pressure matching, the inlets 154 are provided with an input pressure equalizer 52 and the outlets 156 are provided with an output pressure equalizer 56, as shown in FIG. 4. The input pressure equalizer 52 is comprised of a flexible diaphragm 246 separating first and second enclosed cavities 248, 250. A stem 252 is attached to the center of the diaphragm 246 and terminates with a flow-restricting element 254. The output pressure equalizer 56 is likewise comprised of a flexible diaphragm 256 separating first and-second enclosed cavities 258, 260. Extending from the center of the diaphragm 256 on both sides thereof are stems 262, 264, each terminating with a flow-restricting element 266, 268.

Dialysate from the supply pump 42 flows unimpeded through the second cavity 250 on into a "pre" compartment of the flow equalizer 54. The first cavity 248 passes dialysate from the dialyzer to a "post" compartment of the flow equalizer 54. The first cavity 248 is also part of a loop including the dialysate pressure pump 72. This hydraulic configuration has been found to maintain identical pressures and therefore identical flow rates at the inlets 154 of the flow equalizer 54.

With respect to the output pressure equalizer 56, when the pressure is equal in both cavities 258, 260, the flow rates through each is identical. When the pressure, say, in the first cavity 258 exceeds that in the second cavity 260, the flow-restricting element 268 impedes flow into line 150, thereby increasing the pressure in the second cavity 260. This hydraulic configuration has been found to maintain identical pressures and therefore identical flow rates at the outlets 156 of the flow equalizer 54.

Therefore, since pressures and flow rates are identical as described above, both diaphragms 138, 140 (FIG. 1B) come to end of stroke at the same time.

The time required to attain end of stroke can also be controlled. The dialysate flow rate is set by the operator using the touch screen. This flow rate determines the shift frequency of the valves 142-149. The higher the dialysate flow rate, the more frequently the valves 142-149 shift. However, a machine malfunction or occlusion of a hydraulic line could cause an excessive end-of-stroke time for one or both diaphragms 138, 140.

As discussed hereinabove, flow sensors 58, 59 (FIG. 1B) are provided at the outlets 156 of the flow equalizer 54 for verifying when the diaphragms 138, 140 have reached end of stroke. When a diaphragm 138 or 140 has reached end of stroke, the corresponding flow sensor 58 or 59, respectively, sends a no-flow signal to the microprocessor. The flow sensors 58, 59 are each comprised of a reference and sensing thermistor (not shown) and work in a manner similar to the bypass valve flow sensor 62 and sensor 70 discussed hereinabove.

If the valves 142-149 receive a signal from the microprocessor to shift before the flow sensors 58, 59 have detected end of stroke, the valves are prevented by the microprocessor from shifting until the end-of-stroke signal(s) are received by the microprocessor. In the event of an excessively long end-of-stroke time, the microprocessor triggers an increase in the pumping rate of the supply pump 42 to speed up the time to end of stroke.

Controlling the end-of-stroke time not only increases the UF removal accuracy of the machine but also keeps dialysate flowing through the dialyzer as much as possible to maintain the desired osmotic gradient therein, and ensures accurate proportioning and mixing of concentrates with water to form dialysate.

Further details on this feature can be found in Appendix A, pp. EA 6 ("Flow Control"), ET 28-ET 32 ("Dialysate Flow Control"), M 17-M 19 ("Dialysate Flow Control System Performance"), and Hydraulic Theory 6-8 ("Input Pressure Equalizer," "Flow Equalizer," "Output Pressure Equalizer," "End of Stroke Sensors").

Timed Mode Initiate From Power-Off

The microprocessor programming as described herein can be conventionally implemented to accomplish a timed mode initiation from a power-off condition. As is known in the art, machine disinfection, rinsing, and "coming up" on concentrate and temperature to produce dialysate in a condition to begin treatment are burdensome tasks that typically must be performed before the start of a treatment day. In large clinics having multiple dialysis machines, performing these tasks manually can require a substantial expenditure of time and other personnel resources.

The electronics of the machine are continuously powered, even when the machine is "off," unless the mains switch has been turned off or unless the machine's power cord is unplugged. As a result, the programming is readily adapted to include use of the key pad display on the touch screen by the operator to enter the desired time at which certain designated machine functions are automatically initiated. These functions include disinfection (such as heat-cleaning), rinsing, and beginning the production of dialysate at the desired temperature and ionic strength for dialysis treatment.

Preservation of Machine Parameters During Brief Power-Off

The hemodialysis machine of the present invention is provided with a battery back-up which preserves certain operational parameters previously entered by the operator in the event of a temporary power interruption (less than about 20 minutes). Upon restoration of power, the machine is in the stand-by mode.

All of the following parameters are saved in static RAM every 30 seconds or upon any major change in machine state. Upon restoration of power after less than 20 minutes after the last "time stamp" (time at which parameters were saved) by the machine, the following parameters are restored:

Temperature correction
Accumulated UF volume removed
Desired UF removal volume
UF removal rate
UF override flag
Current machine state
Previous machine state
Self-test pass/fail flag
Time stamp
Prescribed dialysis time
Elapsed treatment time
Prescribed or elapsed treatment time display flag
Manual or calculated UF rate display flag
Heparin pump rate
Accumulated blood
Accumulated heparin
Alarm window limits for conductivity, temperature, prescribed treatment time, heparin, etc.
Profile settings for variable sodium and bicarbonate Upon restoration of power, the "dialyze" mode can be restored by the operator touching the appropriate "button" on the touch screen.

Drip-Chamber Level Adjusters

As is known in the art, hemodialysis treatment requires use of an extracorporeal blood-line set. Blood-line sets are available from a number of manufacturers in a variety of different configurations. Virtually all blood-line sets have at least a venous drip chamber. Usually, an arterial drip chamber is also included. The drip chambers serve several functions, including providing a means for removing air and foam from the extracorporeal blood before the blood is returned to the patient, and providing convenient sites at which extracorporeal arterial and venous blood pressure can be measured.

A portion of the extracorporeal blood-line set, including drip chambers, is normally fitted to the front of a hemodialysis machine in an orderly and convenient arrangement using special clips and the like. See Appendix A, pp. Components & Functions 4-5. Each drip chamber typically includes a short tubing segment terminated with a female fitting of a type known in the art as a Luer fitting. The female Luer is adapted for connection to a male Luer fitting on or near the front of the machine (see Appendix A, pp. Components & Functions 2-3), thereby providing the requisite connection of the drip chamber to a pressure-measuring component in the machine.

Drip chambers must be provided with a means for adjusting the blood level therein, particularly to ensure that the blood level does not drop so low in the drip chamber that air becomes re-entrained in the blood. Dialysis machines as currently known in the art require that the operator manually rotate one or more knobs on the machine to rotate a peristaltic pump coupled to the corresponding drip chamber. Such a manual operation has proven to be a cumbersome annoying task, especially since the peristaltic pumps can be difficult to rotate.

Figure 5:
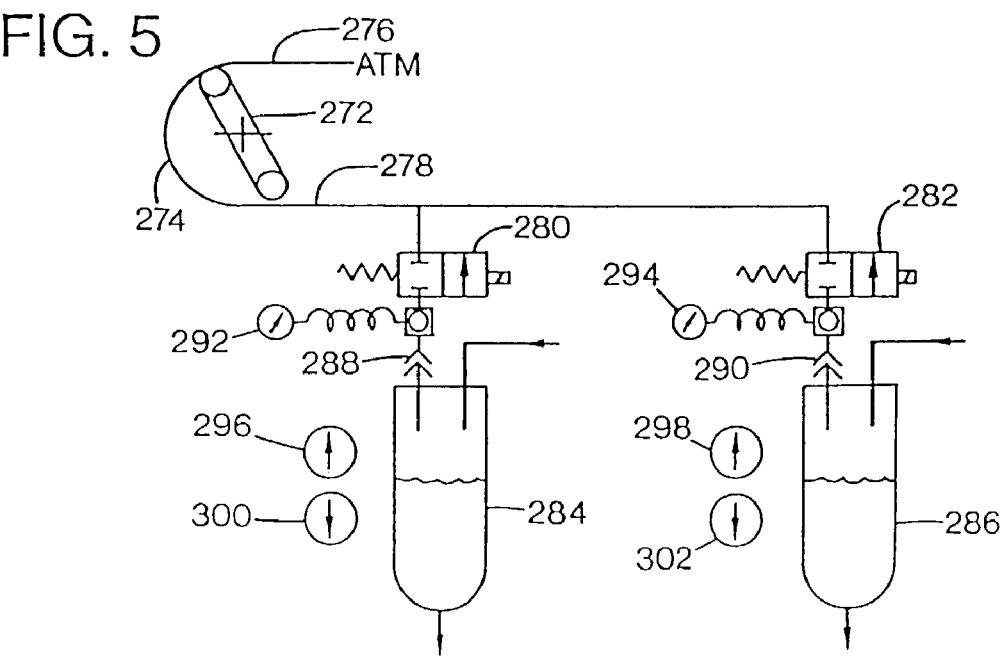
FIG. 5 is a schematic diagram of the automated drip-chamber level adjusters of the present invention.

The machine of the present invention overcomes this problem by providing, as shown schematically in FIG. 5, an electrically driven reversible positive-displacement pump such as a peristaltic pump 272 which replaces the hand-operated peristaltic pumps found on conventional hemodialysis machines. The peristaltic pump 272 is fitted with flexible tubing 274, one end 276 of which is open to the atmosphere. The opposite end 278 is coupled in parallel to an "arterial" valve 280 and a "venous" valve 282 coupled to an arterial drip chamber 284 and a venous drip chamber 286, respectively. The valves 280, 282 are preferably solenoid valves of a type known in the art. Each drip chamber 284, 286 is coupled via a corresponding Luer fitting 288, 290 to the corresponding valve 280, 282. Included upstream of each Luer fitting 288, 290 is a pressure-measuring device 292, 294, such as a pressure transducer, which communicates with the microprocessor (not shown).

On the front of the machine are arterial and venous "up" buttons 296, 298, respectively, and arterial and venous "down" buttons 300, 302, respectively, which control operation of the corresponding valves 280, 282 and the peristaltic pump 272. See Appendix A, pp. Components & Functions 2-3. For example, pressing the arterial "up" button 296 opens valve 280 and initiates rotation of the peristaltic pump 272 so as to raise the blood level in the arterial drip chamber 284. Pressing the arterial "down" button 300 opens valve 280 and initiates an opposite rotation of the peristaltic pump 272 so as to lower the blood level in the arterial drip chamber 284. The venous "up" and "down" buttons 298, 302 operate in the same way to control the blood level in the venous drip chamber 286.

Further details pertaining to this feature are in Appendix A, pp. EA 4 ("Level Adjust"), ET 11-ET 12 ("Level Adjust"), and M 2-M 3 ("Level Adjusters").

Increasing Dialysate Flow Velocity Through the Dialyzer Without Increasing Dialysate Flow Rate Most hemodialyzers currently in use are hollow-fiber types which generally have a more compact shape than parallel-plate or coil dialyzers used previously. Hollow-fiber dialyzers as known in the art typically comprise a bundle of fine hollow fibers, each fiber made of a semipermeable membrane material, encased in an outer cylindrical shell. The shell defines a space surrounding the fibers termed the "dialysate compartment" through which flows the dialysate prepared by a dialysis machine. The patient's blood is conducted through the lumens of the hollow fibers, propelled by a blood pump on the dialysis machine.

Clearance of metabolic solutes from the blood through the fiber membrane to the dialysate depends on a number of factors, including the osmotic gradient across the semipermeable membranes. The osmotic gradient is dependent on a number of factors including ionic strength and ionic profile of the dialysate, dialysate flow rate through the dialysate compartment, and flow dynamics of the dialysate as it flows through the dialysate compartment.

It is important that the dialysate flow rate be high enough to expose the fibers to a sufficient supply of fresh dialysate to effect satisfactory clearance of toxic solutes from the patient's blood at a satisfactory rate. Any dead spaces or areas of blockage in the dialysate compartment which are not exposed to a continuous supply of fresh dialysate will adversely affect clearance. Such dead spaces can be reduced by merely increasing the dialysate flow rate. However, increasing the dialysate flow rate also increases the rate at which expensive dialysate concentrates are consumed. Therefore, it is advantageous, especially with large dialyzers, to increase dialysate flow velocity through the dialysate compartment without necessitating a corresponding increase in net dialysate flow through the dialysate compartment.

Figure 6:
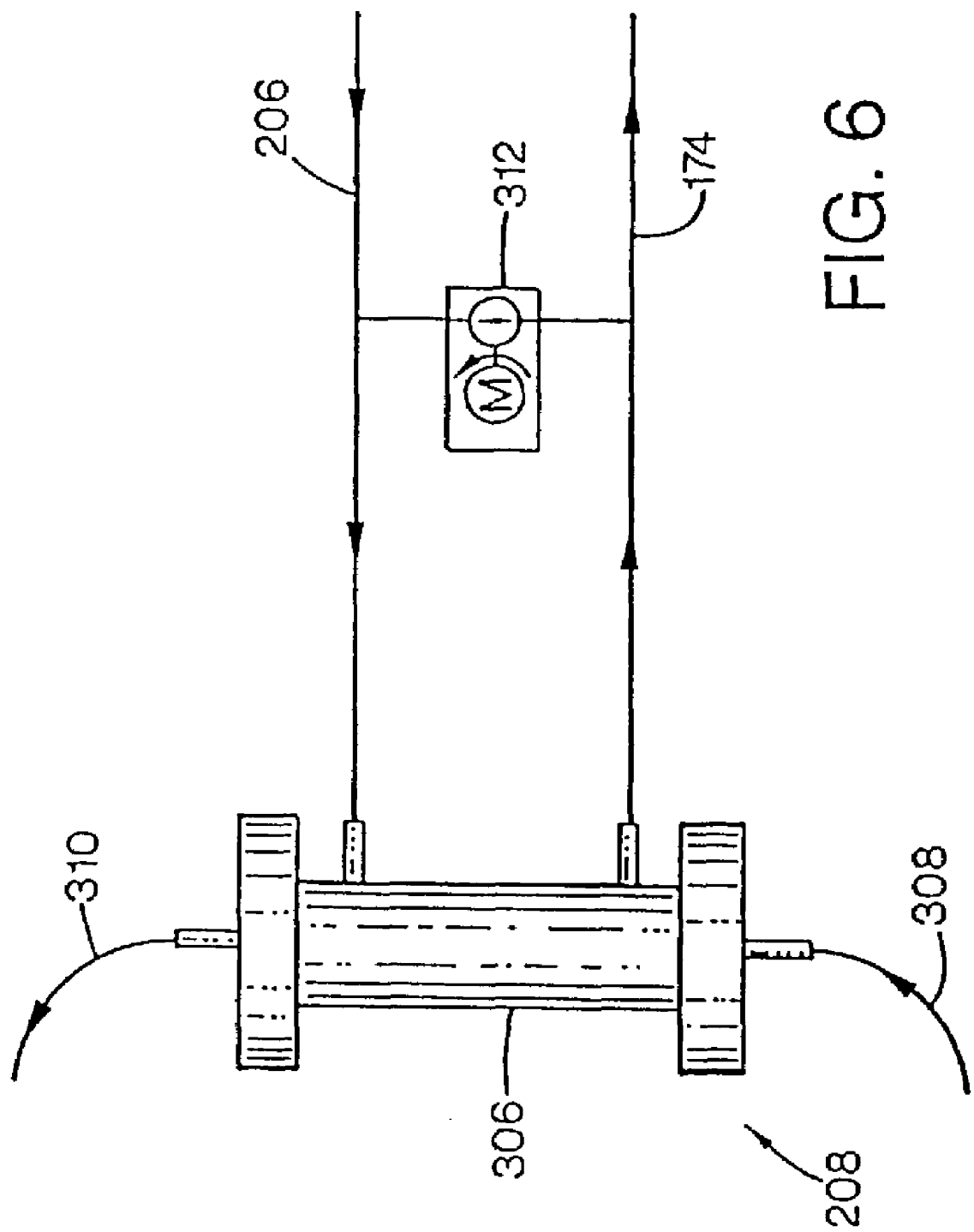
FIG. 6 is a schematic diagram a preferred embodiment of a means for increasing dialysate flow velocity through the dialyzer without increasing the dialysate flow rate.

An embodiment of the dialysis machine of the present invention solves this problem by incorporating a dialysate recirculation pump parallel with the dialyzer as shown schematically in FIG. 6.

FIG. 6 depicts a typical hollow-fiber dialyzer 208 having an outer shell 306 defining a dialysate compartment. Extracorporeal blood is pumped by the machine's blood pump (not shown) through an arterial blood line 308 from the patient (not shown), through the hollow fibers (not shown) of the dialyzer 208, then returned through a venous blood line 310 to the patient. FIG. 6 also shows the "arterial" dialysate line 206 and "venous" dialysate line 174 (see also FIG. 1A). A dialysate recirculation pump 312, such as an electrically driven gear pump, is coupled to the dialysate lines 206, 174 parallel with the dialyzer 208. The pump 312 can be driven with a variable-speed controller to adjust the pumping rate of the pump 312 relative to the flow rate of the dialysate as delivered by the dialysis machine (not shown).

By recirculating a portion of the "spent" dialysate from the "venous" dialysate line 174 to the "arterial" dialysate line 206 for repassage through the dialysate compartment 306, the flow velocity of the dialysate through the dialysate compartment can be increased without making a corresponding increase in dialysate flow. Hence, it is possible with this feature to improve clearances with a particular dialyzer without increasing the consumption of expensive dialysate concentrates.

Blood-Leak Detector

Virtually all dialysis machines in current use employ a blood-leak detector to monitor dialysate flowing from the dialyzer for the presence of blood that might have leaked from the blood compartment into the dialysate compartment of the dialyzer.

Most dialysis machines currently in use are capable of delivering only a fixed rate of dialysate flow, usually 500 mL/min. The blood-leak detectors on those machines operate with a detection sensitivity that is set at a fixed level and not changed during the course of treating a patient or even a series of patients. At a dialysate flow rate of 500 mL/min, many conventional blood-leak detectors are set to detect blood having a 25% hematocrit flowing at 0.35 mL/min into the dialysate.

The dialysis machine of the present invention is capable of delivering dialysate at flow rates ranging from 500 to 1000 mL/min, adjustable in 100 mL/min increments. At various dialysate flow rates, a fixed leak rate of blood from the patient will be diluted a different amount by the dialysate. Therefore, a blood-leak detector having a fixed sensitivity level enabling it to detect a small blood leak in dialysate flowing at 500 mL/min may not be able to detect the same blood leak in dialysate flowing at 1000 mL/min.

The dialysis machine of the present invention is provided with a blood-leak detector 78 employing a green LED 194 and a photosensor 196 (FIG. 1B). (A green LED is used because of the strong absorbance of green light by red blood, yielding a greater contrast in the blood-leak detector between the presence and absence of blood.) The blood-leak detector has a sensitivity that is automatically adjusted in a proportional manner to sense a given leak rate of blood into dialysate having any dialysate flow rate between the 500 to 1000 mL/min adjustability range. Such automatic adjustment of the blood-leak detector sensitivity is performed by the microprocessor in response to the operator selecting a desired dialysate flow rate. The microprocessor adjusts the blood-leak detector sensitivity by altering the illumination level of the LED 194.

Further details on this feature can be found in Appendix A, pp. EA 10 ("Blood Leak Detector"), EC 20 ("Blood Leak Detector"), EC 29 ("Blood Leak Detector Test"), and ET 46-ET 52 ("Blood Leak Detector").

Calibration Scheduler and Data Logger And Warning Message Logger

The dialysis machine of the present invention has a technician-activatable "calibration" mode and is programmed to permit entry of calibration data, dates on which certain calibrations or adjustments are performed, and dates on which a particular dialysis center may desire to have certain calibrations or adjustments performed. Appendix A, pp. Preventive Maintenance 8-9. The machine also automatically logs warning messages that can be of substantial help to a technician servicing the machine.

The calibration mode can be activated by turning on an internal calibration switch, as described in Appendix A, pp. Preventive Maintenance 7-8. When the calibrations are completed, the machine is returned to the operational mode by turning off the internal calibration switch, as described in Appendix A, pp. Preventive Maintenance 8, and restarting the machine using the mains power switch. Upon entering the calibration mode, the touch screen displays tables of various calibrations and makes provision for the operator to enter data or dates pertaining to any of the listed calibrations. These tables are illustrated in Appendix A, pp. Preventive Maintenance 8-9. Representative calibration instructions, including how to enter data, are provided in Appendix A, pp. Preventive Maintenance 9-20.

The machine includes a number of component monitors which are used by the microprocessor to note and "record" incidents wherein the respective components experience an operational anomaly of interest to a machine technician. For example, the "A" and "B" proportioning pumps 22, 40 (FIGS. 1A and 1B, respectively) are each driven with a stepper motor 90, 114, respectively. The stepper motors 90, 114 utilize 200 "steps" per revolution of the motor shaft. Appendix A, pp. EA 5-EA 6 ("Proportioning Control"). The stepper motors 90, 114 are provided with optical encoders by which the machine's microprocessor not only accurately monitors and controls the rate of concentrate delivery, but also monitors stepper motor operation. If the stepper motor experiences one full rotation per 190 "steps," the microprocessor will "note" and log this anomaly, even if no adverse effect on dialysate conductivity resulted therefrom. A list of warning messages is provided below. In the list, system names above groups of messages are for reference only. Messages having parentheses indicate software functions. While actual failure of such functions would not be expected to occur during machine operation, the messages were useful while debugging the software. Messages having particular value to the technician, especially for troubleshooting mechanical malfunctions, are denoted with an asterisk.

| BLOOD PUMP SYSTEM | |
| --- | --- |
| "illegal qlen in BP_XMIT" | |
| "Blood Pump Low Speed" | * |
| "BP Control Shutdown" | * |
| "BP Command Error" | * |
| "Blood Pump Overspeed Alarm" | * |
| "Bld Pmp Overspeed Alarm" | * |
| "Illegal index in bP xmit( )" | |
| "Illegal index in bP input( )" | |
| "long timer error" | |
| UF/PROP SYSTEM | |
| "Too much time between EOS signals" | * |
| "Early EOS detection" | * |
| "UP SHUTDOWN" | * |
| "UF Command Error" | * |
| "UF Time scheduled Event Error" | * |
| "Unidentified Error in MISC_ERRFLG" | |
| "A Pump Noise" | * |
| "A Pump Missed Steps" | * |
| "B Pump Noise" | * |
| "B Pump Missed Steps" | |
| "C Pump Noise" | * (for three pump system) |
| "C Pump Missed Steps" | * |
| "A temperature probe error" | * |
| "B temperature probe error" | * |
| IO SYSTEM | |
| "illegal qlen in IO_XMIT" | |
| "IO_XMIT: bad stat chnge %d, %d" | |
| "Illegal in io_xmit( ) index" | |
| "Illegal index in io_input( )" | |
| "Illegal index in ioport_xmit( )" | |
| IOPORT SYSTEM | |
| "No 8255 . . . port terminated" | * |
| "Set_pwr state: hw_ver = 1" | |
| "Set_pwr state: hw_ver = 2" | |
| "Set_power_state: Can't power on" | * |
| "Set_power_state: Can't power off" | * |
| "Converse: illegal return from uccom( )" | |
| "Switch failure in reset_port( ) function" | |
| "Command buffer full in add_cmd( )" | |
| "Unrecognizable command in make_cmd( )" | |
| "Illegal number of data bytes in make_cmd( )" | |
| "Illegal number of data bytes in make_cmd( )" | |

Having described and illustrated the principles of our invention with reference to a preferred embodiment, it will be apparent that the invention can be modified in arrangement and detail without departing from such principles. Accordingly, we claim as our invention all such embodiments as may come within the scope and spirit of the following claims and equivalents thereto.

What is claimed is:

1. A hemodialysis machine comprising:
at least one dialysate pump configured to move dialysate to a dialyzer;
a blood pump operable to move blood to the dialyzer;
a user/machine interface including
  (a) individually selectable digits zero through nine, and
  (b) a video screen; and
at least one processor, the processor and user/machine interface configured to
  (i) enable a cumulative ultrafiltration value to be entered via selection from the digits,
  (ii) enable a total time to be entered via selection from the digits, and
  (iii) enable a plurality of ultrafiltration values as steps over time forming a profile to be entered after entry of the cumulative ultrafiltration value and the total time;
  (iv) display a shape of the entered profile on the video screen; and
  (v) cause the entered cumulative ultrafiltration value to be removed via the dialyzer, within or over the entered total time, according to the entered profile.

2. The hemodialysis machine of claim 1, wherein the video screen is configured to display indicia corresponding to the ultrafiltration profile, the indicia selectable to enable the profile to be entered.

3. The hemodialysis machine of claim 2, wherein the display of the shape of the entered profile occurs as the plurality of ultrafiltration values are entered.

4. The hemodialysis machine of claim 1, wherein the total time is enterable via a single selection from the digits and the cumulative ultrafiltration value is enterable via a single selection from the digits.

5. The hemodialysis machine of claim 1, which includes an enclosure for the dialysate and blood pumps, the video screen mounted directly onto the enclosure.

6. The hemodialysis machine of claim 1, wherein the profile is entered while the video screen displays an ultrafiltration profile screen, which is different than a screen in which the cumulative ultrafiltration value and total time are entered.

7. The hemodialysis machine of claim 1, wherein the cumulative ultrafiltration value is a total volumetric fluid loss per the total time.

8. The hemodialysis machine of claim 1, wherein the total time is a total treatment time.

9. The hemodialysis machine of claim 1, wherein the video screen is configured to display each of the entered total time, entered cumulative ultrafiltration value and entered ultrafiltration profile.

10. A method of operating a dialysis machine including at least one dialysate pump configured to move dialysate to a dialyzer, a blood pump operable to move blood to the dialyzer, a video screen and at least one processor, the method comprising:
enabling a cumulative ultrafiltration value to be entered;
enabling a total time to be entered;
enabling a plurality of ultrafiltration values as steps over time forming a profile to be entered after entering the cumulative ultrafiltration value and the total time;
displaying a shape of the entered profile on the video screen; and
after entry of the total time, cumulative ultrafiltration value and ultrafiltration profile, enabling the entered cumulative ultrafiltration value to be removed via the dialyzer, within or over the entered total time, according to the entered ultrafiltration profile.

11. The method of claim 10, which includes displaying each of the entered total time, entered cumulative ultrafiltration value and entered ultrafiltration profile on the video screen.

12. The method of claim 10, wherein displaying the shape of the entered profile occurs as the plurality of ultrafiltration values are entered.

13. The method of claim 10, which includes enabling at least one of the total time and cumulative ultrafiltration value to be entered digitally.

14. The method of claim 10, wherein entering the cumulative ultrafiltration value includes entering a total volumetric fluid loss per the total time.

15. The method of claim 10, wherein entering the total time includes entering a total treatment time.

* * * * *

(12) INTER PARTES REEXAMINATION CERTIFICATE (0410th)
United States Patent
Connell et al.

(10) Number: US 7,264,730 C1
(45) Certificate Issued: Jul. 24, 2012

(54) METHODS FOR KIDNEY DIALYSIS

(75) Inventors: Mark E. Connell, Sandy, OR (US); Robert A. Bedient, Portland, OR (US); Raymond Elsen, Antwerp (BE); Michael E. Hogard, Oregon City, OR (US); Harley D. Johnson, Portland, OR (US); Thomas D. Kelly, Portland, OR (US); Jean McEvoy Long, Portland, OR (US); Bruce A. Peterson, Milwaukie, OR (US); William G. Preston, Jr., Portland, OR (US); Dalibor J. Smejtek, Beaverton, OR (US)

(73) Assignee: Baxter International Inc., Deerfield, IL (US)

Reexamination Request:
No. 95/001,156, Mar. 13, 2009

Reexamination Certificate for:
| | |
|---|---|
| Patent No.: | 7,264,730 |
| Issued: | Sep. 4, 2007 |
| Appl. No.: | 10/461,237 |
| Filed: | Jun. 13, 2003 |

Related U.S. Application Data

(60) Continuation of application No. 09/711,240, filed on Nov. 13, 2000, now abandoned, which is a continuation of application No. 09/067,922, filed on Apr. 28, 1998, now abandoned, which is a continuation of application No. 08/479,688, filed on Jun. 7, 1995, now Pat. No. 5,744,027, which is a division of application No. 08/122,047, filed on Sep. 14, 1993, now Pat. No. 5,486,286, which is a division of application No. 07/688,174, filed on Apr. 19, 1991, now Pat. No. 5,247,434.

(51) Int. Cl.
*B01D 61/32* (2006.01)

(52) U.S. Cl. ............... 210/646; 210/138; 210/143; 210/321.65; 210/929; 345/156; 345/173; 345/530; 604/6.09; 700/273

(58) Field of Classification Search .................. None
See application file for complete search history.

(56) References Cited

To view the complete listing of prior art documents cited during the proceeding for Reexamination Control Number 95/001,156, please refer to the USPTO's public Patent Application Information Retrieval (PAIR) system under the Display References tab.

*Primary Examiner* — Krisanne Jastrzab

(57) ABSTRACT

A number of improvements relating to methods and apparatuses for kidney dialysis are disclosed. These include methods such as supplying a dialysis machine including a touch screen interface to a machine user and supplying to the machine user accessory devices to be used with the dialysis machine in operation.

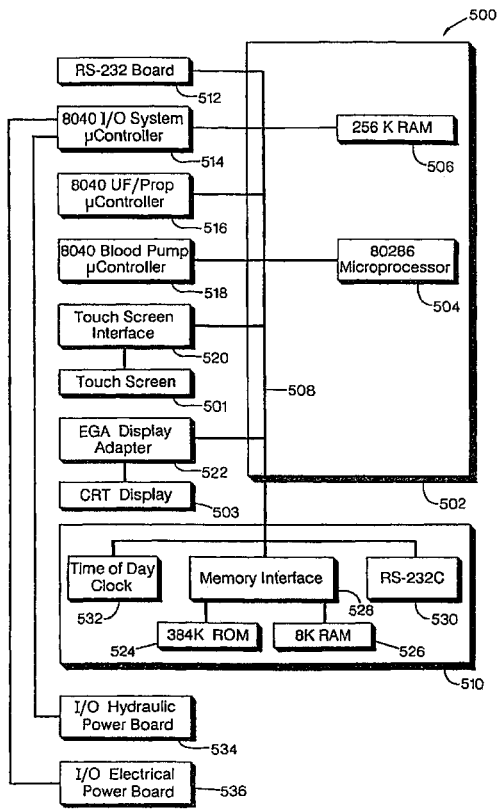

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-15 are cancelled.

* * * * *